US012589151B2

(12) United States Patent
Melchiori et al.

(10) Patent No.: US 12,589,151 B2
(45) Date of Patent: \*Mar. 31, 2026

(54) T CELL MODIFICATION

(71) Applicant: USWM CT, LLC, Louisville, KY (US)

(72) Inventors: Luca Melchiori, Oxfordshire (GB); Joanna Brewer, Oxfordshire (GB)

(73) Assignee: USWM CT, LLC, Louisville, KY (US)

( * ) Notice: Subject to any disclaimer, the term of this patent is extended or adjusted under 35 U.S.C. 154(b) by 970 days.

This patent is subject to a terminal disclaimer.

(21) Appl. No.: 17/297,380

(22) PCT Filed: Nov. 29, 2019

(86) PCT No.: PCT/EP2019/083196
§ 371 (c)(1),
(2) Date: May 26, 2021

(87) PCT Pub. No.: WO2020/109616
PCT Pub. Date: Jun. 4, 2020

(65) Prior Publication Data
US 2024/0050570 A1 Feb. 15, 2024

(30) Foreign Application Priority Data

Nov. 30, 2018 (GB) ...................................... 1819540

(51) Int. Cl.

| | |
|---|---|
| *A61K 35/17* | (2025.01) |
| *A61K 40/11* | (2025.01) |
| *A61K 40/32* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 5/0783* | (2010.01) |
| *C12N 15/86* | (2006.01) |

(52) U.S. Cl.
CPC .......... *A61K 40/4268* (2025.01); *A61K 40/11* (2025.01); *A61K 40/32* (2025.01); *A61P 35/00* (2018.01); *C07K 14/7051* (2013.01); *C07K 14/70517* (2013.01); *C12N 5/0636* (2013.01); *C12N 15/86* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 7,388,072 B2 | 6/2008 | Zhang et al. | |
| 7,521,197 B2 | 4/2009 | Savage | |
| 7,666,604 B2 | 2/2010 | Jakobsen et al. | |
| 10,117,918 B2 | 11/2018 | Sahin et al. | |
| 11,286,289 B2 | 3/2022 | Tribble et al. | |

| | | | |
|---|---|---|---|
| 2004/0077045 A1 | 4/2004 | Zhang et al. | |
| 2005/0118676 A1 | 6/2005 | Qi et al. | |
| 2009/0324566 A1 | 12/2009 | Shiku et al. | |
| 2012/0009162 A1 | 1/2012 | Yasukawa | |
| 2014/0378389 A1 | 12/2014 | Robbins et al. | |
| 2017/0333480 A1 | 11/2017 | Cooper et al. | |
| 2019/0100592 A1* | 4/2019 | Hamilton ....... A61K 39/464488 |
| 2019/0135892 A1 | 5/2019 | Tribble et al. | |
| 2019/0144521 A1 | 5/2019 | Tribble et al. | |
| 2020/0223899 A1* | 7/2020 | Veatch ............... A61K 40/4251 |
| 2021/0040558 A1* | 2/2021 | Schumacher .......... A61P 35/00 |
| 2022/0031753 A1 | 2/2022 | Tribble et al. | |

FOREIGN PATENT DOCUMENTS

| | | | |
|---|---|---|---|
| CN | 101287831 A1 | 10/2008 | |
| CN | 104853766 A | 8/2015 | |
| CN | 105163765 A | 12/2015 | |
| CN | 106749620 A | 5/2017 | |
| CN | 107074970 A | 8/2017 | |
| CN | 108366995 A | 8/2018 | |
| CN | 110325633 A | 10/2019 | |
| CN | 110582299 A | 12/2019 | |
| CN | 110951690 A | 4/2020 | |
| CN | 111315402 A | 6/2020 | |
| CN | 13166778 | * 7/2021 | |
| CN | 113166778 A | 7/2021 | |
| EP | 1930433 | 6/2008 | |
| JP | 2007527191 A | 9/2007 | |
| JP | 2012531904 A | 12/2012 | |
| JP | 2013126415 A | 6/2013 | |
| JP | 2013/541332 | 11/2013 | |
| JP | 2019511222 A | 4/2019 | |
| KR | 102349677 | 1/2022 | |
| KR | 102523449 | 4/2023 | |
| RU | 2355703 | 5/2009 | |

(Continued)

OTHER PUBLICATIONS

Chua I.C., CD8 co-receptor modifications to enhance T cell immunotherapy, 2013, Thesis, pp. 1-193.*
Brett et al, CN 13166778 translation pp. 1-31.*
Hiasa et al "Long-term phenotypic, functional and genetic stability of cancer-specific T-cell receptor (TCR) αβ genes transduced to CD8+ T cells" Gene Therapy 2008, vol. 15, pp. 695-699.
Lyons et al "Influence of Human CD8 on Antigen Recognition by T-Cell Receptor-Transduced Cells" Cancer Res, 2006, vol. 66, No. 23, pp. 11455-11461, doi: 10.1158/0008-5472.CAN-06-2379.
Aggen et al. "Single-Chain VaVβ T Cell Receptors Function Without Mispairing With Endogenous TCR Chains", Gene Ther. Apr. 2012; 19(4): 365-374 (Year: 2012).
Anonymous: EMBL CDS: BAS03571: Sequence: UPI000676CA51 (Aug. 1, 2015) Retrieved from Internet URL http://www.uniprotorg/uniparcJUP!000676CA51. Retrieved on Sep. 6, 2017.

(Continued)

*Primary Examiner* — Maria Marvich
(74) *Attorney, Agent, or Firm* — Grimes & Yvon LLP

(57) ABSTRACT

The present invention provides a modified T cell or population of modified T cells comprising a heterologous recombinant T cell receptor (TCR) and heterologous recombinant co-receptor, additionally provided are methods of producing the modified T cell or population of modified T cells and their use in the treatment of cancer.

8 Claims, 20 Drawing Sheets

Specification includes a Sequence Listing.

(56) References Cited

FOREIGN PATENT DOCUMENTS

| WO | WO2000/020445 | | 4/2000 |
|----|----|----|----|
| WO | WO 02/094981 | | 11/2002 |
| WO | WO 2002102852 | * | 12/2002 |
| WO | WO2004/074322 | | 9/2004 |
| WO | 2011001152 A1 | | 1/2011 |
| WO | WO2012/038055 | | 3/2012 |
| WO | WO 2012054825 A1 | | 4/2012 |
| WO | WO 2013039889 A1 | | 3/2013 |
| WO | WO 2016055785 A1 | | 10/2015 |
| WO | 2016054086 A1 | | 4/2016 |
| WO | 2016073755 A2 | | 5/2016 |
| WO | WO 2016191756 | | 12/2016 |
| WO | 2017133175 A1 | | 8/2017 |
| WO | 2017158103 A1 | | 9/2017 |
| WO | WO 2017174823 | * | 10/2017 |
| WO | 2018055140 A1 | | 3/2018 |
| WO | 2018170338 A2 | | 9/2018 |
| WO | 2019204662 A1 | | 10/2019 |

OTHER PUBLICATIONS

Anonymous: EMPB CDS: BAF94626—Sequence: UPI000'1614056 (Dec. 30, 2007) Retrieved from Internet URL http://www.uniprotorgilmiparc/UPI0001614056. Retrieved on Sep. 6, 2017.

Colman, "Effects of Amino Acid Sequence Changes on Antibody-Antigen Interactions", Biomolecular Research Institute, Research in Immunology, 1994, vol. 245, No. 1, pp. 33-36.

Cordoba et al., "The Large Ectodomains of CD45 and CD148 Regulate Their Segregation from the Inhibition of Ligated Ir-Cell Receptor", Blood, May 23, 2013, vol. 121, No. 21, pp. 4295-4302.

De la Hera et al., "Structure of the T Cell Antigen Receptor {TCR) Two CD3e Subunits in a Functional TCR/CD3 Complex", J_ Exp_ Med., vol. 173, Jan. 1991, pp. 7-17.

Duffour et al., "A MAGE-A4 Peptide Presented by HLA-A2 is Recognized by Cytolytic T Lymphocytes", Eur. J. mmunoL 1999, vol. 29, pp. 3329-3337.

English translation of Chinese Office Action issued Jun. 1, 2021, in corresponding Chinese Appln. No. 017800317102.

Fidler IJ. "Biological heterogeneity of cancer: implication to therapy", Hum Vaccin Immunother. Aug. 2012;8(8):1141-2. (Year: 2012).

Fujiwara-Kuroda et al. "Prognostic value of MAGEA4 in primary lung cancer depends on subcellular localization and p53 status", Int J Oneal. Aug. 2018;53(2):713-724. (Year: 2018).

Gasser, et al., "Antibody Production with Yeast and Filamentous Fungi: On the Road to Large Scale?", Biotechnol. Lett (2007) vol. 29, No. 2, p. 201-212.

Hillig, et al., "High-resolution Structure of HLA-A*0201 in Complex with a Tumour-specific Antigenic Peptide Encoded DY the MAGE-A4 Gene", J_ Mal_ Biol. (2001) vol. 310, p. 1167-1176_.

Holler, et al., "Quantitative Analysis of the Contribution of TCR/pepMHC Affinity and COB to T Cell Activation", Immunity (Feb. 2003) vol. 18, p. 255-264.

Ikeda et al. "In vivo persistence of adoptively transferred TCR gene-transduced lymphocytes with anti-tumor reactivity in patients with MAGE-A4 expressing esophageal cancer", J Immunother Cancer. 2013; 1 (Suppl 1 ): 03. (Year: 2013).

Jia, et al., "Identification of Two Novel HLA-A*0201-Restricted CTL Epitopes Derived from MAGE-A4", Clinical and Developmental Immunology, vol. 2010, Artilce 567594, 7 pages, 2010.

The Merck Manuals Online Medical Library, [online]. Whitehouse Station, NJ: Merck Research Laboratories, 2006-2007. [retrieved on Oct. 19, 2020]. <URL: https://www.merckmanuals.com/professional/hematology- and- oncology/overview-of-cancer/cellular-and-molecular-basis-of-cancer> (Year: 2020).

Ozawa, et al., "Comprehensive analysis of the functional TCR repertoireat the single-cell level", Biochemical and Biophysical Research Communications 367 (2008) 820-825.

Pakula, et al., "Genetic Analysis of Protein Stability and Function", Annu. Rev. Genet {1989) vol. 23, p. 289-310.

Rudikoff et al., "Single amino acid substitution altering antigen-binding specificity", Proc Natl Acad Sci USA. Mar. 1982; 79(6): 1979-1983. (Year: 1982).

Safdari et al., "Antibody Humanization Methods—A Review and Update", Biotechnology and Genetic Engineering Reviews, vol. 29, No. 2, pp. 175-186, 2013.

Wahl, et al. " HLA Class I Molecules Reflect an Altered Host Proteome After Influenza Virus Infection", Human Immunology (2010) vol. 71, p. 14-22.

Hiasa et al., "Rapid αξ TCR-mediated responses in γδ T cells transduced with cancer-specific TCR genes", Gene Therapy (2009) 16, pp. 620-628.

Willemsen et al., "Redirecting human CD4+ T lymphocytes to the MHC class I-restricted melanoma antigen MAGE-A1 by TCRαξ gene transfer requires CD8α", Gene Therapy (2005) 12, pp. 140-146.

English Translation of Japanese Office Action dated Mar. 12, 2024, for Japanese Patent Application No. 2021-530124, 7 pages.

English Translation of Japanese Office Action dated May 21, 2021, for Japanese Patent Application No. 2018-552872, 4 pages.

English Translation of Korean Office Action dated Aug. 8, 2021, for Korean Patent Application No. 10-2018-7032168, 7 pages.

English Translation of Chinese Office Action dated Jul. 10, 2024, for Chinese Patent Application No. 201980089522.4, 8 pages.

Anderson et al., "Abstract 2313: Enhanced activity of second-generation MAGE-A4 Spear T-cells through co-expression of a CDS," published Jul. 2019, Cancer Research, 4 pages.

Willemsen et al., "CD8a Coreceptor to Improve TCR Gene Transfer to Treat Melanoma: Down-Regulation of Tumor-Specific Production of IL-4, IL-5, and IL-10," The Journal of Immunology, 2006, 177 (2): 991-998.

Xue et al., "Human MHC Class I-restricted high avidity CD4+ T cells generated by co-transfer of TCR and CDS mediate efficient tumor rejection in vivo," OncoImmunology 2:1, e22590; Jan. 2013 (Year: 2013).

Robbins et al., "Single and Dual Amino Acid Substitutions in TCR CD Rs can Enhance Antigen-Specific T Cell Functions," J Immunol (2008) 180 (9): 6116-6131. (Year: 2008).

Chuanlin et al., "Current Medical Immunology," Shanghai Medical University Press, p. 36, published on Oct. 31, 1998, 4 pages with English translation.

Kessels et al., "Generation of T Cell Help through a MHC Class I-Restricted TCR," The Journal of Immunology, 2006, 177 (2): 976-982.

Cole et al., "CD8: Adhesion Molecule, Co-Receptor and Immuno-Modulator," Cellular & Molecular Immunology, 2004, 1 (2): 81-88.

McNicol et al., "CD8α/α homodimers fail to function as co-receptorfor a CD8-dependent TCR," European Journal of Immunology, 2007, 37: 1634-1641.

Laugel et al., "Different T Cell Receptor Affinity Thresholds and CD8 Coreceptor Dependence Govern Cytotoxic T Lymphocyte Activation and Tetramer Binding Properties," The Journal of Biological Chemistry, 2007, 282 (33): 23799-23810.

Morris et al., "A critical role of T cell antigen receptor-transduced MHC class I-restricted helper T cells in tumor protection," PNAS, 2005, 102 (22): 7934-7939.

Bethune Michael T., et al., "Isolation and characterization of NY-ESO-1-specific T cell receptors restricted on various MHC molecules11", Proceedings of the National Academy of Sciences of the United States of America, vol. 115, No. 45, pp. E10702-E10711, Nov. 6, 2018.

Soto, Carolina M., et al., "MHC-class I-restricted CD4 T cells: a nanomolar affinity TCR has improved anti-tumor efficacy in vivo compared to the micromolar wild-type TCR11", Cancer Immunology Immunotherapy, vol. 62, No. 2, pp. 359-369, Feb. 2013.

Zhou et al: "T-cell receptor gene transfer exclusively to human CD8+ cells enhances tumor cell killing" Blood,2012, vol. 120, No. 22,pp. 4334-4342, DOI.

Dorrie et al: "Human Adenovirus specific γ/δ and CD8+ cells generated by T-Cell receptor transfection to treat adenovirus infection after allogeneic stem cell transplantation" PLoS One,2014, vol. 9, No. 10,e109944 (pp. 1-10),doi:10.1371/journal.pone.0109944.

(56) References Cited

OTHER PUBLICATIONS

Bajwa et all "440. Reprogramming CD4 T Cells into Cytotoxic CD8 Cells by Forced Expression of CD8αβ and Class I Restricted T Cell Receptors", Molecular Therapy, May 2018, vol. 26, No. 5S1,p. 20.

* cited by examiner

Ntd dark grey / ADP-A2M4 light grey / ADP-A2M4-CD8 black

Ntd dark grey / ADP-A2M4 light grey / ADP-A2M4-CD8 black

Ntd dark grey / ADP-A2M4 light grey / ADP-A2M4-CD8 black

Ntd dark grey / ADP-A2M4 light grey / ADP-A2M4-CD8 black

T CELL MODIFICATION

CROSS REFERENCE TO RELATED APPLICATIONS

This application is a U.S. National Phase application under 35 U.S.C. 371 of International Application No. PCT/EP2019/083196, filed Nov. 29, 2019, which claims priority to and the benefit of GB Application No. GB 1819540.4 filed Nov. 30, 2018, the entire disclosure of each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 27, 2022, is named SequenceListing.txt and is 15,698 bytes in size.

FIELD

This invention relates to the modification of T cells to increase their cytotoxic activity and the use of modified T cells in immunotherapy, for example, for the treatment of cancer.

BACKGROUND

Immunotherapeutics are poised to transform the cancer treatment landscape with the promise of long-term survival (McDermott et al., Cancer Treat Rev. 2014 October; 40(9): 1056-64). There is a clear unmet medical need for new immunomodulatory drugs to expand patient population and range of tumor types. In addition, new agents are needed to enhance the magnitude and duration of anti-tumor responses. The development of these agents has been possible because of the in-depth understanding of the basic principles controlling T-cell immunity over the last two decades (Sharma and Allison, Cell. 2015 Apr. 9; 161(2): 205-14). This typically requires tumor specific CD4+ and CD8+ T-cells recognising tumor-associated peptide antigens presented by MHC molecules. Different vaccination strategies and adoptive transfer of ex vivo expanded tumor infiltrated lymphocytes have in some cases demonstrated the ability of tumor specific T-cells to treat late stage cancer (Rosenberg et al., Nat Med. 2004 September; 10(9): 909-15). However, high tolerance to tumour antigens combined with the potent immunosuppressive microenvironment often present at the tumour site manifests in suboptimal activation of T cell anti-tumor activity. Thus, individuals lacking high affinity T-cells may not respond to immune checkpoint blockade therapies, such as anti-PD-1 and anti-CTLA-4, due to T-cell tolerance to self-antigens.

Genetic engineering may help to overcome the problems of the low frequency of endogenous high affinity T cells to tumor antigens by the generation of high affinity T cell receptors (TCR), and provide clinical benefit to patients who do not respond to treatment with checkpoint inhibitors. This approach has been shown to increase the affinity of the wild type TCRs for their natural ligand peptide/MHC class I complex 10-1000 fold in vitro for several antigens including gp100, MAGE-A3 and NY-ESO-1 (Li et al., Nat Biotechnol. 2005 March; 23(3): 349-54; Robbins et al., J Immunol. 2008 May 1; 180(9): 6116-31).

Higher affinity TCRs allow T cells to respond to lower levels of antigen; this is important where tumour microenvironment has adapted to reduce antigen expression and decrease expression of MHC class I molecules (Barrett and Blazar, N Engl J Med. 2009 Jul. 30; 361(5): 524-5; Marincola et al., Adv Immunol. 2000; 74: 181-273). Redirecting T cells towards tumours has been achieved via TCR-engineered T cell therapies or with T-cell redirecting biologics (Bossi et al., Cancer Immunol Immunother. 2014 May; 63(5): 437-48; Fan et al., J Hematol Oncol. 2015 Dec. 21; 8: 130).

T cell therapy has shown curative potential for treatment of some recurrent or high risk tumors (Dudley et al., J Immunother. 2003 July-August; 26(4): 332-42; Dudley et al., J Clin Oncol. 2005 Apr. 1; 23(10): 2346-57; Kalos et al., Sci Transl Med. 2011 Aug. 10; 3(95): 95ra73). There are currently two methods being used to genetically engineer patient T cells to recognise tumour antigens including chimeric antigen receptors (CARs) and affinity matured TCRs. However, CARs are restricted to targeting only epitopes on the cell surface. TCR-based therapeutics can recognise not only cell surface proteins, but also internal cell proteins. In addition, the TCR approach more closely mimics the natural function of the T cell by recruiting the endogenous signalling molecules and spatial-temporal interactions between T cells and their specific targets. It is, however, restricted to individuals who share the appropriate MHC restriction, recognised by the TCR and may require the parallel development of patient selection assays for both the HLA type and the antigen expression.

The binding of a MHC Class I-restricted T cell receptor (TCR) to the peptide-MHC complex is stabilized by a glycoprotein called CD8 (cluster of differentiation 8), which also recruits the Src-family kinase Lck, and potentiates signalling. CD8 binding to the constant portion of MHC class I results in increased affinity of binding and decreased threshold of response to antigen on target cells (Gao, Nature. 1997 Jun. 5; 387(6633): 630-4; Artyomov et al., Proc Natl Acad Sci USA. 2010 Sep. 28; 107(39): 16916-21). Addition of a CD8 transgene into a TCR lentiviral vector could confer to CD4+ T cells a similar increased response, augmenting their ability to provide helper function to CD8+ T cells as well as additional direct tumour cell killing, possibly resulting in enhanced clinical efficacy. CD8a/CD83 (cluster of differentiation 8) is a heterodimeric transmembrane glycoprotein expressed by cytotoxic T cells, natural killer (NK) cells and dendritic cells. It binds to conserved regions on Class I peptide-Major Histocompatibility antigens (pMHCs, in man these are normally described as peptide-Human Leucocyte Antigens or pHLAs) and in doing so it acts as a generic co-receptor for MHC peptide-specific binding by T Cell Receptors (TCRs). CD8α/CD8β is not found in mature CD4+ T cells where their antigen-specific TCRs bind to the related but different Class II pMHC antigens and where the CD4 homodimer acts as the TCR co-receptor.

The most common type of co-receptor-dependent TCRs are heterodimeric transmembrane glycoproteins with an α and β polypeptide chain. When α/β TCRs bind Class I pMHC antigens they trigger an intracellular signalling cascade of phosphorylation events that activate a plethora of cellular events including the killing of pMHC-expressing target cells by cytotoxic T cells. This signalling cascade is initiated by the phosphorylation of TCR-bound CD3 transmembrane proteins by Lck (Lymphocyte-specific protein tyrosine kinase).

Intracellular associations between CD8α/CD8β and Lck are thought to potentiate TCR signalling. In humans, in addition to the CD8α/CD8β heterodimer, approximately one third of CD8+ cells also display a CD8α/CD8β homodimeric form. In some intestinal T cells, NK cells, and γ/5 T cells, only this homodimeric form is found.

Evidence suggests that in humans, this CD8a homodimer could fully functionally substitute for the CD8α/CD8β heterodimer (Cole et al., Immunology. 2012 October; 137(2): 139-48).

In vivo, the concurrent binding of TCRs and CD8 dimers to Class I pHLA impacts on the thymic positive/negative selection of T cell clones. This dictates the pHLA antigen affinity of the TCRs expressed by these T cell clones. In general, the TCR antigen affinities in pathogen-associated pHLA-reactive T cell clones are higher than the equivalent T cell clones that recognize cancer-associated antigens. TCR affinity enhancement technologies can increase the affinity of cancer-reactive TCRs to close to that of pathogen-reactive TCRs. These increases in TCR affinity result in TCRs that are usually CD8 co-receptor independent. Cellular transduction of CD4+ T cells with gene expression vectors that express these TCRs creates a novel entity of Class I pHLA specific CD4+ T cells with killer and helper functions which otherwise could only normally be activated by Class II-specific peptide-antigens (Tan et al., Clin Exp Immunol. 2017 January; 187(1): 124-137). These TCRs allow T cells to more efficiently recognize their cancer target cells than do their wildtype parent TCRs. Importantly, pHLA antigen specificity is maintained even in CD8+ T cells, i.e., in the presence of endogenous CD8 co-receptors.

Although co-receptor independence means that these affinity-enhanced TCRs can also function to an extent in CD4+ T cells it is clear that the optimum TCR affinity in CD4+ T cells is higher than it is in CD8+ T cells (Tan et al. supra). There is an ongoing need for new and improved TCR-based therapeutics to enhance the magnitude and duration of anti-tumour responses in patients.

SUMMARY

The present inventors have recognised that the co-expression of a heterologous CD8 co-receptor in T cells that express a heterologous T cell receptor increases the activity of the T cells.

A first aspect of the invention provides a T cell or a population of modified T cells that express a heterologous CD8 co-receptor and a heterologous T cell receptor (TCR).

Preferably, the heterologous TCR specifically binds to an HLA displaying a peptide fragment of a tumour antigen (pHLA) expressed by the cancer cells. According to the invention, the heterologous TCR may specifically bind to a cancer or tumour antigen or peptide thereof, a peptide, antigenic peptide or peptide fragment of an antigen preferably a cancer or tumour antigen, optionally presented on HLA (pHLA), preferably expressed by a tumour cell or a cancer cell. According to the present invention the tumour antigen may be a cancer-testis antigen, NY-ESO-1, MART-1 (melanoma antigen recognized by T cells), WT1 (Wilms tumor 1), gp100 (glycoprotein 100), tyrosinase, PRAME (preferentially expressed antigen in melanoma), p53, HPV-E6/HPV-E7 (human papillomavirus), HBV, TRAIL, DR4, Thyroglobin, TGFBII frameshift antigen, LAGE-1A, KRAS, CMV (cytomegalovirus), CEA (carcinoembryonic antigen), AFP (α-fetoprotein), MAGE-A1, MAGE-A2, MAGE-A3, MAGE-A4, MAGE-A6, MAGE-A8, and MAGE-A9, MAGE-A10, or MAGE-A12. Preferably the tumour antigen is MAGE-A4. Preferably the tumour antigen peptide fragment has the amino acid sequence GVYDGREHTV. According to the present invention the TCR may HLA displaying a peptide fragment of a tumour antigen (pHLA) wherein the HLA is HLA class I and/or HLA class II, preferably HLA class I. Preferably the HLA is HLA-A2 or HLA-A*02 or an HLA-A2+ or HLA-A*02 positive HLA, preferably HLA-A*0201.

The modified T cell or T cells may comprise a heterologous nucleic acid encoding the TCR and a heterologous nucleic acid encoding the CD8 co-receptor, or may comprise a heterologous nucleic acid encoding the TCR and heterologous CD8 co-receptor.

Preferably, the modified T cell is CD4+ or CD8+ or the population of modified T cells comprises or consists of CD4+ T cells or CD8+ T cells or a mixture of CD4+ T cells and CD8+ T cells.

Preferably, the CD8 co-receptor is a CD8α co-receptor. A CD8α may co-receptor may comprise the amino acid sequence of SEQ ID NO: 1 or a variant thereof. The CD8α co-receptor may be a homodimer, CD8αα. In the alternative the CD8 co-receptor may comprise CD8αβ co-receptor heterodimer.

The heterologous TCR may be an affinity enhanced TCR, for example a specific peptide enhanced receptor (SPEAR) TCR. The heterologous TCR that is an affinity enhanced TCR, or specific peptide enhanced receptor (SPEAR) TCR may be engineered to optimize specificity and/or activity against the antigenic peptide and/or reduce the risk of cross-reactivity and/or alloreactivity optionally when HLA presented. Accordingly the (SPEAR) TCR specificity may be assessed by mapping the response of T cells comprising the TCR to panels of synthetic variants of the antigenic peptide using combinatorial substitutions at each amino acid with every other possible amino acid (X-Scan), to identify potentially cross-reactive peptides in the human and common pathogen proteomes. The (SPEAR) TCR may then be screened against normal (non-tumour) primary cells from multiple organ systems, induced pluripotent stem cell-derived cells (iCells), and autologous whole blood to test for off-target reactivity, and against a panel of EBV-derived B-lymphoblastic cell lines expressing a wide range of HLA molecules to assess the risk of cross-reactivity and/or alloreactivity. Alloreactivity is determined by assay in antigen negative cells expressing HLA alleles to identify presence of exclusionary alleles. T cells with heterologous TCR selected to be specific for antigenic peptide without cross reactivity and/or defined HLA allelic exclusion may thereby be produced. The TCR or T cell expressing the heterologous TCR may be further selected as described herein for binding affinity and avidity to the antigenic peptide optionally HLA presented. The TCR or T cell expressing the heterologous TCR may also be further selected as described herein for potency as assessed by a variety of in vitro assays, including T cell proliferation, IFN-γ release and cytotoxicity in response to antigen-positive tumor lines in 2D and 3D culture, and cytokine release in response to freshly prepared antigen-positive primary tumor material.

A second aspect of the invention provides a method of producing a T cell or a population of modified T cells comprising modifying a T cell or population of T cells to express a heterologous CD8 co-receptor and a heterologous T cell receptor according to the invention.

The T cell or population of T cells may be obtained from an individual, optionally wherein the individual comprises tumour or cancer.

The T cells may be modified by introducing a nucleic acid encoding the TCR and a nucleic acid encoding the CD8 co-receptor into the T cells or by introducing a heterologous nucleic acid encoding the heterologous TCR and heterologous CD8 co-receptor according to the invention.

A third aspect of the invention provides a pharmaceutical composition comprising a T cell or a population of modified T cells according to the first aspect or produced by the method of the second aspect and a pharmaceutically acceptable excipient.

A fourth aspect of the invention provides a method of treatment of cancer comprising administering to an individual in need thereof a population of modified T cells according the first aspect or produced by the method of the second aspect; or a pharmaceutical composition of the third aspect.

The TCR of the population of modified T cells may bind specifically and/or selectively to tumour or cancer cells in the individual, optionally with high affinity and/or high avidity. For example the TCR may bind or specifically and/or selectively bind to a cancer or tumour antigen or peptide thereof, a peptide, antigenic peptide or peptide fragment of an antigen preferably a cancer or tumour antigen, optionally presented on HLA (pHLA), preferably expressed by a tumour cell or a cancer cell A fifth aspect of the invention provides a method of treating cancer in an individual comprising;

providing a population of T cells obtained from a donor individual, modifying the population of T cells to express a heterologous CD8 co-receptor and a heterologous T cell receptor, thereby producing a population of modified T cells according to the invention, and administering the population of modified T cells to a recipient individual.

According to the present invention and to the fourth and fifth aspect the cancer may be synovial sarcoma, myxoid/round cell liposarcoma (MRCLS), head and neck cancer, head and neck SCC (squamous cell carcinoma), melanoma, esophageal cancer, ovarian cancer, gastric cancer (stomach), bladder cancer, lung cancer, non-small cell lung NSCLC (squamous, adenocarcinoma, adenosquamous, large cell carcinoma), metastatic or advanced NSCLC, urothelial cancer or tumour, esophagogastric junction cancer (EGJ), optionally wherein the cancer or tumour express a MAGE protein or peptide, preferably MAGE-A4 protein or peptide. Alternatively the cancer may be any one of liver cancer, pancreatic cancer, colorectal cancer, lung cancer, metastatic stomach cancer, metastatic gastric cancer, metastatic liver cancer, metastatic ovarian cancer, metastatic pancreatic cancer, metastatic colorectal cancer, metastatic lung cancer, colorectal carcinoma or adenocarcinoma, lung carcinoma or adenocarcinoma, pancreatic carcinoma or adenocarcinoma, mucinous adenoma, ductal carcinoma of the pancreas.

The donor individual and the recipient individual may be the same (i.e. autologous treatment; the modified T cells are obtained from an individual who is subsequently treated with the modified T cells) or the donor individual and the recipient individual may be different (i.e. allogeneic treatment; the modified T cells are obtained from one individual and subsequently used to treat a different individual). Autologous refers to any material derived from a subject to which it is later to be re-introduced into the same subject.

A sixth aspect of the invention provides a population of modified T cells according the first aspect or produced according to the second aspect or the pharmaceutical composition of the third aspect for use in a method of the fourth or fifth aspects; and the use of a population of modified T cells according the first aspect or produced according to the second aspect or the pharmaceutical composition of the third aspect in the manufacture of a medicament for use in a method of the fourth or fifth aspects.

A seventh aspect of the invention provides an isolated nucleic acid comprising a nucleotide sequence encoding a heterologous TCR according to the invention, optionally in a single open reading frame, or in distinct and/or multiple open reading frames encoding the TCR alpha chain and the beta chain respectively and/or a nucleotide sequence encoding a heterologous CD8 co-receptor according to the invention, optionally in a single open reading frame, or in distinct open reading frames encoding the CD8 alpha chains or alpha chain and beta chain respectively. Alternatively, the chains of the TCR and/or CD8 co-receptor may be encoded on separate nucleic acids.

An eighth aspect of the invention provides a vector comprising an isolated nucleic acid of the seventh aspect. The vector may be an expression vector, which may further comprise regulatory elements for the expression of the encoded TCR and CD8 co-receptor of the nucleic acid of the invention. The invention further provides a first construct or vector which comprises a nucleic acid or nucleotide sequence encoding the alpha chain of a TCR according to the invention, and/or a second construct or vector which comprises nucleic acid encoding the beta chain of a TCR according to the invention and a third and/or fourth construct or vector which comprises nucleic acid encoding the CD8-co-receptor chain(s), alpha and/or beta. The present invention further provides a construct or vector comprising the (isolated) nucleic acid or nucleotide sequence of the invention which can be a preferably a viral vector, a gamma retroviral vector or a lentiviral vector, such as a VSVg-pseudotyped lentiviral vector. Preferably the construct or vector contains effective regulatory elements which will drive transcription and/or translation of the nucleic acid or nucleotide sequence of the invention encoding the TCR and/or CD8 co-receptor of the invention, optionally in a modified T cell.

Preferably the vector may be a viral vector, a gamma retroviral vector or a lentiviral vector, such as a VSVg-pseudotyped lentiviral vector, preferably a lentiviral vector.

A ninth aspect of the invention provides a viral particle comprising an isolated nucleic acid of the seventh aspect and/or vector of the eighth aspect.

A tenth aspect of the invention provides method of making a viral particle, optionally the viral particle according to the ninth aspect comprising transducing mammalian cells with a viral vector of the eighth aspect and one or more viral packaging and envelope vectors and culturing the transduced cells in a culture medium, such that the cells produce viral particles, optionally lentiviral particles that are released into the medium.

For example, HEK293T cells may be transfected with plasmids encoding viral packaging and envelope elements as well as a lentiviral vector comprising the nucleic acid or nucleotide sequence of the invention. According to the invention a VSVg-pseudotyped viral vector comprising the nucleic acid or nucleotide sequence of the invention may be produced in combination with the viral envelope glycoprotein G of the Vesicular stomatitis virus (VSVg) to produce a pseudotyped virus particle.

The present invention further provides a method of producing a T cell or a population of modified T cells according to the invention comprising introducing one or more than one copy of the nucleic acid according to aspect seven and/or vector according to aspect eight into a T cell or population of T cells, optionally wherein the nucleic acid and/or vector is comprised within a viral particle according to aspect nine or produced according to aspect ten, thereby modifying the T cell or population of T cells to express heterologous CD8 co-receptor and heterologous T cell receptor according to the invention.

These and other aspects and embodiments of the invention are described in more detail below.

DETAILED DESCRIPTION

This invention relates to modified T cells that express a heterologous CD8 co-receptor and a heterologous T cell receptor (TCR), and methods for their production and use.

T cells (also called T lymphocytes) are white blood cells that play a central role in cell-mediated immunity. T cells can be distinguished from other lymphocytes by the presence of a T cell receptor (TCR) on the cell surface. There are several types of T cells, each type having a distinct function.

T helper cells ($T_H$ cells) are known as CD4$^+$ T cells because they express the CD4 surface glycoprotein. CD4$^+$ T cells play an important role in the adaptive immune system and help the activity of other immune cells by releasing T cell cytokines and helping to suppress or regulate immune responses. They are essential for the activation and growth of cytotoxic T cells.

Cytotoxic T cells (Tc cells, CTLs, killer T cells) are known as CD8$^+$ T cells because they express the CD8 surface glycoprotein. CD8$^+$ T cells act to destroy virus-infected cells and tumour cells. Most CD8$^+$ T cells express TCRs that can recognise a specific antigen displayed on the surface of infected or damaged cells by a class I MHC molecule. Specific binding of the TCR and CD8 glycoprotein to the antigen and MHC molecule leads to T cell-mediated destruction of the infected or damaged cells.

T cells for use as described herein may be CD4$^+$ T cells; or CD4$^+$ T cells and CD8$^+$ T cells. For example, the T cells may be a mixed population of CD4$_+$ T cells and CD8$_+$ T cells. Accordingly the modified T cell may be a modified T-cell, optionally CD4$_+$ T cell or CD8$_+$ T cell, or the population of modified T-cells, optionally CD4$_+$ T cells; or CD8$_+$ T cells, or a mixed population of CD4$_+$ T cells and CD8$_+$ T cells.

Suitable T cells for use as described herein may be obtained from a donor individual. In some embodiments, the donor individual may be the same person as the recipient individual to whom the T cells will be administered following modification and expansion as described herein (autologous treatment). In other embodiments, the donor individual may be a different person to the recipient individual to whom the T cells will be administered following modification and expansion as described herein (allogeneic treatment). For example, the donor individual may be a healthy individual who is human leukocyte antigen (HLA) matched (either before or after donation) with a recipient individual suffering from cancer.

A method described herein may comprise the step of obtaining T cells from an individual and/or isolating T cells from a sample obtained from an individual optionally an individual with tumour and/or cancer.

A population of T cells may be isolated from a blood sample. Suitable methods for the isolation of T cells are well known in the art and include, for example fluorescent activated cell sorting (FACS: see for example, Rheinherz et al (1979) PNAS 76 4061), cell panning (see for example, Lum et al (1982) Cell Immunol 72 122) and isolation using antibody coated magnetic beads (see, for example, Gaudernack et al 1986 J Immunol Methods 90 179).

CD4$^+$ and CD8$^+$ T cells may be isolated from the population of peripheral blood mononuclear cells (PBMCs)

obtained from a blood sample. PBMCs may be extracted from a blood sample using standard techniques. For example, ficoll may be used in combination with gradient centrifugation (Boyum A. Scand J Clin Lab Invest. 1968; 21(Suppl.97):77-89), to separate whole blood into a top layer of plasma, followed by a layer of PBMCs and a bottom fraction of polymorphonuclear cells and erythrocytes. In some embodiments, the PBMCs may be depleted of CD14$^+$ cells (monocytes).

Following isolation, the T cells may be activated. Suitable methods for activating T cells are well known in the art. For example, the isolated T cells may be exposed to a T cell receptor (TCR) agonist. Suitable TCR agonists include ligands, such as a peptide displayed on a class I or II MHC molecule on the surface of an antigen presenting cell, such as a dendritic cell, and soluble factors, such as anti-TCR antibodies.

Activation refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

An anti-TCR antibody may specifically bind to a component of the TCR, such as αCD3, αCD3 or αCD28. Anti-TCR antibodies suitable for TCR stimulation are well-known in the art (e.g. OKT3) and available from commercial suppliers (e.g. eBioscience CO USA). In some embodiments, T cells may be activated by exposure to anti-αCD3 antibodies and IL2. More preferably, T cells are activated by exposure to anti-αCD3 antibodies and anti-αCD28 antibodies. The activation may occur in the presence or absence of CD14$^+$ monocytes. Preferably, the T cells may be activated with anti-CD3 and anti-CD28 antibody coated beads. For example, PBMCs or T cell subsets including CD4$^+$ and/or CD8$^+$ cells may be activated, without feeder cells (antigen presenting cells) or antigen, using antibody coated beads, for example magnetic beads coated with anti-CD3 and anti-CD28 antibodies, such as Dynabeads® Human T-Activator CD3/CD28 (ThermoFisher Scientific).

Following isolation and activation, the T cells may be modified to express a CD8 co-receptor and a T cell receptor (TCR) as described herein.

According to the present invention, the CD8 co-receptor may comprise a dimer or pair of CD8 chains which comprises a CD8-α and CD8-3 chain or a CD8-α and CD8-α chain. Preferably, the CD8 co-receptor is a CD8α co-receptor. A CD8α may co-receptor may comprise the amino acid sequence of at least 80% identity to SEQ ID NO: 1, SEQ ID NO: 1 or a variant thereof. The CD8α co-receptor may be a homodimer.

The CD8 co-receptor binds to class 1 MHCs and potentiates TCR signalling. A CD8 co-receptor may comprise the reference amino acid sequence of SEQ ID NO: 1 or may be a variant thereof. A variant may have an amino acid sequence having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity to the reference amino acid sequence. A CD8 co-receptor may be encoded by the reference nucleotide sequence of SEQ ID NO: 2 or may be a variant thereof. A variant may have a nucleotide sequence having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity to the reference nucleotide sequence According to the invention the heterologous CD8 co-receptor may comprise a CD8 co-receptor in which, in the Ig like V-type domain comprises CDRs having the sequence;

(i) VLLSNPTSG, CDR1, SEQ ID NO: 15, or amino acids 45-53 of SEQ ID NO: 1, (ii) YLSQNKPK, CDR2, SEQ ID NO: 16 or amino acids 72-79 of SEQ ID NO: 1, (iii) LSNSIM, CDR3, SEQ ID NO: 17 or amino acids 80-117 of SEQ ID NO: 1, or sequences having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity thereto.

According to the invention the heterologous CD8 co-receptor may comprise a CD8 co-receptor which comprises or in which, in the Ig like V-type domain comprises, residues 22-135 of the amino acid sequence of SEQ ID NO:1, or an amino acid sequence in which amino acid residues 22-44, 54-71, 80-117, 124-135 thereof have at least 70%, 75%, 80%, 85%, 90% or 95% identity to the sequence of amino acid residues 22-44, 54-71, 80-117, 124-135, CDR 1, CDR 2, CDR 3, respectively of SEQ ID NO:1 and in which amino acid residues 45-53, 72-79 and 118-123 have at least 70%, 75%, 80%, 85%, 90% or 95% identity to the sequence of amino acid residues 45-53, 72-79 and 118-123 respectively of SEQ ID NO:1.

According to the invention the CD8 co-receptor may comprise a CD8 co-receptor in which, or in which in the Ig like V-type domain, the sequence of:

(i) amino acid residues 22-44 thereof may have (a) at least 70%, 75%, 80%, 85%, 90% or 95% identity to the sequence of amino acid residues 22-44 of SEQ ID NO: 1, respectively or (b) may have one, two or three amino acid residues inserted or deleted relative to residues 22-44 of SEQ ID NO: 1, respectively, (ii) amino acid residues 45-53 is VLLSNPTSG, SEQ ID NO: 15, CDR 1, or amino acids 45-53 of SEQ ID NO:1, (iii) amino acid residues 54-71 thereof may have (a) at least 70%, 75%, 80%, 85%, 90% or 95% identity to the sequence of amino acid residues 54-71 of SEQ ID NO:1 or (b) may have one, two or three amino acid residues inserted or deleted relative to the sequence of amino acid residues 54-71 of SEQ ID NO:1, (iv) amino acid residues 72-79 may be YLSQNKPK, CDR 2, SEQ ID NO:16 or amino acids 72-79 of SEQ ID NO:1, (v) amino acid residues 80-117 thereof may have at least 70%, 75%, 80%, 85%, 90% or 95% identity to the sequence of amino acid residues 80-117 of SEQ ID NO:1 or may have one, two or three insertions, deletions or substitutions relative to the sequence of amino acid residues 80-117 of SEQ ID NO:1;

(vi) amino acids 118-123 may be LSNSIM, CDR 3, SEQ ID NO:17 or amino acids 80-117 of SEQ ID NO:1, (vii) amino acid residues 124-135 thereof may have at least 70%, 75%, 80%, 85%, 90% or 95% identity to the sequence of amino acid residues 124-135 of SEQ ID NO:1 or may have one, two or three insertions, deletions or substitutions relative to the sequence of amino acid residues 124-135 of SEQ ID NO:1.

The modified T cell or population of modified T cells according to the invention that express CD8 co-receptor may demonstrate improved affinity and/or avidity and/or improved T cell activation, as determinable by the assays disclosed herein, towards or on stimulation by antigenic peptide, tumour or cancer antigen optionally when presented on HLA.

According to the invention the CD8 of the modified T cell or modified T cell population may interact or bind specifically to an MHC, the MHC may be class I or class II, preferably class I major histocompatibility complex (MHC), HLA-1 molecule or with the MHC class I HLA-A/B2M dimer, preferably the CD8-$\alpha$ interacts with the $\alpha_3$ portion of the Class I MHC (between residues 223 and 229), preferably via the IgV-like domain of CD8. According to the invention the CD8 improves TCR binding of the T cell or T cell population to the HLA and/or antigenic peptide bound or presented by HLA pMHCI or pHLA, optionally on the surface of antigen presenting cell, dendritic cell and/or tumour or cancer cell, tumour or cancer tissue compared to the T cell lacking the heterologous CD8. According to the invention the CD8 may improve or increase the off-rate ($k_{off}$) of the T cell (TCR)/peptide-major histocompatibility complex class I (pMHCI) interaction of the T cell or population thereof of the invention, and hence its half-life, optionally on the surface of antigen presenting cell, dendritic cell and/or tumour or cancer cell, tumour or cancer tissue compared to the T cell lacking the heterologous CD8, and thereby may also provide improved ligation affinity and/or avidity. It may be that in this context CD8 provides an important role in organizing the TCR on the T cell surface to enable cooperativity in pHLA binding and may provide improved therapeutic avidity. According to the invention the heterologous CD8 co-receptor modified T cell or population of modified T cells may bind or interact with LCK (lymphocyte-specific protein tyrosine kinase) in a zinc-dependent manner leading to activation of transcription factors like NFAT, NF-κB, and AP-1.

A modified T cell or population of modified T cells as described herein also expresses a T cell receptor (TCR) that binds specifically to a cancer or tumour antigen or peptide thereof and/or to tumour and/or cancer cells and/or to peptides or antigenic peptides therefrom. TCRs are disulphide-linked membrane anchored heterodimeric proteins, typically comprising highly variable alpha (a) and beta (p) chains expressed as a complex with invariant CD3 chain molecules. T cells expressing these type of TCRs are referred to as $\alpha$:$\beta$ (or $\alpha\beta$) T cells. A minority of T cells express an alternative TCR comprising variable gamma ($\gamma$) and delta ($\delta$) chains and are referred to as $\gamma\delta$ T cells.

The T cell or population of T cells according to the present invention may comprise a heterologous TCR which may specifically bind and/or bind with high affinity to the cancer or tumour antigen or peptide thereof, peptide, antigenic peptide, peptide fragment of a cancer or tumour antigen or presented by tumour of cancer cell or tissue and recognised by the heterologous TCR optionally in complex with HLA. According to the invention the heterologous TCR may bind with a dissociation constant of between, 0.01 μM and 100 μM, between 0.01 μM and 50 μM, between 0.01 μM and 20 μM, between 0.05 μM and 20 μM or of 0.01, 0.02, 0.03, 0.04, 0.05, 0.06, 0.07, 0.08, 0.09, 0.1 μM, 0.15 μM, 0.2 μM, 0.25 μM, 0.3 μM, 0.35 μM, 0.4 μM, 0.45 μM, 0.5 μM, 0.55 μM, 0.6 μM, 0.65 μM, 0.7 μM, 0.75 μM, 0.8 μM, 0.85 μM, 0.9 μM, 0.95 μM, 1.0 μM, 1.5 μM, 2.0 μM, 2.5 μM, 3.0 μM, 3.5 μM, 4.0 μM, 4.5 μM, 5.0 μM, 5.5 μM, 6.0 μM, 6.5 μM, 7.0 μM, 7.5 μM, 8.0 μM, 8.5 μM, 9.0 μM, 9.5 μM, 10.0 μM; between 10 μM and 1000 μM, between 10 μM and 500 μM, between 50 μM and 500 μM or of 10, 20 30, 40, 50 60, 70, 80, 90, 100 μM, 150 μM, 200 μM, 250 μM, 300 μM, 350 μM, 400 μM, 450 μM, 500 μM; optionally measured with surface plasmon resonance, optionally at 25° C., optionally between a pH of 7.0 and 7.5. The dissociation constant, $K_D$ or $k_{off}/k_{on}$ may be determined by experimentally measuring the dissociation rate constant, $k_{off}$, and the association rate constant, $k_{on}$. A dissociation constant may be measured using a soluble form of the TCR, wherein the TCR comprises a TCR alpha chain variable domain and a TCR beta chain variable domain. Accordingly, a heterologous TCR in accordance with the invention is capable of binding efficiently and/or with high affinity to HLA displaying GVYDGREHTV for example in complex with HLA-A*02 or HLA-A*0201 for example with a dissociation constant of between 0.01 μM and 100 μM such as 50 μM, 100 μM, 200 μM, 500 μM, preferably between 0.05 μM to 20.0 μM.

According to the invention, the heterologous TCR may selectively bind to a cancer or tumour antigen or peptide thereof, peptide, antigenic peptide or peptide fragment of an antigen preferably a cancer or tumour antigen, optionally presented on HLA (pHLA), preferably expressed by a tumour cell or a cancer cell or tissue. Selective binding denotes that the heterologous TCR binds with greater affinity to one peptide, antigenic peptide or peptide fragment of an antigen preferably a cancer or tumour antigen, optionally presented on HLA (pHLA) in comparison to another. According to the present invention the binding is selective and/or specific for a cancer or tumour antigen or peptide thereof which may be a cancer-testis antigen, NY-ESO-1, MART-1 (melanoma antigen recognized by T cells), WT1 (Wilms tumor 1), gp100 (glycoprotein 100), tyrosinase, PRAME (preferentially expressed antigen in melanoma), p53, HPV-E6/HPV-E7 (human papillomavirus), HBV, TRAIL, DR4, Thyroglobin, TGFBII frameshift antigen, LAGE-1 A, KRAS, CMV (cytomegalovirus), CEA (carcinoembryonic antigen), AFP (α-fetoprotein), MAGE-A1, MAGE-A2, MAGE-A3, MAGE-A4, MAGE-A6, MAGE-A8, and MAGE-A9, MAGE-A10, or MAGE-A12. Preferably the tumour antigen is MAGE-A4. Additionally and/or alternatively the selectivity of binding may be for HLA type i.e. to HLAs corresponding to MHC class I (A, B, and C) which all are the HLA Class1 or specific alleles thereof or HLAs corresponding to MHC class II (DP, DM, DO, DQ, and DR) or specific alleles thereof, preferably the HLA is class 1, preferably the allele is HLA-A2 or HLA-A*02 or an HLA-A2+ or HLA-A*02 positive HLA, preferably HLA-*0201.

Suitable TCRs bind specifically to a major histocompatibility complex (MHC) on the surface of tumour or cancer cells that displays a peptide fragment of a tumour antigen. An MHC is a set of cell-surface proteins which allow the acquired immune system to recognise 'foreign' molecules. Proteins are intracellularly degraded and presented on the surface of cells by the MHC. MHCs displaying 'foreign' peptides, such a viral or cancer associated peptides, are recognised by T cells with the appropriate TCRs, prompting cell destruction pathways. MHCs on the surface of tumour or cancer cells may display peptide fragments of cancer or tumour antigen i.e. an antigen which is present on a tumour or cancer cell but not the corresponding non-cancer or non-tumour cell. T cells which recognise these peptide fragments may exert a cytotoxic effect on the tumour or cancer cell.

Preferably, the TCR is not naturally expressed by the T cells (i.e. the TCR is exogenous or heterologous). A Heterologous TCRs may include αβTCR heterodimers. Suitable heterologous TCRs may bind specifically to tumour or cancer cells that express a tumour or cancer antigen. For example, the T cells may be modified to express a heterologous TCR that binds specifically to MHCs displaying peptide fragments of a tumour antigen expressed by cancer cells optionally in a specific cancer patient. Tumour antigens expressed by cancer cells in the cancer patient may identified using standard techniques.

A heterologous TCR may be a recombinant or synthetic or artificial TCR i.e. a TCR that does not exist in nature. For example, a heterologous TCR may be engineered to increase its affinity or avidity for a tumour antigen (i.e. an affinity enhanced TCR). The affinity enhanced TCR may comprise one or more mutations relative to a naturally occurring TCR, for example, one or more mutations in the hypervariable complementarity determining regions (CDRs) of the variable regions of the TCR α and β chains. These mutations may increase the affinity of the TCR for MHCs that display a peptide fragment of a tumour antigen optionally when expressed by cancer cells. Suitable methods of generating affinity enhanced or matured TCRs include screening libraries of TCR mutants using phage or yeast display and are well known in the art (see for example Robbins et al J Immunol (2008) 180(9):6116; San Miguel et al (2015) Cancer Cell 28 (3) 281-283; Schmitt et al (2013) Blood 122 348-256; Jiang et al (2015) Cancer Discovery 5901).

Affinity is the strength of binding of one molecule to another for example of a TCR or T cell comprising a heterologous TCR for a cancer or tumour antigen or peptide thereof, peptide, antigenic peptide, peptide fragment of a cancer or tumour antigen or presented by tumour of cancer cell or tissue optionally when presented in complex with MHC. The binding affinity of an antigen binding protein to its target may be determined by equilibrium methods (e.g. enzyme-linked immunosorbent assay (ELISA) or radioimmunoassay (RIA)), or kinetics (e.g. BIACORE™ analysis). Avidity is the sum total of the strength of binding of two molecules to one another at multiple sites, e.g. taking into account the valency of the interaction. The T cell or population of T cells according to the present invention may demonstrate improved affinity and/or avidity to a cancer or tumour antigen or peptide thereof, peptide, antigenic peptide, peptide fragment of a cancer or tumour antigen or presented by tumour of cancer cell or tissue and recognised by the heterologous TCR in comparison or to cancer or tumour cells or tissue comprising such antigens, in comparison to the T cell or population of the T cells lacking the heterologous CD8 co-receptor.

Preferred affinity enhanced TCRs may bind to tumour or cancer cells expressing the tumour antigen MAGE A4.

A MAGEA4 TCR may comprise the α chain reference amino acid sequence of SEQ ID NO: 3 or a variant thereof and the β chain reference amino acid sequence of SEQ NO: 5 or a variant thereof. A variant may have an amino acid sequence having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity to the reference amino acid sequence. A MAGEA4 TCR may be encoded by the α chain reference nucleotide sequence of SEQ ID NO: 4 or a variant thereof and the p chain reference nucleotide sequence of SEQ NO: 6 or a variant thereof. A variant may have a nucleotide sequence having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity to the reference nucleotide sequence.

According to the present invention the TCR may comprise a TCR alpha chain variable domain and a TCR beta chain variable domain, wherein:

(i) the alpha chain variable domain comprises CDRs having the sequences

VSPFSN (αCDR1), SEQ ID NO:9 or amino acids 48-53 of SEQ ID NO:3,

LTFSEN (αCDR2), SEQ ID NO:10 or amino acids 71-76 of SEQ ID NO:3, and

CVVSGGTDSWGKLQF (αCDR3), SEQ ID NO:11 or amino acids 111-125 of SEQ ID NO:3, and (ii) the beta chain variable domain comprises CDRs having the sequences KGHDR (βCDR1), SEQ ID NO:12 or amino acids 50-54 of SEQ ID NO:5, SFDVKD (βCDR2), SEQ ID NO:13 or amino acids 68-73 of SEQ ID NO:5, and CATSGQGAYEEQFF (βCDR3), SEQ ID NO:14 or amino acids 110-123 of SEQ ID NO:5 or sequence having at least 20%, at least 25%, at least 30%, at least 40%, at least 50%, at least 60%, at least 65%, at least 70%, at least 75%, at least 80%, at least 85%, at least 90%, at least 95%, at least 98% or at least 99% sequence identity thereto, optionally 100% sequence identity thereto.

Accordingly, the TCR may comprise a TCR in which the alpha chain variable domain comprises an amino acid sequence that has at least 70%, 75%, 80%, 85%, 90%, 95%, 96%, 97%, 98% or 99% identity to SEQ ID NO:3 or the sequence of amino acid residues 1-136 of SEQ ID NO:3, and/or the beta chain variable domain comprising an amino acid sequence that has at least 70%, 75%, 80%, 85%, 90%, 95%, 96%, 97%, 98% or 99% identity to SEQ ID NO:5 or the sequence of amino acid residues 1-144 of SEQ ID NO:5.

The terms "progenitor TCR", is used herein to refer to a TCR comprising the MAGE A4 TCR α chain and MAGE A4 TCR β chain of SEQ ID NOs: 3 and 5 respectively. It is desirable to provide TCRs that are mutated or modified relative to the progenitor TCR that have an equal, equivalent or higher affinity and/or an equal, equivalent or slower off-rate for the peptide-HLA complex than the progenitor TCR. TCRs according to the invention may have more than one mutation present in the alpha chain variable domain and/or the beta chain variable domain relative to the progenitor TCR. "Engineered TCR" and "mutant TCR" are used synonymously herein and generally mean a TCR which has one or more mutations introduced relative to the progenitor TCR, in particular in the alpha chain variable domain and/or the beta chain variable domain thereof. These mutation(s) may improve the binding affinity and/or specificity and/or selectivity and/or avidity for MAGE A4. In certain embodiments, there are 1, 2, 3, 4, 5, 6, 7 or 8 mutations in alpha chain variable domain, for example 4 or 8 mutations, and/or 1, 2, 3, 4 or 5 mutations in the beta chain variable domain, for example 5 mutations. In some embodiments, the α chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues of SEQ ID NO: 7. In some embodiments, the β chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues of SEQ ID NO: 8.

According to the invention the TCR may comprise a TCR in which, the alpha chain variable domain comprises SEQ ID NO: 7 or the amino acid sequence of amino acid residues 1-136 of SEQ ID NO:7, or an amino acid sequence in which amino acid residues 1-47, 54-70, 77-110 and 126-136 thereof have at least 70%, 75%, 80%, 85%, 90%, 95%, 96%, 97%, 98% or 99% identity to the sequence of amino acid residues 1-47, 54-70, 77-110 and 126-136 respectively of SEQ ID NO:7 and/or in which amino acid residues 48-53, 71-76 and 111-125, CDR 1, CDR 2, CDR 3 respectively, have at least 70%, 75%, 80%, 85%, 90%, 95%, 96%, 97%, 98% or 99% identity to the sequence of amino acid residues 48-53, 71-76 and 111-125, CDR 1, CDR 2, CDR 3, respectively of SEQ ID NO:7.

According to the invention, the TCR may comprise a TCR in which, in the alpha chain variable domain, the sequence of:

(i) amino acid residues 1-47 thereof may have (a) at least 70%, 75%, 80%, 85%, 90% or 95% identity to the sequence of amino acid residues 1-47 of SEQ ID NO:7 or (b) may have one, two or three amino acid residues inserted or deleted relative to residues 1-47 of SEQ ID NO:7, (ii) amino acid residues 48-53 is VSPFSN, CDR 1, SEQ ID NO:9 or amino acids 48-53 of SEQ ID NO:7, (iii) amino acid residues 54-70 thereof may have (a) at least 70%, 75%, 80%, 85%, 90% or 95% identity to the sequence of amino acid residues 54-70 of SEQ ID NO: 7 or (b) may have one, two or three amino acid residues inserted or deleted relative to the sequence of amino acid residues 54-70 of SEQ ID NO: 7, (iv) amino acid residues 71-76 may be LTFSEN, CDR 2, SEQ ID NO:10 or amino acids 71-76 of SEQ ID NO:7, (v) amino acid residues 77-110 thereof may have at least 70%, 75%, 80%, 85%, 90% or 95% identity to the sequence of amino acid residues 77-110 of SEQ ID NO:7 or may have one, two or three insertions, deletions or substitutions relative to the sequence of amino acid residues 77-110 of SEQ ID NO:7, (vi) amino acids 111-125 may be CVVSGGTD-SWGKLQF, CDR 3, SEQ ID NO:11 or amino acids 111-125 of SEQ ID NO:7, (vii) amino acid residues 126-136 thereof may have at least 70%, 75%, 80%, 85%, 90% or 95% identity to the sequence of amino acid residues 126-136 of SEQ ID NO: 7 or may have one, two or three insertions, deletions or substitutions relative to the sequence of amino acid residues 126-136 of SEQ ID NO:7.

According to the invention, the TCR may comprise a TCR in which, in the beta chain variable domain comprises the amino acid sequence of SEQ ID NO:8, or an amino acid sequence in which amino acid residues 1-45, 46-50, 74-109, 124-133 thereof have at least 70%, 75%, 80%, 85%, 90% or 95% identity to the sequence of amino acid residues 1-45, 46-50, 74-109, 124-133 respectively of SEQ ID NO:8 and in which amino acid residues 46-50, 68-73 and 110-123 have at least 70%, 75%, 80%, 85%, 90% or 95% identity to the sequence of amino acid residues 46-50, 68-73 and 110-123, CDR 1, CDR 2, CDR 3, respectively of SEQ ID NO:8.

According to the invention, the TCR may comprise a TCR in which, in the beta chain variable domain, the sequence of:

(i) amino acid residues 1-45 thereof may have (a) at least 70%, 75%, 80%, 85%, 90% or 95% identity to the sequence of amino acid residues 1-45 of SEQ ID NO:8 or (b) may have one, two or three amino acid residues inserted or deleted relative to residues 1-45 of SEQ ID NO:8, (ii) amino acid residues 46-50 is KGHDR, CDR 1, SEQ ID NO:12 or amino acids 46-50 of SEQ ID NO:8, (iii) amino acid residues 51-67 thereof may have (a) at least 70%, 75%, 80%, 85%, 90% or 95% identity to the sequence of amino acid residues 51-67 of SEQ ID NO:8 or (b) may have one, two or three amino acid residues inserted or deleted relative to the sequence of amino acid residues 51-67 of SEQ ID NO:8, (iv) amino acid residues 68-73 may be SFDVKD, CDR 2, SEQ ID NO:13 or amino acids 68-73 of SEQ ID NO:8, (v) amino acid residues 74-109 thereof may have at least 70%, 75%, 80%, 85%, 90% or 95% identity to the sequence of amino acid residues 74-109 of SEQ ID NO:8 or may have one, two or three insertions, deletions or substitutions relative to the sequence of amino acid residues 74-109 of SEQ ID NO:8;

(vi) amino acids 110-123 may be CATSGQGAYEEQFF, CDR 3, SEQ ID NO:14 or amino acids 110-123 of SEQ ID NO:8, (vii) amino acid residues 124-133 thereof may have at least 70%, 75%, 80%, 85%, 90% or 95% identity to the sequence of amino acid residues 124-133 of SEQ ID NO:8 or may have one, two or three insertions, deletions or substitutions relative to the sequence of amino acid residues 124-133 of SEQ ID NO:8.

Amino acid and nucleotide sequence identity is generally defined with reference to the algorithm GAP (GCG Wisconsin Package™, Accelrys, San Diego CA). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST, psiBLAST or TBLASTN (which use the method of Altschul et al. (1990) *J. Mol. Biol.* 215: 405-410), FASTA (which uses the method of Pearson and Lipman (1988) *PNAS* USA 85: 2444-2448), or the Smith-Waterman algorithm (Smith and Waterman (1981) *J. Mol Biol.* 147: 195-197), generally employing default parameters.

Particular amino acid sequence variants may differ from a reference sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, up to 15, up to 20, up to 30 or up to 40 residues may be inserted, deleted or substituted.

In some preferred embodiments, a variant may differ from a reference sequence by 1, 2, 3, 4, 5, 6, 7, 8, 9, 10 or more conservative substitutions. Conservative substitutions involve the replacement of an amino acid with a different amino acid having similar properties. For example, an aliphatic residue may be replaced by another aliphatic residue, a non-polar residue may be replaced by another non-polar residue, an acidic residue may be replaced by another acidic residue, a basic residue may be replaced by another basic residue, a polar residue may be replaced by another polar residue or an aromatic residue may be replaced by another aromatic residue. Conservative substitutions may, for example, be between amino acids within the following groups:

(i) alanine and glycine;

(ii) glutamic acid, aspartic acid, glutamine, and asparagine (iii) arginine and lysine;

(iv) asparagine, glutamine, glutamic acid and aspartic acid (v) isoleucine, leucine and valine;

(vi) phenylalanine, tyrosine and tryptophan (vii) serine, threonine, and cysteine.

The recombinant CD8 co-receptor and/or TCR expressed in the T cells may comprise a heterologous tag at the C terminal or more preferably the N terminal. A tag is a peptide sequence which is not naturally associated with the CD8 and/or TCR and which forms one member of a specific binding pair. T cells that express the recombinant CD8 and TCR may be identified and/or purified by the binding of the other member of the specific binding pair to the tag. For example, the tag may form an epitope which is bound by an anti-tag antibody. This may be useful in identifying modified T cells during treatment.

Suitable tags include for example, $MRGS(H)_6$, DYKDDDDK (FLAG™), T7-, S-(KETAAAKFER-QHMDS), poly-Arg ($R_{5-6}$), poly-His ($H_{2-10}$), poly-Cys ($C_4$) poly-Phe($F_{11}$) poly-Asp($D_{5-16}$), SUMO tag (Invitrogen Champion pET SUMO expression system), Strept-tag II (WSHPQFEK), c-myc (EQKLISEEDL), Influenza-HA tag (Murray, P. J. et al (1995) Anal Biochem 229, 170-9), Glu-Glu-Phe tag (Stammers, D. K. et al (1991) *FEBS Lett* 283, 298-302), Tag.100 (Qiagen; 12 aa tag derived from mammalian MAP kinase 2), Cruz tag 09™ (MKAE-FRRQESDR, Santa Cruz Biotechnology Inc.) and Cruz tag 22™ (MRDALDRLDRLA, Santa Cruz Biotechnology Inc.). Known tag sequences are reviewed in Terpe (2003) Appl. Microbiol. Biotechnol. 60 523-533. In preferred embodiments, a haemagglutinin (HA) tag, such as YPYDVPDYA, may be used.

The CD8 co-receptor and TCR expressed in the modified T cell are recombinant proteins that are encoded by a heterologous nucleic acid i.e. the CD8 and TCR are expressed from encoding nucleic acid that has been incorporated into the genome of the T cell by recombinant techniques.

Modification of a T cell to express the CD8 co-receptor and TCR may comprise introducing the heterologous nucleic acid encoding the CD8 co-receptor and TCR as herein described into the T cell. Suitable methods for the introduction and expression of heterologous nucleic acids into T cells are well-known in the art and are described in more detail below.

Following introduction, a modified T cell according to the invention as described herein may comprise one or more than one copy of the heterologous nucleic acids encoding the CD8 co-receptor and TCR.

Expression of a heterologous TCR may alter the immunogenic specificity of the T cells so that they recognise or display improved recognition, specifically, selectively, with high or improved affinity or with high or improved avidity, for one or more tumour antigens that are present on the surface of the cancer cells of an individual with cancer.

In some embodiments, the T cells may display reduced binding or no binding to cancer cells in the absence of the heterologous CD8 co-receptor and TCR. For example, expression of the heterologous CD8 co-receptor and TCR may increase the affinity and/or specificity of the cancer cell binding of modified T cells relative to unmodified T cells.

The term "heterologous" refers to a polypeptide or nucleic acid that is foreign to a particular biological system, such as a host cell, and is not naturally present in that system (i.e. an exogenous polypeptide or nucleic acid). A heterologous polypeptide or nucleic acid may be introduced to a biological system by artificial means, for example using recombinant techniques. For example, heterologous nucleic acid encoding a polypeptide may be inserted into a suitable expression construct or vector preferably comprising suitable regulatory sequences capable of expressing the encoded heterologous TCR and heterologous CD8 co-receptor, which is in turn used to transform a host cell to produce the polypeptide. A heterologous polypeptide or nucleic acid may be synthetic or artificial or may exist in a different biological system, such as a different species or cell type. An endogenous polypeptide or nucleic acid is native to a particular biological system, such as a host cell, and is naturally present in that system. A recombinant polypeptide is expressed from heterologous nucleic acid that has been introduced into a cell by artificial means, for example using recombinant techniques. A recombinant polypeptide, for example heterologous TCR or heterologous CD8 co-receptor as described herein, may be identical to a polypeptide that is naturally present in the cell or may be different from the polypeptides that are naturally present in that cell or modified T cell.

T cells may be modified to express a heterologous TCR which specifically binds to a cancer or tumour antigen or peptide thereof, peptide, antigenic peptide, peptide fragment of a cancer or tumour antigen or presented by tumour of cancer cell or tissue, preferably of a cancer patient. The cancer patient may be subsequently treated with the modified T cells. Suitable cancer patients for treatment with the modified T cells may be identified by a method comprising;

obtaining sample of cancer cells from an individual with cancer and;

identifying the cancer cells as binding to the TCR expressed by the modified T cells.

Cancer or tumour cells may be identified as binding to the TCR, or heterologous TCR of the modified T cell or population thereof, by identifying one or more tumour antigens expressed by the cancer or tumour cells optionally which are determined to bind the TCR preferably by binding assay. Methods of identifying antigens on the surface of cancer or tumour cells obtained from an individual with cancer or tumour are well-known in the art.

In some embodiments, a heterologous TCR suitable for the treatment of a specific cancer patient may be identified by;

obtaining sample of cancer cells from an individual with cancer and;

identifying an antigen receptor that specifically binds to the cancer cells.

A TCR that specifically binds to the cancer cells may be identified for example by identifying one or more tumour antigens expressed by the cancer cells. Methods of identifying antigens on the surface of cancer cells obtained from an individual with cancer are well-known in the art. An TCR which binds to the one or more tumour antigens or which binds to MHC-displayed peptide fragments of the one or more antigens may then be identified, for example from TCRs of known specificities or by screening a panel or library of TCRs with diverse specificities. TCRs that specifically bind to cancer cells having one or more defined tumour antigens may be produced using routine techniques.

The T cells may be modified to express the identified TCR, or heterologous TCR, as described herein. The modified T cell or population of T cells according to the invention may be restricted by HLA specificity to HLAs corresponding to MHC class I (A, B, and C) which all are the HLA Class1 or specific alleles thereof or HLAs corresponding to MHC class II (DP, DM, DO, DQ, and DR) or specific alleles thereof, preferably the HLA is class 1, preferably the allele is HLA-A2 or HLA-A*02 or an HLA-A2+ or HLA-A*02 positive HLA, preferably HLA-A*0201.

The tumour or cancer cells of an individual suitable for treatment as described herein may express the antigen and may be of correct HLA type to bind the TCR.

Cancer or tumour cells may be distinguished from normal somatic cells in an individual by the expression of one or more antigens (i.e. cancer tumour antigens as described herein above). Normal somatic cells in an individual may not express the one or more antigens or may express them in a different manner, for example at lower levels, in different tissue and/or at a different developmental stage. Tumour antigens may elicit immune responses in the individual. In particular, a tumour antigen may elicit a T cell-mediated immune response against cancer cells in the individual that express the tumour antigen. One or more tumour antigens expressed by tumour or cancer cells in a patient may be selected as a target antigen for heterologous T cell receptors on modified T cells.

An antigen is a structure of a macromolecule which is selectively recognized by an antigen binding protein, such as for example an antibody or a TCR, and may be a cancer or tumour antigen or peptide thereof, peptide, antigenic peptide, peptide fragment of a cancer or tumour antigen or presented by tumour of cancer cell or tissue optionally in complex with MHC and optionally recognised by the heterologous TCR according to the invention. Antigens include but are not limited to protein or peptide (with or without polysaccharides) or proteic composition comprising one or more T cell epitopes, i.e. epitopes or epitope regions of the antigen, protein or peptide specifically recognised and/or bound by the CDRs of the heterologous TCR. As is contemplated herein, the target binding domains or CDRs of the TCR molecules of the present invention may recognize a sugar side chain of a glycoprotein or epitopes thereof rather than a specific amino acid sequence or of a macromolecule. Thus, the sugar moiety or sulfated sugar moiety serves as an antigen.

Tumour antigens expressed by cancer cells may include, for example, cancer-testis (CT) antigens encoded by cancer-germ line genes, such as MAGE-A4 (Simpson et al. Nature Rev (2005) 5, 615-625, Gure et al., Clin Cancer Res (2005) 11, 8055-8062; Velazquez et al., Cancer Immun (2007) 7, 1 1; Andrade et al., Cancer Immun (2008) 8, 2; Tinguely et al., Cancer Science (2008); Napoletano et al., Am J of Obstet Gyn (2008) 198, 99 e91-97).

The modification of T cells and their subsequent expansion may be performed in vitro and/or ex vivo.

T cells may be modified to express a CD8 co-receptor and TCR by the introduction of heterologous encoding nucleic acid into the T cells optionally in a vector as described herein and/or viral particle.

In some embodiments, heterologous nucleic acid encoding the CD8 co-receptor and TCR are introduced into the T cells in the same expression vector. This may be helpful in increasing the proportion of T cells which express both genes after transduction. In other embodiments, heterologous nucleic acid encoding CD8 co-receptor and TCR may be introduced into the T cells in different expression vectors.

The CD8 co-receptor and TCR may be expressed in the same transcript as a fusion protein and subsequently separated, for example using a site-specific protease. Alternatively, the CD8 co-receptor and TCR may be expressed in different transcripts.

Nucleic acid encoding a TCR and/or CD8 co-receptor may encode all the sub-units of the receptor. For example, nucleic acid encoding a TCR may comprise a nucleotide sequence encoding a TCR α chain and a nucleotide sequence encoding a TCR β chain. Nucleic acid encoding a CD8 co-receptor may comprise a nucleotide sequence encoding a CD8α chain and a nucleotide sequence encoding a CD8βchain. More preferably the nucleic acid encoding a CD8 co-receptor may comprise a nucleotide sequence encoding a CD8α chain and the CD8 co-receptor may be a CD8α homodimer.

Nucleic acid may be introduced into the T cells by any convenient method. When introducing or incorporating a heterologous nucleic acid into a T cell, certain considerations must be taken into account, well-known to those skilled in the art. The nucleic acid to be inserted should be assembled within a construct or vector which contains effective regulatory elements which will drive transcription of the encoded heterologous CD8 co-receptor and TCR in the T cell. Suitable techniques for transporting the constructor vector into the T cell are well known in the art and include calcium phosphate transfection, DEAE-Dextran, electroporation, liposome-mediated transfection and transduction using retrovirus or other virus, e.g. vaccinia or lentivirus. For example, solid-phase transduction may be performed without selection by culture on retronectin-coated, retroviral vector-preloaded tissue culture plates.

Preferably, nucleic acid encoding a CD8 co-receptor and TCR may be contained in a viral vector, most preferably a gamma retroviral vector or a lentiviral vector, such as a VSVg-pseudotyped lentiviral vector. The T cells may be transduced by contact with a viral particle comprising the nucleic acid. Viral particles for transduction may be produced according to known methods. For example, HEK293T cells may be transfected with plasmids encoding viral packaging and envelope elements as well as a lentiviral vector comprising the coding nucleic acid. A VSVg-pseudotyped viral vector may be produced in combination with the viral envelope glycoprotein G of the Vesicular stomatitis virus (VSVg) to produce a pseudotyped virus particle.

Many known techniques and protocols for manipulation and transformation of nucleic acid, for example in preparation of nucleic acid constructs, introduction of DNA into cells and gene expression are described in detail in *Protocols in Molecular Biology*, Second Edition, Ausubel et al. eds. John Wiley & Sons, 1992.

Following the introduction of nucleic acid encoding the heterologous TCR and CD8 co-receptor into the T cells, the initial population of modified T cells may be cultured in vitro such that the modified T cells proliferate and expand the population.

The modified T cell population may for example be expanded using magnetic beads coated with anti-CD3 and/or anti-CD28. The modified T cells may be cultured using any convenient technique to produce the expanded population. Suitable culture systems include stirred tank fermenters, airlift fermenters, roller bottles, culture bags or dishes, and other bioreactors, in particular hollow fibre bioreactors. The use of such systems is well-known in the art.

Numerous culture media suitable for use in the proliferation of T cells ex vivo are available, in particular complete media, such as AIM-V, Iscoves medium and RPMI-1640 (Invitrogen-GIBCO). The medium may be supplemented with other factors such as serum, serum proteins and selective agents. For example, in some embodiments, RPMI-1640 medium containing 2 mM glutamine, 10% FBS, 25 mM HEPES, pH 7.2, 1% penicillin-streptomycin, and 55 μM β-mercaptoethanol and optionally supplemented with 20 ng/ml recombinant IL-2 may be employed. The culture medium may be supplemented with the agonistic or antagonist factors described above at standard concentrations which may readily be determined by the skilled person by routine experimentation.

Conveniently, cells are cultured at 37° C. in a humidified atmosphere containing 5% $CO_2$ in a suitable culture medium.

Methods and techniques for the culture of T cells and other mammalian cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52)

In some embodiments, it may be convenient to isolate and/or purify the modified T cells from the population. Any convenient technique may be used, including FACS and antibody coated magnetic particles.

Optionally, the population of modified T cells and/or purified population of modified T cells produced as described herein may be stored, for example by lyophilisation and/or cryopreservation, before use.

A population of modified T cells may be admixed with other reagents, such as buffers, carriers, diluents, preservatives and/or pharmaceutically acceptable excipients. Suitable reagents are described in more detail below. A method described herein may comprise admixing the population of modified T cells with a pharmaceutically acceptable excipient.

Pharmaceutical compositions suitable for administration (e.g. by infusion), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents. Examples of suitable isotonic vehicles for use in such formulations include Sodium Chloride Injection, Ringer's Solution, or Lactated Ringer's Injection. Suitable vehicles can be found in standard pharmaceutical texts, for example, Remington's Pharmaceutical Sciences, 18th edition, Mack Publishing Company, Easton, Pa., 1990.

In some preferred embodiments, the modified T cells, or population of T cells, according to the invention may be formulated into a pharmaceutical composition suitable for intravenous infusion into an individual.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

An aspect of the invention provides a population of modified T cells expressing a heterologous and/or recombinant CD8 co-receptor and a heterologous and/or recombinant TCR which binds specifically to a cancer or tumour antigen or peptide thereof, peptide, antigenic peptide, peptide fragment of a cancer or tumour antigen or presented by tumour of cancer cell or tissue and recognised by the heterologous TCR and/or to tumour or cancer cells, preferably of or from an individual preferably an individual with tumour or cancer. A suitable population may be produced by a method described above.

The population of modified T cells may be for use as a medicament. For example, a population of modified T cells as described herein may be used in cancer immunotherapy therapy, for example adoptive T cell therapy.

The T cell or population of T cells according to the present invention may demonstrate an improved class I antigen response in comparison to the T cell or population of the T cells lacking the heterologous CD8 co-receptor.

The T cell or population of T cells according to the invention may demonstrate improved or increased expression of CD40L, affinity for APC or DC, cytokine production, cytotoxic activity, induction of dendritic cell maturation or induction of dendritic cell cytokine production, optionally in response to cancer or tumour antigen or peptide or cancer peptide, antigenic peptide, peptide fragment of a cancer or tumour antigen or presented by tumour of cancer cell or tissue, in comparison to the T cell or population of the T cells lacking the heterologous CD8 co-receptor The T cell or population of T cells according to the present invention may demonstrate an increased expression of CD40L and/or increased or improved affinity of for APC (antigen presenting cells) or DC (dendritic cells) and/or APC or DC which express CD40 in comparison to the T cell or population of the T cells lacking the heterologous CD8 co-receptor. The population of T cells according to the present invention may demonstrate an increased number of CD4+CD40+ T cells in the T cell population, in comparison to the T cell or population of the T cells lacking the heterologous CD8 co-receptor.

The T cell or population of T cells according to the present invention may demonstrate an increased level of T cell expansion, division or proliferation following activation in comparison to the T cell or population of the T cells lacking the heterologous CD8 co-receptor. Activation may be initiated in the presence of cytokine, interleukin, antibody, peptide or antigenic peptide, for example a cancer or tumour antigen or peptide thereof, peptide fragment of a cancer or tumour antigen recognised by the heterologous TCR or cell or tissue, for example tumour or cancer cell or tissue presenting the peptide or antigenic peptide, or peptide fragment.

The T cell or population of T cells according to the present invention may demonstrate an increased level of cytokine production in response to a cancer or tumour antigen or peptide thereof, peptide, antigenic peptide, peptide fragment of a cancer or tumour antigen or presented by tumour of cancer cell or tissue and recognised by the heterologous TCR in comparison to the T cell or population of the T cells lacking the heterologous CD8 co-receptor. The cytokine may be Granulocyte-Macrophage Colony-Stimulating Factor (GM-CSF), IFN-γ, IL-2, Tumor Necrosis Factor (TNF)-α, MIP-1β (CCL4), IL-17, IL-10, IL-4, IL-5, IL-13, IL-2 Receptor, IL-12, or MIG (CXCL9); preferably IFNγ, IL-2, TNFα, GM-CSF, or MIP1β; preferably IFNγ, IL-2, TNFα, GM-CSF, and MIP1β.

The T cell or population of T cells according to the present invention may promote improved maturation of dendritic cells in the presence of a cancer or tumour antigen or peptide thereof, peptide, antigenic peptide, peptide fragment of a cancer or tumour antigen or presented by tumour of cancer cell or tissue and recognised by the heterologous TCR in comparison to the T cell or population of the T cells lacking the heterologous CD8 co-receptor. Improved maturation may comprise increased expression of dendritic cell CD80, CD40 or HLA-DR markers.

The T cell or population of T cells according to the present invention may demonstrate an induction of an increased level of cytokine production in dendritic cells in response to a cancer or tumour antigen or peptide thereof, peptide, antigenic peptide, peptide fragment of a cancer or tumour antigen or presented by tumour of cancer cell or tissue and recognised by the heterologous TCR in comparison to the T cell or population of the T cells lacking the heterologous CD8 co-receptor. The cytokine may be Granulocyte-Macrophage Colony-Stimulating Factor (GM-CSF), IFN-γ, IL-2, Tumor Necrosis Factor (TNF)-α, MIP-1β (CCL4), IL-17, IL-10, IL-4, IL-5, IL-13, IL-2 Receptor, IL-12, or MIG (CXCL9); preferably IFN-γ, IL-12, or MIG; alternatively IFN-γ, IL-12, and MIG.

The T cell or population of T cells according to the present invention may demonstrate an induction of the production of IL-6 by dendritic cells, at a level reduced in comparison to that produced by tumour cells alone in response to a cancer or tumour antigen or peptide thereof, peptide, antigenic peptide, peptide fragment of a cancer or tumour antigen or presented by tumour of cancer cell or tissue and recognised by the heterologous TCR, optionally in comparison to the T cell or population of the T cells lacking the heterologous CD8 co-receptor.

The T cell or population of T cells according to the present invention may demonstrate improved cytotoxic activity and/or increased production levels of granzyme and/or IFN-γ in response to a cancer or tumour antigen or peptide thereof, peptide, antigenic peptide, peptide fragment of a cancer or tumour antigen or presented by tumour of cancer cell or tissue and recognised by the heterologous TCR in comparison to the T cell or population of the T cells lacking the heterologous CD8 co-receptor.

The T cell or population of T cells according to the present invention may demonstrate improved killing of tumour or cancer cells presenting a cancer or tumour antigen or peptide thereof, peptide, antigenic peptide, peptide fragment of a cancer or tumour antigen recognised by the heterologous TCR in comparison to the T cell or population of the T cells lacking the heterologous CD8 co-receptor.

According to the foregoing, the T cell or population of T cells may be or comprise CD4+, CD8+, or a mixture of CD4+ and CD8+ T cells.

Adoptive cellular therapy or adoptive immunotherapy refer to the adoptive transfer of human T lymphocytes or NK lymphocytes that are engineered by gene transfer to express genetically modified TCRs and/or co-receptors (e.g. CD8), specific for surface antigens or peptide MHC complexes expressed on target cells. This can be used to treat a range of diseases depending upon the target chosen, e.g., tumour or cancer specific antigens to treat cancer or tumour. Adoptive cellular therapy involves removing a portion of a donor's or the patient's white blood cells using a process called leukapheresis. The T cells or NK cells may then be expanded and mixed with expression vectors comprising the TCR polynucleotide and/or co-receptor (e.g. CD8), in order to transfer the TCR and/or co-receptor (e.g. CD8) to the T cells or NK cells. The T cells or NK cells are expanded again and at the end of the expansion, the engineered T cells or NK cells are washed, concentrated, and then frozen to allow time for testing, shipping and storage until a patient is ready to receive the infusion of engineered cells.

Other aspects of the invention provide the use of a population of modified T cells as described herein for the manufacture of a medicament for the treatment of cancer and/or tumour, a population of modified T cells as described herein for the treatment of cancer and/or tumour, and a method of treatment of cancer and/or tumour which may comprise administering a population of modified T cells as described herein to an individual in need thereof.

The population of modified T cells may be autologous i.e. the modified T cells were originally obtained from the same individual to whom they are subsequently administered (i.e. the donor and recipient individual are the same). A suitable population of modified T cells for administration to the individual may be produced by a method comprising providing an initial population of T cells obtained from the individual, modifying the T cells to express a CD8 co-receptor and a TCR which binds specifically to tumour or cancer cells or to a cancer or tumour antigen or peptide thereof, peptide, antigenic peptide, peptide fragment of a cancer or tumour antigen or presented by tumour of cancer cell or tissue and recognised by the heterologous TCR in the individual, and culturing the modified T cells.

The population of modified T cells may be allogeneic i.e. the modified T cells were originally obtained from a different individual to the individual to whom they are subsequently administered (i.e. the donor and recipient individual are different). Allogeneic refers to a graft derived from a different animal of the same species.

The donor and recipient individuals may be HLA matched to avoid GVHD and other undesirable immune effects. A suitable population of modified T cells for administration to a recipient individual may be produced by a method comprising providing an initial population of T cells obtained from a donor individual, modifying the T cells to express a CD8 co-receptor and a TCR which binds specifically to tumour or cancer cells or to a cancer or tumour antigen or peptide thereof, peptide, antigenic peptide, peptide fragment of a cancer or tumour antigen or presented by tumour of cancer cell or tissue and recognised by the heterologous TCR in the recipient individual, and culturing the modified T cells.

Following administration of the modified T cells, the recipient individual may exhibit a T cell mediated immune response against tumour or cancer cells or tissues optionally which present a cancer or tumour antigen or peptide thereof, peptide, antigenic peptide, peptide fragment of a cancer or tumour antigen or presented by tumour of cancer cell or tissue and recognised by the heterologous TCR in the recipient individual. This may have a beneficial effect on the cancer condition in the individual.

As used herein, the terms "cancer," "neoplasm," and "tumour" are used interchangeably and, in either the singular or plural form, refer to cells that have undergone a malignant transformation that makes them pathological to the host organism.

Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumour, a "clinically detectable" tumour is one that is detectable on the basis of tumour mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient.

Cancer conditions, including cancer conditions or cancer which may be treated according to the present invention, may be characterised by the abnormal proliferation of malignant cancer cells and may include leukaemias, such as AML, CML, ALL and CLL, lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer, as well as cancer of unknown primary (CUP).

In some preferred embodiments, a cancer, including cancer conditions or cancer which may be treated according to the present invention, may be a haematopoietic (or haematologic or haematological or blood-related) cancer, for example, cancers derived from blood cells or immune cells, which may be referred to as "liquid tumours." Specific examples of clinical conditions based on haematologic tumours include leukaemias, such as chronic myelocytic leukaemia, acute myelocytic leukaemia, chronic lymphocytic leukaemia and acute lymphocytic leukaemia; plasma cell malignancies such as multiple myeloma, MGUS and Waldenstrom's macroglobulinemia; lymphomas, such as non-Hodgkin's lymphoma, Hodgkin's lymphoma; and the like. The cancer may be any cancer in which an abnormal number of blast cells or unwanted cell proliferation is present or that is diagnosed as a haematological cancer, including both lymphoid and myeloid malignancies. Myeloid malignancies include, but are not limited to, acute myeloid (or myelocytic or myelogenous or myeloblastic) leukaemia (undifferentiated or differentiated).

Cancer cells within an individual may be immunologically distinct from normal somatic cells in the individual (i.e. the cancerous tumour may be immunogenic). For example, the cancer cells may be capable of eliciting a systemic immune response in the individual against one or more antigens expressed by the cancer cells. The tumour antigens that elicit the immune response may be specific to cancer cells or may be shared by one or more normal cells in the individual.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

In some embodiments, the individual may have minimal residual disease (MRD) after an initial cancer treatment.

An individual with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual.

An anti-tumour effect for example which may be associated with the population of modified T cells, the pharmaceutical composition, methods of treatment or the population of modified T cells for use in therapy, according to the invention, is a biological effect which can be manifested by a reduction in the rate of tumour growth, decrease in tumour volume, a decrease in the number of tumour cells, a decrease in the number of metastases, an increase in life expectancy, or amelioration of various physiological symptoms associated with the cancerous condition. This may be measured in vivo or in vitro optionally in comparison to a control or control individual comprising treatment with vehicle or no treatment or comprising treatment with a population of T cells lacking the CD8 co-receptor. An "anti-tumour effect" can also be manifested by the ability of the peptides, polynucleotides, cells and antibodies, modified T cell or population of modified T cells as described herein in prevention of the occurrence of tumour in the first place, for example as a prophylactic treatment. An anti-tumour effect may be determined by measurement of improved TTP (time to progression), OS (Overall Survival), or PFS (Progression Free Survival) of a treated individual for example in comparison to a control or control individual as described herein-before.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment or for example in comparison to a control or control individual as described herein-before, for example as measured by improved TTP (time to progression), OS (Overall Survival), or PFS (Progression Free Survival).

Treatment may also be prophylactic (i.e. prophylaxis). For example, an individual susceptible to or at risk of the occurrence or re-occurrence of cancer may be treated as described herein. Such treatment may prevent or delay the occurrence or re-occurrence of cancer in the individual, optionally for example in comparison to a control or control individual as described herein-before.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of T cells, and a decrease in levels of tumour-specific antigens. Administration of T cells modified as described herein may improve the capacity of the individual to resist cancer growth, in particular growth of a cancer already present the subject and/or decrease the propensity for cancer growth in the individual.

The modified T cells or the pharmaceutical composition comprising the modified T cells may be administered to a subject by any convenient route of administration, whether systemically/peripherally or at the site of desired action, including but not limited to; parenteral, for example, by infusion, intravenously or subcutaneously. Infusion involves the administration of the T cells in a suitable composition through a needle or catheter. Typically, T cells are infused intravenously or subcutaneously, although the T cells may be infused via other non-oral routes, such as intramuscular injections and epidural routes. Suitable infusion techniques are known in the art and commonly used in therapy (see, e.g., Rosenberg et al., New Eng. J. of Med., 319:1676, 1988).

Typically, the number of cells administered is from about 105 to about $10^{10}$ per Kg body weight, typically $2\times10^8$ to $2\times10^{10}$ cells per individual, typically over the course of 30 minutes, with treatment repeated as necessary, for example at intervals of days to weeks. It will be appreciated that appropriate dosages of the modified T cells, and compositions comprising the modified T cells, can vary from patient to patient.

Determining the optimal dosage will generally involve the balancing of the level of therapeutic benefit against any risk or deleterious side effects of the treatments of the present invention. The selected dosage level will depend on a variety of factors including, but not limited to, the activity of the particular cells, the route of administration, the time of administration, the rate of loss or inactivation of the cells, the duration of the treatment, other drugs, compounds, and/or materials used in combination, and the age, sex, weight, condition, general health, and prior medical history of the patient. The amount of cells and the route of administration will ultimately be at the discretion of the physician, although generally the dosage will be to achieve local concentrations at the site of action which achieve the desired effect without causing substantial harmful or deleterious side-effects.

While the modified T cells may be administered alone, in some circumstances the modified T cells may be administered cells in combination with the target antigen, APCs displaying the target antigen, and/or IL-2 to promote expansion in vivo of the population of modified T cells.

The population of modified T cells may be administered in combination, optionally separately, sequentially or simultaneously, with one or more other therapies, such as cytokines e.g. IL-2, cytotoxic chemotherapy, radiation and immuno-oncology agents, including checkpoint inhibitors, such as anti-B7-H3, anti-B7-H4, anti-TIM3, anti-KIR, anti-LAG3, anti-PD-1, anti-PD-L1, and anti-CTLA4 antibodies.

According to the present invention, a modified T cell or a population of modified T cells may further comprise and/or express at least one exogenous and/or recombinant co-stimulatory ligand, optionally one, two, three or four. The interaction between the TCR and at least one exogenous co-stimulatory ligand may provide a non-antigen-specific signal and activation of the cell. Co-stimulatory ligands include, but are not limited to, members of the tumour necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type 11 transmembrane proteins (extracellular C-terminus) containing a short cytoplasmic segment and a relatively long extracellular region. TNF superfamily members include, but are not limited to, nerve growth factor (NGF), CD40L (CD40L)/CDl54, CD137L/4-1BBL, TNF-alpha, CD134L/OX40L/CD252, CD27L/CD70, Fas ligand (FasL), CD30L/CD153, tumour necrosis factor beta (TNFP)/lymphotoxin-alpha (LTa),lymphotoxin-beta (TTb), CD257/B cell-activating factor (BAFF)/Blys/THANK/Tall-, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28. In certain embodiments, the at least one co-stimulatory ligand is selected from the group consisting of 4-1 BBL, CD275, CD80, CD86, CD70, OX40L, CD48, TNFRSF14, and combinations thereof. According to the present invention the modified T cell or a population of modified T cells may further comprise at least one exogenous and/or recombinant co-stimulatory ligand can be 4-1 BBL or CD80, preferably 4-1 BBL, alternatively 4-1 BBL and CD80.

The one or more other therapies may be administered by any convenient means or therapeutic route as described herein, preferably at a site which is separate from the site of administration of the modified T cells.

Administration of modified T cells can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. Preferably, the modified T cells are administered in a single transfusion optionally of a least $1 \times 10^9$ T cells. Typically, the number of cells administered is from about $10^5$ to about $10^{10}$ per Kg body weight, typically $2 \times 10^8$ to $2 \times 10^{10}$ cells per individual, typically over the course of 30 minutes, with treatment repeated as necessary, for example at intervals of days to weeks. It will be appreciated that appropriate dosages of the cells, the amount of cells and the route of administration will ultimately be at the discretion of the physician.

Other aspects of the invention provide nucleic acids and other reagents for the generation of modified T cells as described herein.

An isolated nucleic acid according to the invention may comprise a nucleotide sequence encoding a TCR which binds specifically to cancer cells or to a cancer or tumour antigen or peptide thereof, peptide, antigenic peptide, peptide fragment of a cancer or tumour antigen or presented by tumour of cancer cell or tissue and a nucleotide sequence encoding a CD8 co-receptor, preferably the TCR binds specifically to MAGE-A4.

The coding sequences may be operably linked to the same or different promoters or other regulatory elements. Suitable regulatory elements or promoters are well known in the art and include mammalian promoters, such as Human elongation factor-1 alpha (EF1α). In some embodiments, the coding sequences may be separated by a cleavage recognition sequence. This allows the CD8 co-receptor and TCR to be expressed as a single fusion which undergoes intracellular cleavage by a site specific protease, such as furin, to generate the two separate proteins. Suitable cleavage recognition sequences include 2A-furin sequence.

The nucleotide sequences encoding the CD8 co-receptor and TCR may be located in the same expression vector. For example, a suitable expression vector may comprise a nucleic acid as described above. Alternatively, the coding sequences may be located in separate expression vectors.

Suitable vectors are well known in the art and are described in more detail above.

Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication, promoter regions and selectable markers, which allow for its selection, expression and replication in bacterial hosts such as *E. coli*. Preferred vectors include retroviral vectors, such as lentiviral vectors, including VSVg-pseudotyped self-inactivating vectors.

A viral vector, such as a lentivirus, may be contained in a viral particle comprising the nucleic acid vector encapsulated by one or more viral proteins. A viral particle may be produced by a method comprising transducing mammalian cells with a viral vector as described herein and one or more viral packaging and envelope vectors and culturing the transduced cells in a culture medium, such that the cells produce viral or lentiviral particles that are released into the medium, optionally the viral or lentiviral particles are purified.

Following release of viral particles, the culture medium comprising the viral particles may be collected and, optionally the viral particles may be concentrated.

Following production and optional concentration, the viral particles may be stored, for example by freezing at −80° C. ready for use in transducing T cells.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the methods of the disclosure, exemplary compositions and methods are described herein. Any of the aspects and embodiments of the disclosure described herein may also be combined. For example, the subject matter of any dependent or independent claim disclosed herein may be multiply combined (e.g., one or more recitations from each dependent claim may be combined into a single claim based on the independent claim on which they depend).

Ranges provided herein include all values within a particular range described and values about an endpoint for a particular range. The figures and tables of the disclosure also describe ranges, and discrete values, which may constitute an element of any of the methods disclosed herein. Concentrations described herein are determined at ambient temperature and pressure. This may be, for example, the temperature and pressure at room temperature or in within a particular portion of a process stream.

Preferably, concentrations are determined at a standard state of 25° C. and 1 bar of pressure. The term "about" means a value within two standard deviations of the mean for any particular measured value.

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The present invention further provides the following aspects:

1. A modified T cell or population of modified T cells comprising a heterologous co-receptor and a heterologous T cell receptor (TCR), optionally wherein the TCR and co-receptor are recombinant, optionally wherein the co-receptor is a CD8 co-receptor.

2. The modified T cell or population of modified T cells of aspect 1, wherein the heterologous TCR binds or specifically binds to a cancer or tumour antigen or peptide thereof.

3. The modified T cell or population of modified T cells of aspect 1, wherein the heterologous TCR binds or specifically binds to a peptide, peptide antigen or antigenic peptide, optionally associated with a cancerous condition or binds to a peptide or peptide fragment of a cancer or tumour antigen optionally presented by tumour of cancer cell or tissue.

4. The modified T cell or population of modified T cells of either of aspects 2 or 3, wherein the peptide, peptide antigen, antigenic peptide or peptide fragment is complexed with a peptide presenting molecule, optionally major histocompatibility complex (MHC) or human leukocyte antigen (HLA), optionally class I or class II, optionally wherein the peptide is complexed with HLA-A2 or HLA-A*02, or HLA-A*0201.

5. The modified T cell or population of modified T cells of any previous aspect, wherein the heterologous TCR binds to a peptide, peptide antigen, antigenic peptide or peptide fragment a cancer or tumour antigen or peptide thereof which is a cancer-testis antigen.

6. The modified T cell or population of modified T cells of any previous aspect, wherein the heterologous TCR binds to any of NY-ESO-1, MART-1 (melanoma antigen recognized by T cells), WT1 (Wilms tumor 1), gp100 (glycoprotein 100), tyrosinase, PRAME (preferentially expressed antigen in melanoma), p53, HPV-E6/HPV-E7 (human papillomavirus), HBV, TRAIL, DR4, Thyroglobin, TGFBII frameshift antigen, LAGE-1 A, KRAS, CMV (cytomegalovirus), CEA (carcinoembryonic antigen), AFP (α-fetoprotein), MAGE-A1, MAGE-A2, MAGE-A3, MAGE-A4, MAGE-A6, MAGE-A8, and MAGE-A9, MAGE-A10, or MAGE-A12, or peptide thereof.

7. The modified T cell or population of modified T cells of any previous aspect, wherein the heterologous TCR binds to the tumour antigen MAGE-A4 or peptide thereof, preferably to the sequence GVYDGREHTV (SEQ ID NO: 18).

8. The modified T cell or population of modified T cells of any of aspects 2 to 7, wherein the heterologous TCR binds specifically and/or selectively to the cancer or tumour antigen or peptide thereof and/or the peptide presenting molecule.

9. The modified T cell or population of modified T cells of any previous aspect, wherein the heterologous CD8 co-receptor is heterodimer or homodimer, a CD8αβ heterodimer or a CD8αα homodimer.

10. The modified T cell or population of modified T cells of any previous aspect, wherein the heterologous CD8 co-receptor comprises;

(a) a CDR 1 of at least 80% sequence identity to amino acid sequence VLLSNPTSG, SEQ ID NO:15, CDR 2 of at least 80% sequence identity to amino acid sequence YLSQNKPK SEQ ID NO:16 and CDR 3 of at least 80% sequence identity amino acid sequence LSNSIM SEQ ID NO:17, (b) a CDR 1 of amino acid sequence VLLSNPTSG, SEQ ID NO:15, CDR 2 of amino acid sequence YLSQNKPK SEQ ID NO:16 and CDR 3 of amino acid sequence LSNSIM SEQ ID NO:17, (c) an amino acid sequence having at least 80% sequence identity to SEQ ID NO: 1, or (d) an amino acid sequence having the sequence of SEQ ID NO: 1.

11. The modified T cell or population of modified T cells of any previous aspect, wherein the heterologous TCR comprises a TCR alpha chain variable domain and a TCR beta chain variable domain, wherein:

(i) the alpha chain variable domain comprises CDRs having the sequences

VSPFSN (αCDR1), SEQ ID NO:9 or amino acids 48-53 of SEQ ID NO:3,

LTFSEN (αCDR2), SEQ ID NO:10 or amino acids 71-76 of SEQ ID NO:3, and

CVVSGGTDSWGKLQF (αCDR3), SEQ ID NO:11 or amino acids 111-125 of SEQ ID NO:3, and (ii) the beta chain variable domain comprises CDRs having the sequences KGHDR (βCDR1), SEQ ID NO:12 or amino acids 50-54 of SEQ ID NO:5, SFDVKD (βCDR2), SEQ ID NO:13 or amino acids 68-73 of SEQ ID NO:5, and CATSGQGAYEEQFF (βCDR3), SEQ ID NO:14 or amino acids 110-123 of SEQ ID NO:5 or sequence having at least 80% sequence identity thereto.

12. The modified T cell or population of modified T cells of any previous aspect, wherein the heterologous TCR comprises a TCR in which the alpha chain variable domain comprises an amino acid sequence that has at least 80%, identity to SEQ ID NO:3 and/or the beta chain variable domain comprising an amino acid sequence that has at least 80% identity to SEQ ID NO:5.

13. The modified T cell or population of modified T cells of any previous aspect, wherein T cell is CD4+ or CD8+ and/or the population of T cells comprises CD4+, CD8+, or a mixture of CD4+ and CD8+ T cells.

14. The modified T cell or population of modified T cells of any previous aspect, wherein the modified T cell or population of modified T cells has an improved or increased expression of CD40L, cytokine production, cytotoxic activity, induction of dendritic cell maturation or induction of dendritic cell cytokine production, optionally in response to cancer or tumour antigen or peptide or cancer peptide, antigenic peptide, peptide fragment of a cancer or tumour antigen or presented by tumour of cancer cell or tissue, in comparison to the T cell or population of the T cells lacking the heterologous CD8 co-receptor.

15. A nucleic acid encoding the heterologous TCR and heterologous co-receptor according to any of the preceding aspects.

16. A nucleic acid of aspect 15 wherein the nucleic acid comprises a first nucleotide sequence encoding the heterologous co-receptor and a second nucleotide sequence encoding the heterologous TCR.

17. A vector comprising the nucleic acid of either of aspects 15 or 16, optionally wherein the vector is an expression vector, further optionally comprising regulatory elements for the expression of the encoded heterologous TCR and heterologous co-receptor of the nucleic acid.

18. A vector of aspect 17 comprising the nucleic acid of aspect 16, wherein the first nucleotide sequence is in a single open reading frame or in two distinct open reading frames encoding the TCR alpha chain and the TCR beta chain respectively and wherein the second nucleotide sequence is in a single open reading or in two distinct open reading frames encoding the co-receptor alpha chain and the co-receptor beta chain respectively or co-receptor alpha chain and the co-receptor alpha chain respectively.

19. A virus particle comprising the nucleic acid of aspects 15 or 16 or a vector of aspects 17 or 18.

20. The modified T cell or population of modified T cells according to aspects 1 to 14 comprising the nucleic acid of aspect 15 or 16 or vector of aspect 17 or 18.

21. The modified T cell or population of modified T cells of any one aspects 1 to 14 or 20 which further comprises one or more exogenous or recombinant co-stimulatory ligand.

22. A method of making the modified T cell or population of modified T cells of any one of aspects 1 to 14 comprising introducing one or more than one copy of the nucleic acid of either of aspects 15 or 16 or vector of either of aspects 17 to 18 into a T cell or population of T cells, optionally wherein the nucleic acid or vector is comprised within a viral particle of aspect 19, optionally comprising additionally introducing into the T cell or T cell population nucleic acid encoding the one or more exogenous or recombinant co-stimulatory ligand or vector comprising said nucleic acid.

23. The method of aspect 22 further comprising culturing the modified T cell or population of modified T cells in vitro such that the modified T cell or cells or population thereof proliferate and/or expand the population and optionally subsequently to isolate and/or purify the modified T cells of the population.

24. A pharmaceutical composition comprising the modified T cell or population of modified T cells of any one of aspects 1 to 14, 20 or 21, nucleic acid of either of aspects 15 or 16, vector of either of aspects 17 or 18, or virus particle of aspect 19, together with one or more pharmaceutically acceptable carrier or excipient.

25. The modified T cell or population of modified T cells of any one of aspects 1 to 14, 20 or 21, nucleic acid of either of aspects 15 or 16, vector of either of aspects 17 or 18, virus particle of aspect 19, or pharmaceutical composition of aspect 24 for use in medicine.

26. The modified T cell or population of modified T cells of any one of aspects 1 to 14, 20 or 21, nucleic acid of either of aspects 15 or 16, vector of either of aspects 17 or 18, virus particle of aspect 19, or pharmaceutical composition of aspect 24 for use in the treatment of cancer and/or tumour optionally wherein the treatment is cancer immunotherapy therapy and/or adoptive T cell therapy, optionally autologous or allogenic adoptive T cell therapy.

27. A method of treating cancer and/or tumour in an individual comprising administering to the individual the modified T cell or population of modified T cells of any one of aspects 1 to 14, 20 or 21, nucleic acid of either of aspects 15 or 16, vector of either of aspects 17 or 18, virus particle of aspect 19, or pharmaceutical composition of aspect 24, optionally wherein the treatment is cancer immunotherapy therapy and/or adoptive T cell therapy, optionally autologous or allogenic adoptive T cell therapy.

28. Use of the modified T cell or population of modified T cells of any one of aspects 1 to 14, 20 or 21, nucleic acid of either of aspects 15 or 16, vector of either of aspects 17 or 18, virus particle of aspect 19, or pharmaceutical composition of aspect 24, in the manufacture of a medicament for the treatment of cancer and/or tumour, optionally wherein the treatment is cancer immunotherapy therapy and/or adoptive T cell therapy, optionally autologous or allogenic adoptive T cell therapy.

29. The modified T cell or population of modified T cells of any one of aspects 1 to 14, 20 or 21, nucleic acid of either of aspects 15 or 16, vector of either of aspects 17 or 18, virus particle of aspect 19, pharmaceutical composition of aspect 24, use according to aspect 26, method of aspect 27 or use of aspect 28, wherein the cancer is a solid tumour.

30. The modified T cell or population of modified T cells of any one of aspects 1 to 14, 20 or 21, nucleic acid of either of aspects 15 or 16, vector of either of aspects 17 or 18, virus particle of aspect 19, pharmaceutical composition of aspect 24, use according to aspect 26, method of aspect 27 or use of aspect 28 or 29, wherein the cancer is selected from any one of synovial sarcoma, myxoid/round cell liposarcoma (MRCLS), head and neck cancer, head and neck SCC (squamous cell carcinoma), melanoma, esophageal cancer, ovarian cancer, gastric cancer (stomach), bladder cancer, lung cancer, non-small cell lung NSCLC (squamous, adenocarcinoma, adenosquamous, large cell carcinoma), metastatic or advanced NSCLC, urothelial cancer or tumour, esophagogastric junction cancer (EGJ), optionally wherein the cancer or tumour express a MAGE protein or peptide, optionally MAGE-A4 protein or peptide.

31. The modified T cell or population of modified T cells of any one of aspects 1 to 14, 20 or 21, nucleic acid of either of aspects 15 or 16, vector of either of aspects 17 or 18, virus particle of aspect 19, pharmaceutical composition of aspect 24, use according to aspect 26, method of aspect 27 or use of aspect 28 or 29, wherein the cancer is selected from any one of liver cancer, pancreatic cancer, colorectal cancer, lung cancer, metastatic stomach cancer, metastatic gastric cancer, metastatic liver cancer, metastatic ovarian cancer, metastatic pancreatic cancer, metastatic colorectal cancer, metastatic lung cancer, colorectal carcinoma or adenocarcinoma, lung carcinoma or adenocarcinoma, pancreatic carcinoma or adenocarcinoma, mucinous adenoma, ductal carcinoma of the pancreas.

32. The modified T cell or population of modified T cells of aspects 1 to 14, 20 or 21, nucleic acid of aspect 15 or 16, vector of aspect 17 or 18, virus particle of aspect 19, pharmaceutical composition of aspect 24, use according to aspect 26, method of aspect 27 or use of aspect 28 or 29, wherein the wherein the modified T cell or population of modified T cells, nucleic acid, vector, virus particle, or pharmaceutical is for use or used in combination with one or more further therapeutic agent optionally administered or for administration separately, sequentially or simultaneously.

The invention is further described in the following non-limiting examples and by reference to the following Figures.

EXAMPLES

Figure 1:
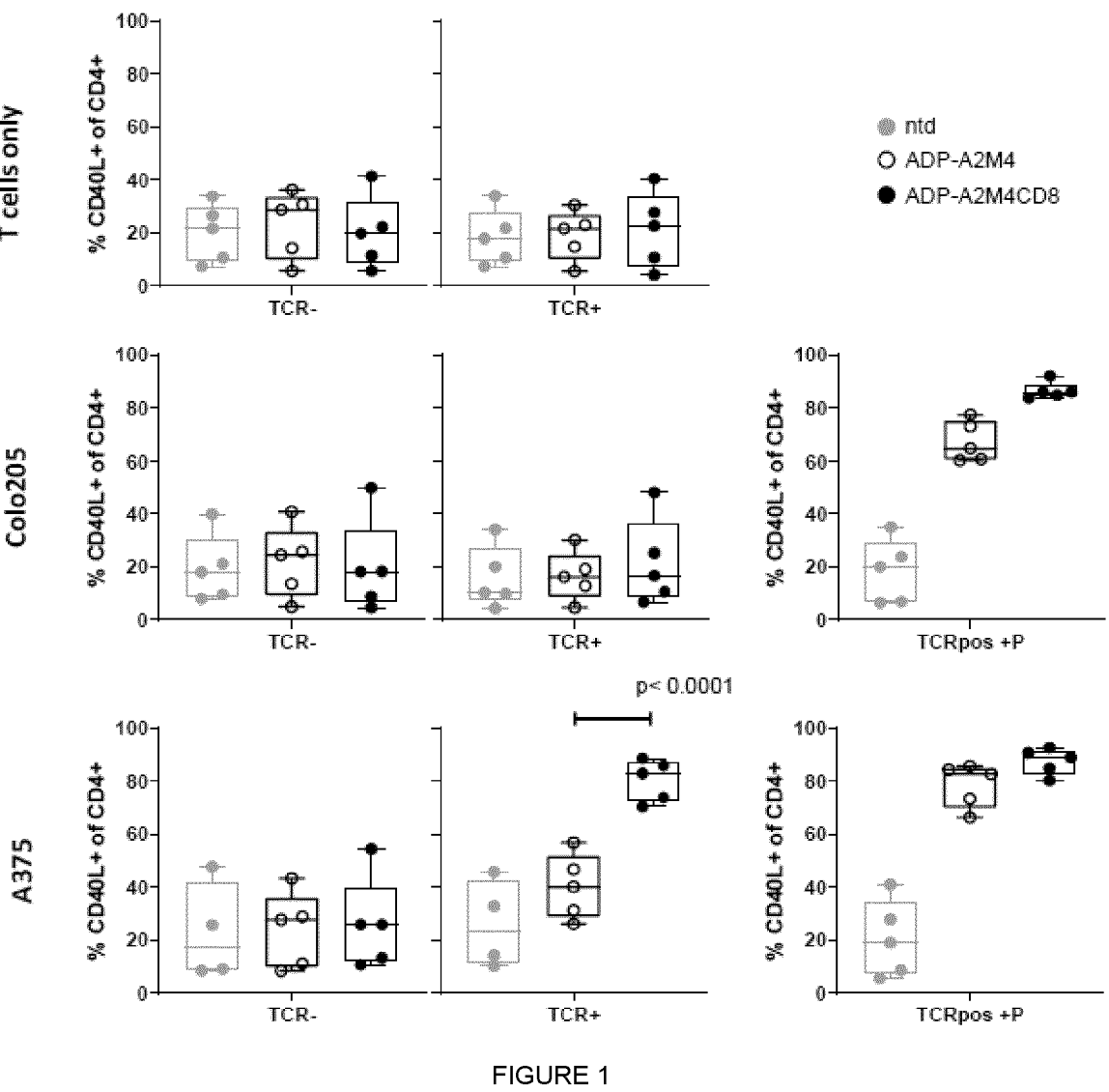
FIG. 1. Frequency of CD40L+ cells within the CD4+ T cell subset. The frequency of CD40L+ T cells was determined in the TCR negative (TCR−) and TCR positive (TCR+) subsets of the CD4+ T cell population in unstimulated T cells (T cells only), stimulation with antigen negative target cells (Colo205) or antigen positive target cells (A375). Peptide-pulsed (+P) target cells served as controls (right-hand side graphs). Box and whisker plots summarize the data for all five Wave products tested, within these each individual data point represents one Wave product. Statistical significance was assessed using R with a 3-way repeated-measures ANOVA, with subset (i.e. CD4/8), TCR+/−, and transduction level as within-subject factors followed by pairwise post-hoc tests for each combination of transduction within a subset/TCR combination and p values adjusted using the Holm method.

In this second-generation TCR study, we added a CD8α homodimer to the specific peptide enhanced affinity receptor (SPEAR) MAGE-A4$^{c1032}$ TCR (MAGE-A4 TCR herein), a first generation TCR currently being tested in a clinical trial (NCT03132922).

Transduction of HLA class I-restricted, specific peptide enhanced affinity receptor (SPEAR) TCRs into peripheral blood lymphocytes creates both cytotoxic (CD8+) and helper (CD4+) T-cells of the same specificity; however, the lack of CD8 co-receptors on CD4+ T-cells may affect binding avidity of the engineered TCR. The addition of CD8α co-receptor into CD4+ T-cells alongside the engineered TCR CD8α_MAGE-A4$^{c1032}$ (CD8α_MAGE-A4 herein) was anticipated to increase TCR binding avidity and enhance the polyfunctional response of CD4+ T-cells against tumor antigens, thereby widening the immune response to the tumor through dendritic cell (DC) activation and enhanced cytotoxicity.

Example 1. Preparation of Modified T Cells

The intention of the following experiments was to investigate whether the stability of the TCR interaction with HLA class I and peptide antigen complex in transduced helper CD4+ T cells would be aided through the presence of CD8 co-receptor, commonly present on cytotoxic T cells, and thereby provide improved CD4+ T cell function in response to Class I antigens and enhance the polyfunctional response of CD4+ T cells against tumour antigens.

Human T cells were lentivirally transduced to constitutively co-express an affinity-enhanced MAGE-A4 TCR, [SEQ ID NO: 3 and 5], which recognises the HLA-A*02: 01-restricted MAGE-A4 peptide GVYDGREHTV and the cluster of differentiation CD8α (homodimer) co-receptor [SEQ ID NO: 1]. Control T cells were also provided which lacked the CD8α.

Lentiviral particles encoding the enhanced-affinity TCR, with or without CD8α, were produced by transient transfection of HEK293T/17 cells. HEK293T/17 cells were seeded 48-72 hours prior to transfection in 5-layer cell factories, to ensure 60-80% confluency when they were co-transfected with a single lentiviral transgene plasmid (encoding the TCR, with or without CD8α) and a set of complimentary lentiviral packaging plasmids. Replication-deficient lentiviral particles were produced over a 48-72 hour period, which were harvested from the supernatant, concentrated via centrifugation and cryopreserved. Lentiviral biological titre determination was performed to provide optimum transduction efficiencies and provide the volume of lentiviral vector required to give a Multiplicity of Infection (MOI) of ~1 for T cell transduction.

'Wave' T cells were obtained for transduction through addition of the high-titre lentiviral suspension and expanded. For the 'Wave' expansions, CD3+ T cells were isolated and stimulated using CD3/CD28 antibody-coated microbeads (Dynabeads CTS, Life Technologies) from cryopreserved healthy human donor leukopaks (enriched leukapheresis products collected from normal peripheral blood). The CD3+ cells were expanded using the 'Wave' platform (Xuri Cell Expansion System, GE Healthcare Life Sciences) to provide a T cell product.

The large-scale 'Wave' T cells were obtained from human PBMCs. A leukopak containing 2.0-2.5×10⁹ human PBMCs was thawed, CD3+ T cells were isolated using CD3/CD28 antibody coated microbeads and VueLife bags were seeded with CD3+ cells. For each donor, several VueLife bags were seeded: three to produce non-transduced (ntd) T cells, three to produce the MAGE-A4 TCR alone, two to produce T cells transduced with the CD8α_MAGE-A4 TCR. Subsequently the CD3+ cells were transduced with the appropriate volume of lentiviral vector to give an MOI of 1. Following a growth period the cells were washed and placed in to a new VueLife bag. Cell count was monitored daily and the volume of media in increased as required up to a maximum of 500 mL. The cells were transferred to a Wave bag and Xuri Cell Expansion System once all conditions were above $150 \times 10^6$ cells. Thereafter the expanded T cells were harvested from the WAVE bags, T cells were washed and pooled. Beads were removed from the cells, followed by harvesting, washing and cryopreservation in multiple aliquots for later analysis.

For some experiments it was necessary to have separated CD4+ or CD8+ cells purified from the T cell product. The cell separation procedure was carried out on the day of cryopreservation, yielding assay-ready pre-separated vials. The CD8+ cell population was negatively selected through depletion of CD4+ cells. The Miltenyi Biotec CD4 microbeads were used for this purpose according to the manufacturer's instructions. The CD4+ cell population were negatively selected for with a CD83 antibody that only binds native CD8 cells with $\alpha/\beta$ CD8 heterodimer. In short $1.0 \times 10^7$ T cells were incubated with 5 µg of mouse anti-human CD83 antibody (clone 3TU9618, Creative Diagnostics) for 30 minutes at 4° C. (quantities scaled as required). Upon single wash cycle anti-mouse IgG microbeads (Miltenyi) were used according to manufacturer's protocol to negatively select an unbound fraction on LD columns (Miltenyi). The purity of resulting fractions was determined by flow cytometry.

Measures were made of T cell activation as follows, with a focus on CD4 cells, determining CD40L activation, cytokine release and direct killing of target cells and by investigating the interaction between T cells and dendritic cells.

Example 2. Assessment of CD40L Surface Expression Following Stimulation

CD40 ligand (CD40L, also known as CD154) is a member of the TNF family. It is primarily expressed on activated T cells, preferentially CD4+ T cells. It acts as a co-stimulatory molecule which binds CD40 on antigen presenting cells (APCs), which most importantly in this context licenses those APCs to activate antigen specific naïve CD8+ T cells.

Surface expression of CD40L was analysed on Wave T cells following overnight stimulation. For this $0.1 \times 10^6$ target cells were seeded into a 96-well flat bottom plate on day zero and left to adhere overnight at 37° C. and 5% $CO_2$. A375 cells were used as an antigen positive target cell line, and Colo205 as an antigen negative target cell line. On day 1 T cells were added at an Effector:Target ratio of 5:1 ($0.5 \times 10^6$ cells/well) along with an anti-CD40L BV421 antibody (5 µl/well). At the same time GolgiStop™ was added (2.64 µl/ml of R10 final concentration) to retain/stabilise CD40L-antibody complexes on the cell surface. The plate was then incubated for 20 hours at 37° C. and 5% $CO_2$ before staining the cells with CD3 FITC, CD4 BV650, CD8 APCeF780, Valpha24 PE and AQUA to allow identification of live, transduced T cells and specific subsets. Data was acquired on Fortessa X20 instruments using software FACSDiva version 8.0.1; data analysis was performed using FlowJo version 10.3 or version 10.4.1. Graphs were generated with GraphPad Prism version 7.02. Statistical significance was assessed using R with a 3-way repeated-measures ANOVA, with subset (i.e. CD4/8), TCR+/−, and transduction level as within-subject factors followed by pairwise post-hoc tests for each combination of transduction within a subset/TCR combination and p values adjusted using the Holm method.

FIG. 1 summarises data for the CD4+ T cell subset of five Wave T cell products tested. Following co-culture with an antigen negative cell line (Colo205) no difference in the frequency of CD40L+ cells is observed between non-transduced (ntd), MAGE-A4 TCR and CD8α_MAGE-A4 CD4+ TCR Wave T cells. This is true for both transduced (TCR+) cells and those lacking expression of the MAGE-A4 TCR (TCR−). These frequencies are also very similar to those observed in T cells that were cultured alone (T cells only). When the cells are presented with antigen positive target cells (A375) an increase in the frequency of CD40L+ cells was seen within the CD4+TCR+subset of MAGE-A4 TCR transduced Wave T cells. Compared to unstimulated T cells the frequency of CD40L+on CD4+TCR cells increased. A significantly higher proportion of CD4+CD40L+ T cells is detected in CD8α_MAGE-A4 TCR transduced Wave products following antigen recognition and activation.

Example 3. T Cell Proliferation

Figure 2:
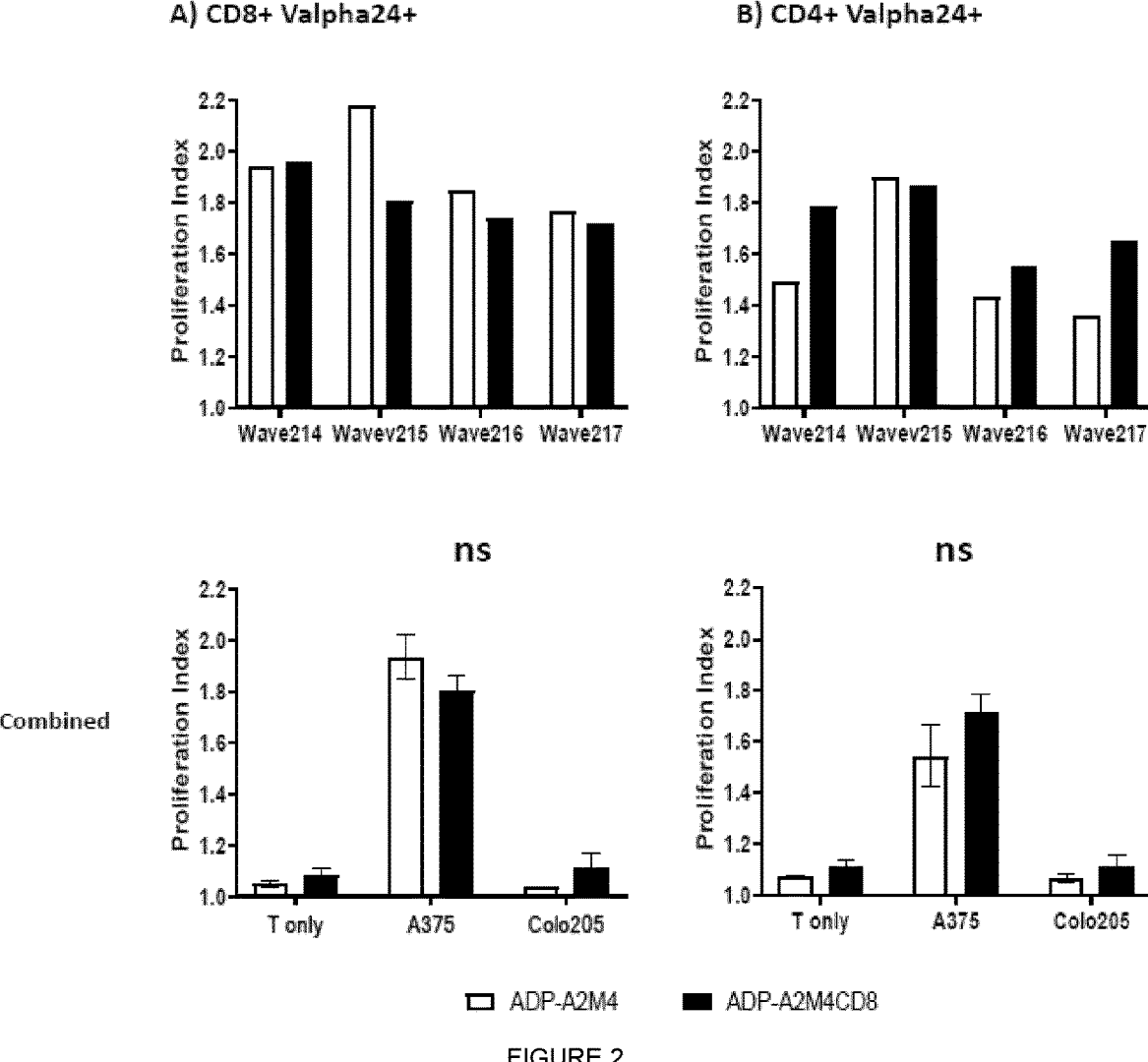
FIG. 2. Proliferation index of transduced CD4+ and CD8+ lymphocytes in response to antigen positive A375. The average number of divisions that all responding cells have undergone were plotted for the CD8+Valpha24+(A) and CD4+Valpha24+(B) cells expressing MAGE-A4 TCR (white) and CD8α_MAGE-A4 TCR (white). The PI was shown for four separate donors and as a combined mean±SEM across the four donors. Statistical significance was assessed using a 2-way ANOVA followed by Sidak post-hoc multiple comparisons test for variance among the groups.

The effect of CD8α homodimer on T cell antigen-specific functions was also assessed by calculating the proliferation index (PI) of the Valpha24+CD8+(TCR) and CD4+ T cell subsets within MAGE-A4 TCR and CD8α_MAGE-A4 TCR T cell products, in response to the MAGE-A4 positive cell line A375 (FIG. 2). The proliferation index accounts for the average number of divisions the responding cells have undergone.

T cell proliferation in response to antigen was accessed by flow cytometry using a fluorescent dye that allows for the simple detection of the number of cell divisions. T cells were stained with the violet laser excitable dye VPD450, which labels the parental cells uniformly. Upon division, the dye is evenly distributed between daughter cells, each then retaining approximately half of the fluorescence intensity of its parent. Therefore, the reduction of dye intensity indicates cell division and thus proliferation.

Non-transduced (ntd), MAGE-A4 TCR and CD8α_MAGE-A4 TCR wave T cell products from four different donors were thawed and rested for 26 hours at $2.0 \times 10^6$ cells/ml in tryptophan depleted RPMI to promote cell synchronisation. T cells were then stained with VPD450 and incubated alone or in co-culture with-antigen presenting cells at a 5:1 T cells to target cells ratio, in the presence or absence of $10^{-5}$ M MAGE-A4 peptide GVYDGREHTV. The antigen presenting A375 (MAGE-A4 positive) and the Colo205 (MAGE-A4 negative) were irradiated (~48 and ~33Gy respectively) prior to co-culture, in order to prevent target cell proliferation. Following 3 days of co-culture, the cells were harvested and stained for T cell markers (CD3, CD4, CD8 and Valpha24 to mark the TCR) and viability.

Proliferation was assessed in both the CD4 and CD8 total T cell populations and within the TCR positive and negative fractions using flow cytometry. The proliferation peaks were manually gated using the T only cells from the transduced and ntd samples as a guide to set the $G_0$ gate. This represented the undivided cells. Each generation of dividing cells that occurred after the G0 gate was gated (G1, G2 . . . Gx) as peak VPD450 reductions and antigen-driven proliferation was assessed by calculating percent divided and proliferation index. Samples were acquired on the BD™ LSR- Fortessa X-20 using the BD™ High Throughput Sampler (HTS) system in accordance to CBP079v00. For data acquisition, FACSDiva version 8.0.1 was used, and post-acquisition analysis was performed using FlowJo v10.4.1 and GraphPad PRISM v7.02.

Within the CD4+ fraction, across the 4 wave donors, cells transduced with of the CD8α_MAGE-A4 TCR displayed greater expansion compared to the MAGE-A4 TCR (FIG. 2). The presence of the additional CD8α homodimer on the CD4+ cells, led to an increase in the percentage of cells that underwent division and proliferation index when compared to the MAGE-A4 TCR.

Example 4. Cytokine Production in Response to Tumour Cells Lines

The main effector function of CD4+ T cells is to orchestrate immune response by providing feedback signals to antigen presenting cells as well as other T cell subsets. This role can be mediated by expression of co-stimulatory signals, like CD40L, or secretion of cytokines and chemokines.

To investigate the production of cytokines by CD8α_MAGE-A4 TCR T cells, T cells were co-cultured for 24 hours with either T2 cells with a titration of MAGE-A4 GVYDGREHTV peptide, or antigen positive A375 tumour cells. T cells were used as harvested (PBLs) as well as product purified for either CD4+ or CD8+ T cells.

T cells and target cells were added to the wells of 96-well U-bottomed culture plates in duplicate at 50,000 target and 50,000 T cells per well. Target cells were either T2 with added exogenous peptide, GVYDGREHTV, in range of $10^{-6}$ to $10^{-10}$M, or no peptide as a negative control, or the MAGE-A4 positive tumour cell line A375. Assay plates were incubated for 24 hours at 37° C./5% CO2. Culture media was collected (150 μl) for cytokine analysis by Luminex™ MAGPIX®.

Cytokine and chemokine analysis by MAGPIX™ was performed using the Invitrogen 25-plex human cytokine panel kit. Samples were acquired using a Bio-Rad Bio-Plex® MAGPIX™ Multiplex Reader using acquisition software Luminex XPONENT for MAGPIX version 4.2 Build 1705. Post-acquisition analysis was performed using R (v3.3.2). Any value above the top of the standard curve was adjusted to top value. Two-way repeated-measure ANOVAs were run separately for each cytokine, with transduction and T cell fraction as within-subject factors, followed by pairwise post-hoc tests for each combination of transduction within a transduction/T cell fraction combination and p values were adjusted using the Holm method. A pre-defined subset of relevant cytokines were analysed: Granulocyte-Macrophage Colony-Stimulating Factor (GM-CSF), IFN-γ, IL-2, Tumor Necrosis Factor (TNF)-α, MIP-1β (CCL4), IL-17, IL-10, IL-4, IL-5, IL-13, IL-2 Receptor.

Figure 3A:
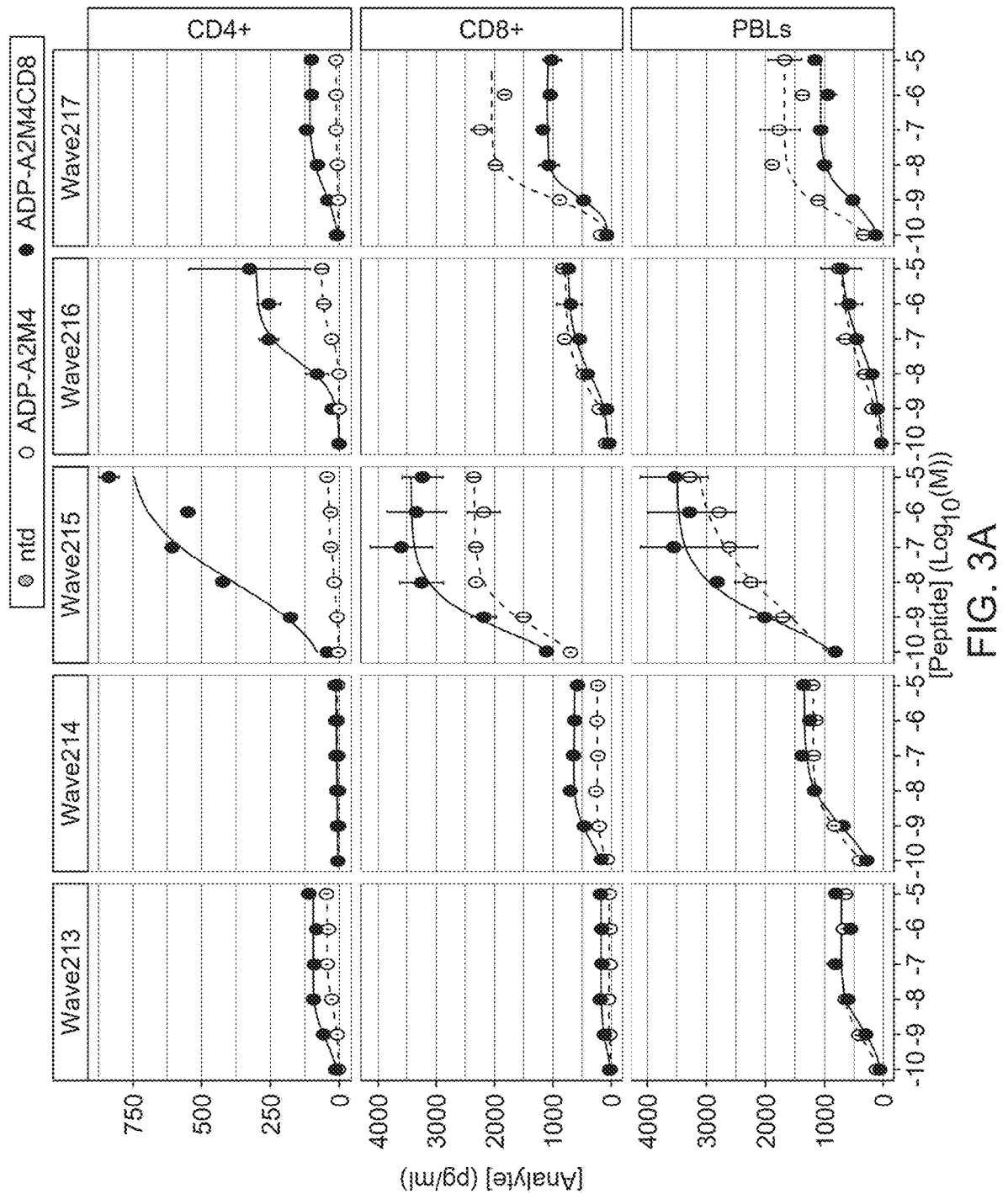
FIG. 3. Production of IFNγ in response to antigen. $5 \times 10^4$ T cells were co-incubated with either A) $5 \times 10^4$ T2 cells and a titration of MAGE-A4 GVYDGREHTV peptide as indicated on x axis or B) $5 \times 10^4$ antigen positive A375 cells. Supernatants were harvested after 24 hours and frozen for later analysis by Magpix®. Data from 5 assays was collated and analysed using R (CEL_ANA18_021). Columns indicated T cell donor (Wave213-217), and rows different T cell fractions (mixed PBL product, isolated CD4+ or isolated CD8+). T cell transduction is indicated by colour, non-transduced ntd=grey, MAGE-A4 TCR=white and CD8α_MAGE-A4 TCR=black. A). Data are represented as mean of 2 biological replicates ±SEM. The response curves were fitted using 4-parameter log-logistic function with baseline constrained to 0. B) Each point represents one biological replicate. Data collated in CEL_ANA18_021.
Figure 3B:
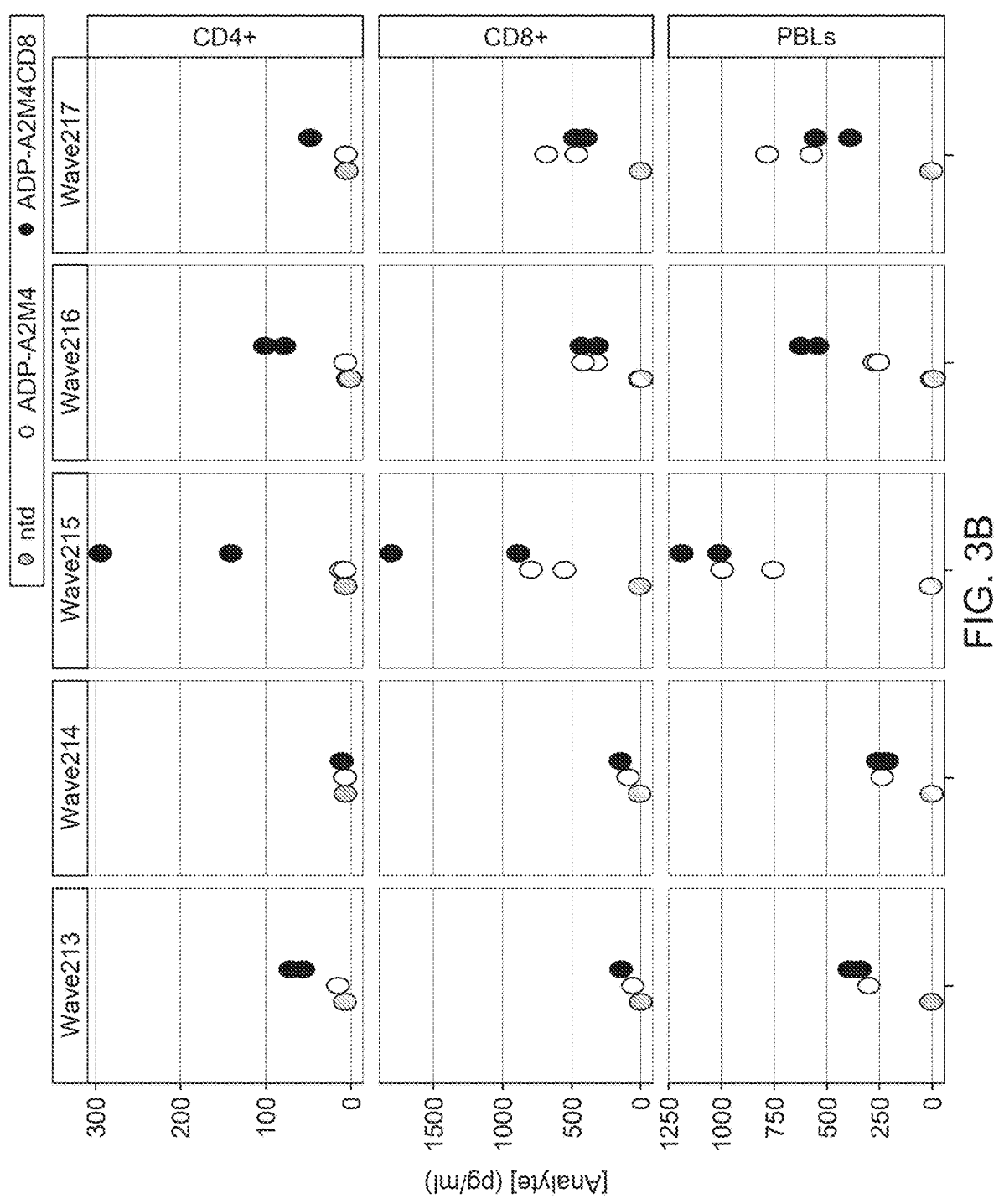

Data shown in FIG. 3 relates to the production of IFNγ. Data in FIG. 4 relates to the production of IL2. As shown in FIG. 3, when the co-culture included isolated CD4+ cells (top facets), although the absolute levels of cytokine were lower (especially for IFNγ where the maximum on the y axis is 750 μg/ml vs 4000 μg/ml for IL2 in FIG. 4) there is a much more consistent improvement in cytokine release by the CD8α_MAGE-A4 TCR T cells (black) compared to the MAGE-A4 TCR (white). This pattern is consistent across all 5 donors (except Wave214 which did not respond well in this assay. A similar result is seen in the IFNγ response to antigen positive A375 tumor cells (FIG. 3, Bottom panels). In general there is little difference between the two TCR constructs in the PBLs or CD8+ fractions, but an improvement in cytokine release between constructs can be seen in 4 out of 5 donors when CD4+ is investigated.

Figure 4A:
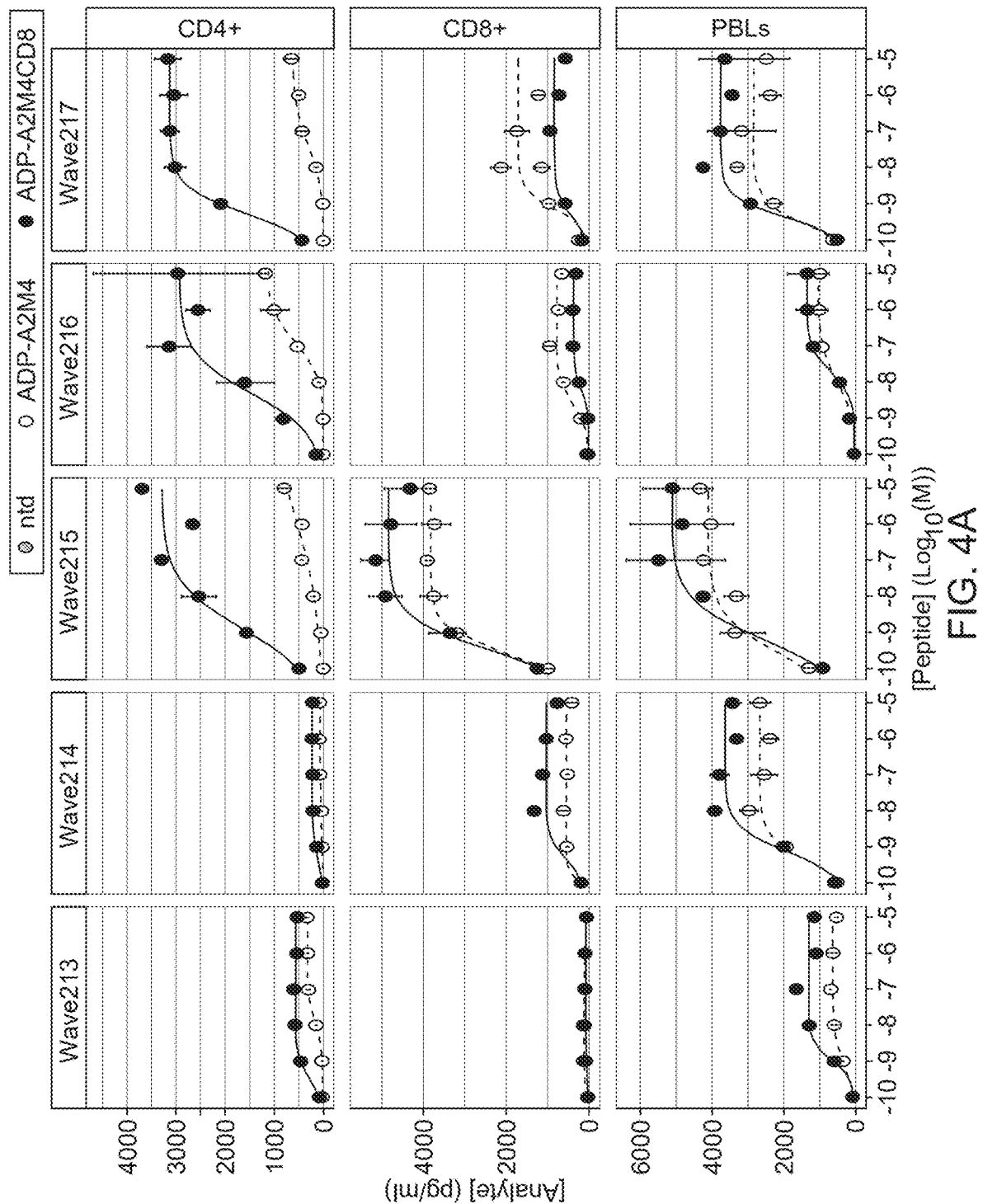
FIG. 4. Production of IL-2 in response to antigen. $5 \times 10^4$ T cells were co-incubated with either A) $5 \times 10^4$ T2 cells and a titration of MAGE-A4 GVYDGREHTV peptide as indicated on x axis or B) $5 \times 10^4$ antigen positive A375 cells. Supernatants were harvested after 24 hours and frozen for later analysis by Magpix®. Data from 5 assays was collated and analysed using R (CEL_ANA18_021). Columns indicated T cell donor (Wave213-217), and rows different T cell fractions (mixed PBL product, isolated CD4+ or isolated CD8+). T cell transduction is indicated by colour, ntd=grey, MAGE-A4 TCR=white and CD8α_MAGE-A4 TCR=black. A) Data are represented as mean of 2 biological replicates ±SEM. The response curves were fitted using 4-parameter log-logistic function with baseline constrained to 0. B) Each point represents one biological replicate. Data collated in CEL_ANA18_021.
Figure 4B:
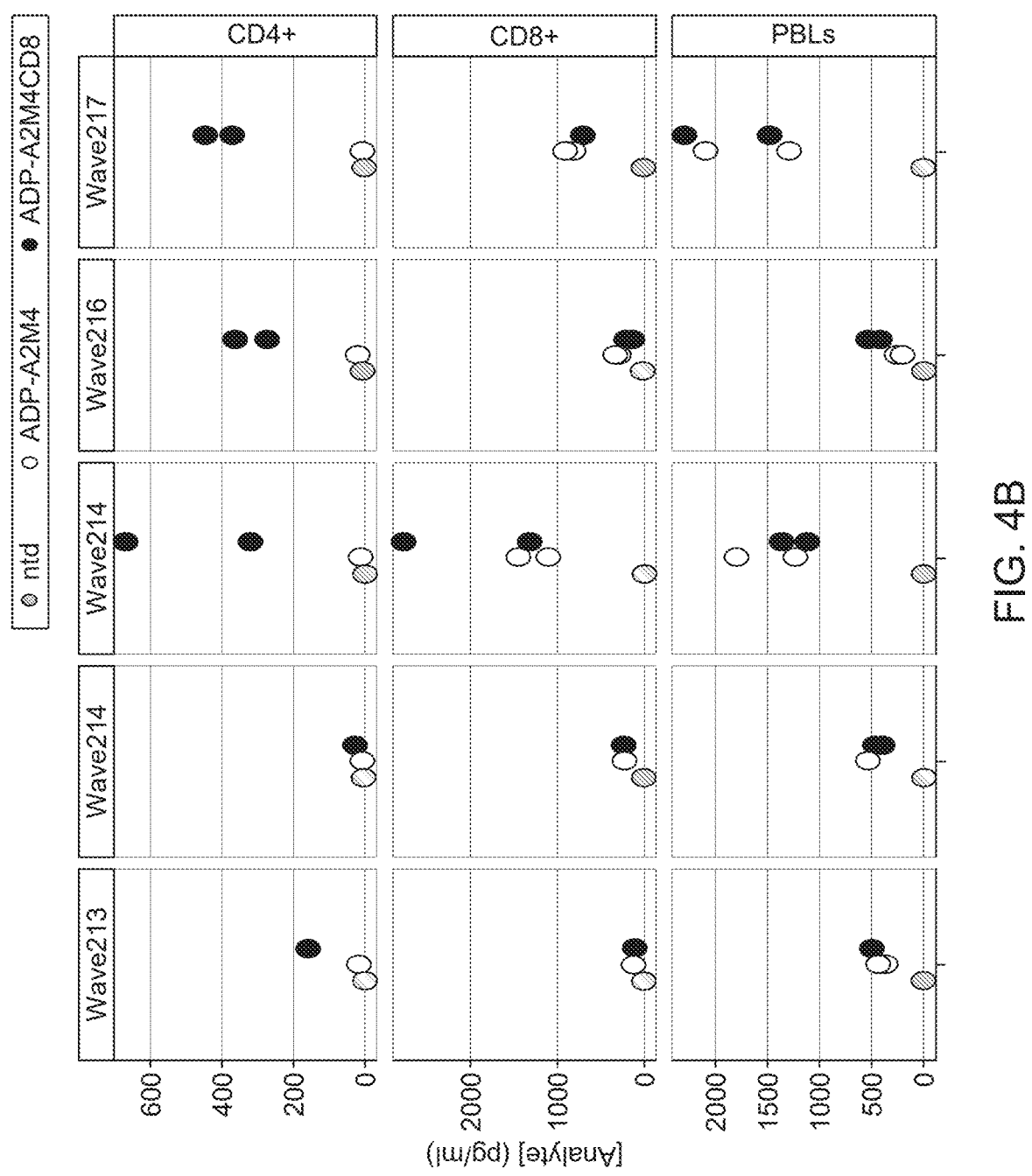

In FIG. 4, the CD4+ cell data (top facets), demonstrates that there is also a consistent improvement in cytokine release by the CD8α_MAGE-A4 TCR T cells (black) compared to the MAGE-A4 TCR (white). The same trend holds for the production of Granulocyte-Macrophage Colony-Stimulating Factor (GM-CSF), Tumor Necrosis Factor (TNF)-α, and MIP-1β (CCL4), data not shown. The remaining six cytokines (IL-17, IL-10, IL-4, IL-5, IL-13, IL-2 Receptor) showed minimal production in four out of five wave donors although the levels produced were higher from the CD8α_MAGE-A4 TCR T cells compared to MAGE-A4 TCR T cells for both CD4+ and CD8+ isolated cells.

In conclusion, from the cytokines analysed, and in particular IFNγ, IL-2, TNFα, GM-CSF, and MIP1β, there is an improvement in cytokine release by the CD8α_MAGE-A4 TCR T cells compared to the MAGE-A4 TCR T cells.

Example 5. Cytokine Production in Response to Tumour Cells Lines in Dendritic Cells Co-Culture It was hoped that by introducing CD8α into TCR-transduced CD4+ T cells might promote engagement with additional elements of the immune system to elicit a sustained anti-tumour response hence it was our objective to assess the interaction of CD8α_MAGE-A4 TCR T cells with dendritic cells (DCs) during DC maturation and T cell activation. In the context of the tumor microenvironment, improved maturation and activity of DCs could help boost the overall anti-tumor immune response and activation of T cells. To investigate the interactions between T cells and dendritic cells during the DC maturation and T cell activation process, two assay types were set up involving the co-culture of immature DCs, T cells and tumour cell lines. This was designed to reflect the in vivo situation where DCs take up antigen from surrounding tumour cells and present on their MHC class II, rather than simply loading with exogenous peptide (which would only present on MHC class I). To address both the autologous situation and confirm application to clinical large-scale T cells, assays included small scale T cells made from blood donors with matched dendritic cells, as well as wave scale T cells.

(a) Cell Preparation and Co-Culture

Co-cultures were set up for 48 hours and each assay type included two small scale T cell preps (donors TEA and TSA, or NLA and OBA) with donor matched DCs, and two large scale donors (Wave213 and Wave217 or Wave216 and Wave217) with unmatched DCs (as specified in figure legends). For these assays antigen positive target cell lines (A375 or NCI-H1755) and an antigen negative target cell line (Nalm6) were included. As positive controls for dendritic cell maturation, wells containing either a cytokine cocktail or lipopolysaccharide (LPS) were included.

After 7 days of differentiation from CD14+ monocytes, the immature dendritic cells were washed three times in R10, counted and seeded into 48-well plates for co-culture with MAGE-A4-positive or MAGE-A4-negative tumour cell lines and TCR transduced T cells. Co-culture was set up for 48 hours and incubated at 37° C./5% $CO_2$ to assess the effect of this co-culture on DC maturation and activation. All co-culture experiments used 100,000 target cells (A375, NCI-H1755 or Nalm6), 100,000 dendritic cells and 400,000 T cells. T cells and dendritic cells produced from the same donor were used in each assay. After 48 hours of co-culture supernatants were collected (150 μl per well) and frozen at −80° C. for subsequent cytokine and chemokine analysis by MAGPIX™ or cells harvested for flow cytometry.

(b) Effect on Maturation Status of Dendritic Cells

To assess the maturation status of dendritic cells at the end of the 48 hour co-culture period, multicolour immunophenotypic analysis was performed using flow cytometry to determine the expression of maturation markers on dendritic cells. The target cell lines used for the immunophenotyping co-cultures were tagged with nuclear GFP to allow easy differentiation between dendritic cells and target cells. The monoclonal antibodies used were directed against CD1a, CD14, CD40, CD80, HLA-DR, CD3, CD4 and CD40L. In addition to CD1a, DCs were stained for CD40, CD80 and HLA-DR (MHC II). All three of these markers are expressed at low level in immature dendritic cells and are up-regulated upon DC maturation. The expected phenotype of immature dendritic cells is: CD1a+, HLA-DRlow, CD80low, CD40low, CD14-/low, and that of mature dendritic cells is: CD1a+, HLA-DRhigh, CD80high, CD14-/low.

Dendritic cells co-incubated with CD8α_MAGE-A4 TCR or MAGE-A4 TCR T cells demonstrated equivalent upregulation of CD80, CD40 and HLA-DR markers in response to antigen positive A375 cells but not with antigen negative Nalm6 cells or non-transduced T cells, hence the activation is TCR and antigen specific. There was no difference between DCs incubated with CD8α_MAGE-A4 or MAGE-A4 PBLs. Both CD8α_MAGE-A4 and MAGE-A4 transduced T cells specifically activated by antigen can promote the maturation of immature dendritic cells (data not shown).

(c) Cytokine Assay

The methodology for the cytokine assay is described in example 4.

(c. i.) IL-12

Figure 5:
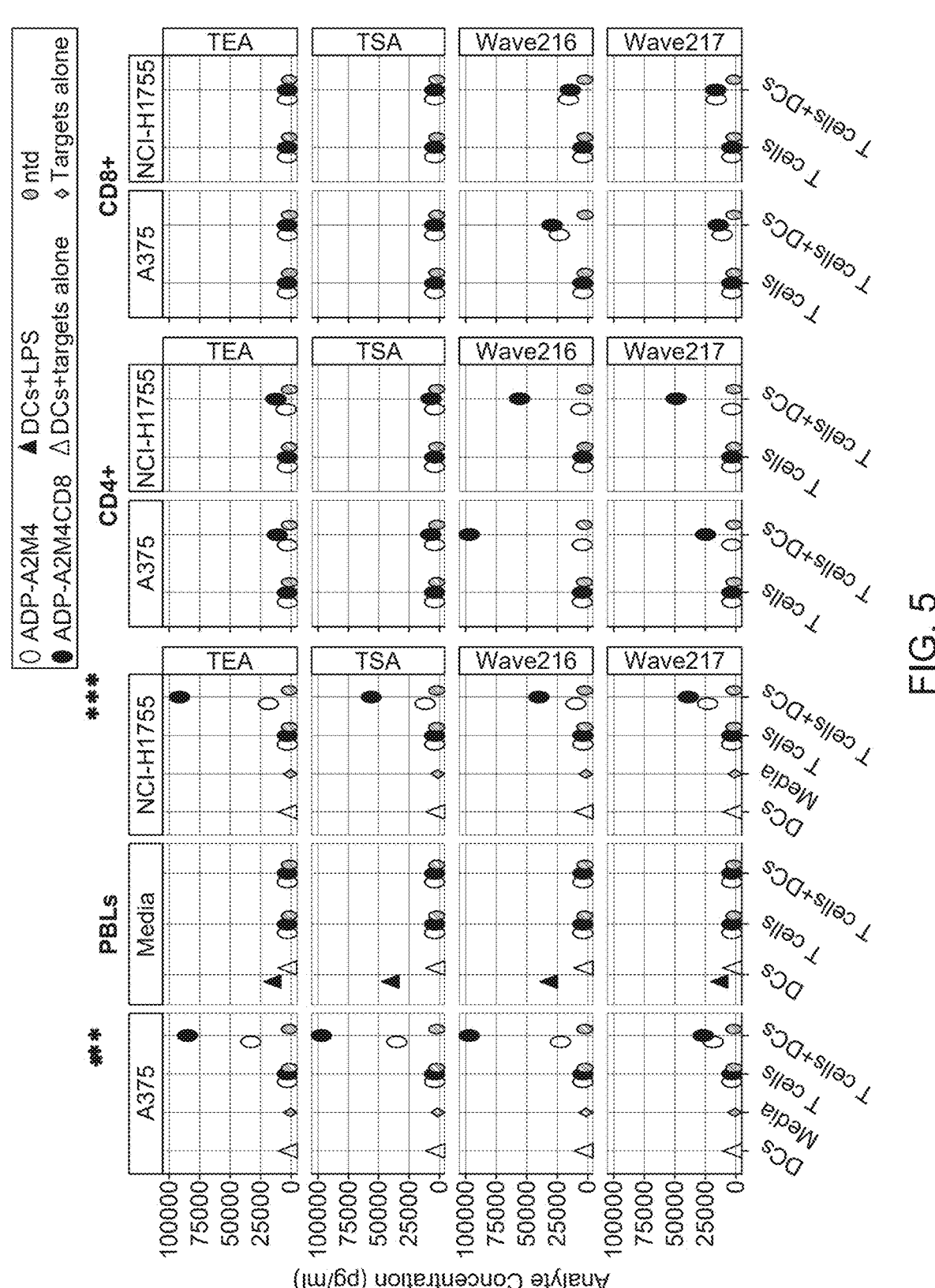
FIG. 5. Production of IL-12 (p40/p70) in dendritic cell co-culture assays. Left, centre and right hand panels show data from mixed PBLs, isolated CD4+ and isolated CD8+ T cells as indicated. The x axis indicates T cells and tumour alone ("T cells"), T cells, tumour and DCS ("T cells +DCs"), tumour cells alone ("media") or DCs and tumour cells without T cells ("DCs"). T cell transduction is indicated by colour ntd=grey, MAGE-A4 TCR=hollow black, and CD8α_MAGE-A4 TCR=filled black. Additional positive control for DC activation were LPS (filled triangle). Individual plots are shown for multiple donors (TEA and TSA=small scale T cells with autologous DCs; Wave216 and Wave217=large scale T cells co-cultured with DCs from donor TSA).

IL-12 is the principal cytokine produced by activated mature dendritic cells and is enhanced through CD40 signalling. Naïve CD4+ T cells activated in the presence of IL-12 and/or IFNγ tend to differentiate into Th1 cells, which in turn support IFNγ production and increased cytotoxic activity of CD8+ T cells. $1\times10^5$ antigen-positive (A375 and NCI-H1755) or antigen-negative (Nalm6) tumour cell lines were co-cultured in a 48 well plate with $1\times10^5$ immature dendritic cells and $4\times10^5$ T cells. Culture supernatants were harvested after 48 hours and cytokines analysed by Magpix®. Data is shown in FIG. 5. Any data points that exceeded the top of the standard curve have been plotted as the maximum value. As the standard curves for IL-12 were consistently still in the linear range at the highest point of the standard curve, the standard range for IL-12 (p40/p70) was extended to 100,000 μg/ml for the purpose of data analysis and graph generation. All experimental conditions were tested in biological duplicates and both data points are plotted. Three-way repeated-measure ANOVAs were run separately for each cytokine and positive-control target, with transduction, T cell fraction, and presence or absence of DCs as within-subject factors, followed by pair-wise post-hoc tests for each combination of transduction within a transduction/T cell fraction/DC combination and p values were adjusted using the Holm method. Only significant comparisons between MAGE-A4 TCR and CD8α_MAGE-A4 TCR are signified on graph *p<0.05, p<0.01, *p<0.005.

In FIG. 5, IL-12 was only seen in those conditions containing DCs ("T cells +DCs" on the X axis) confirming this was a DC specific analyte. In response to either A375 or NCI-H1755 antigen positive target lines, large amounts of IL-12 were produced by DCs in co-culture with unseparated T cells ("PBLs", left hand panel). When co-cultured with CD8α_MAGE-A4 TCR T cells the amount of IL-12 was up to double the amount seen in positive control samples which were incubated with LPS (filled triangle). Consistently across every donor, significantly more IL-12 was produced by DCs exposed to CD8α_MAGE-A4 TCR T cells (black points) than those cultured with MAGE-A4 TCR T cells (hollow points) (p=0.002779 A375 and p=0.0000964 NCI-H1755). No IL-12 was produced by DCs cultured with T cells, or media alone, confirming this is a MAGE-A4 antigen specific response.

When the co-culture included isolated CD4+ T cells (middle panel), the DCs still produced IL-12. The levels of IL-12 induced by the large scale CD4+CD8α_MAGE-A4 TCR transduced T cells (Wave216 and Wave217) were broadly similar to that seen with mixed PBLS, yet were barely above background with MAGE-A4 TCR T cells. IL-12 levels produced in co-culture with small scale donors (TEA and TSA) were lower, but still above background. In conclusion there was a greater response with CD8α_MAGE-A4 TCR T cells. The increase in IL-12 production between the CD4+ and mixed PBLs conditions highlights that although the licensing of DC maturation is mainly a CD4+ function, CD8+ T cells also play an important role in the positive feedback loop between DCs and T cells in response to antigen. When co-cultures included isolated CD8+ T cells, the DCs did not produce any IL-12 when combined with small scale T cells, and produced moderate levels when combined with large scale donors, and this was unaffected by the CD8α modification.

(c. ii.) Monokine Induced by Gamma Interferon (MIG or CXCL9),

MIG is a chemoattractant for T cells and tumour-infiltrating lymphocytes that is produced by dendritic cells, macrophages and other cell types in response to IFNγ. Its primary function is to recruit primed T lymphocytes to the site of inflammation.

$1\times10^5$ antigen-positive (A375 and NCI-H1755) or antigen-negative (Nalm6) tumour cell lines were co-cultured in a 48 well plate with $1\times10^5$ immature dendritic cells and $4\times10^5$ T cells. Culture supernatants were harvested after 48 hours and cytokines analysed by Magpix®.

Figure 6:
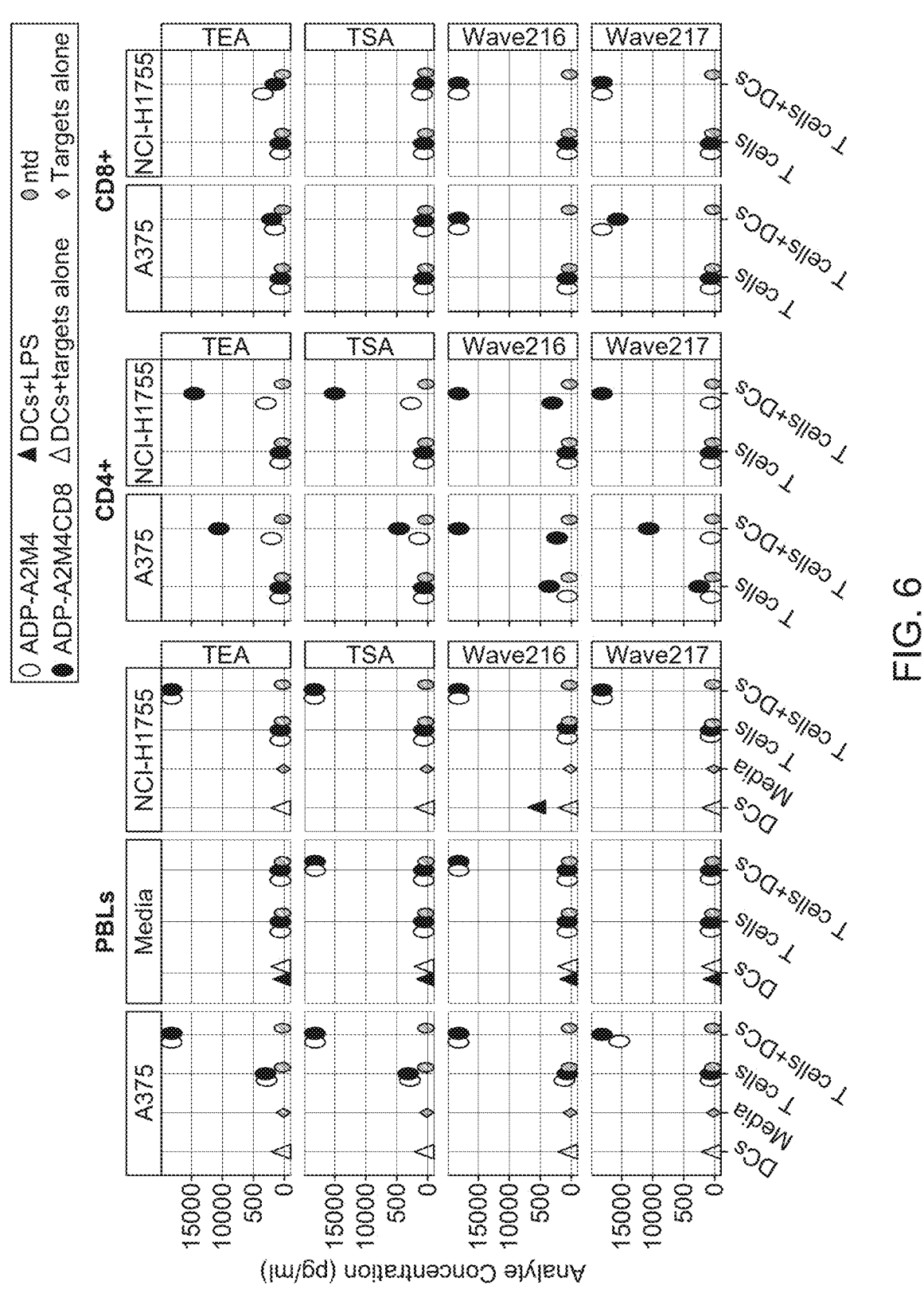
FIG. 6. Production of MIG (CXCL9) in DC co-culture assays. Left, centre and right hand panels show data from mixed PBLs, isolated CD4+ and isolated CD8+ T cells as indicated. The x axis indicates T cells and tumour alone ("T cells"), T cells, tumour and DCS ("T cells +DCs"), tumour cells alone ("media") or DCs and tumour cells without T cells ("DCs"). T cell transduction is indicated by colour ntd=grey, MAGE-A4 TCR=hollow black, and CD8α_MAGE-A4 TCR=filled black. Additional positive control for DC activation were LPS (filled triangle). Individual plots are shown for multiple donors (TEA and TSA=small scale T cells with autologous DCs; Wave216 and Wave217=large scale T cells co-cultured with DCs from donor TSA).

Data is shown in FIG. 6. Any data points that exceeded the top of the standard curve have been plotted as the maximum value. All experimental conditions were tested in biological duplicates and both data points are plotted. Three-way repeated-measure ANOVAs were run separately for each cytokine and positive-control target, with transduction, T cell fraction, and presence or absence of DCs as within-subject factors, followed by pair-wise post-hoc tests for each combination of transduction within a transduction/T cell fraction/DC combination and p values were adjusted using the Holm method. Only significant comparisons between MAGE-A4 TCR and CD8α_MAGE-A4 TCR are signified on graph *p<0.05, p<0.01, *p<0.005.

The secretion pattern of MIG (Error! Reference source not found. FIG. 6) is similar to IL-12. MIG produced by DCs co-cultured with mixed PBL T cells is above the quantitation limit of the assay and no differences can be measured. When incubated with isolated CD4+ cells however, there is a clear difference in the MIG produced by the DCs in response to CD8α_MAGE-A4 TCR compared to MAGE-A4 TCR T cells with both large and small scale donors. High levels of MIG were also produced by DCs in co-culture with the large scale CD8+ T cells.

(c. iii.) IL-6

Figure 7:
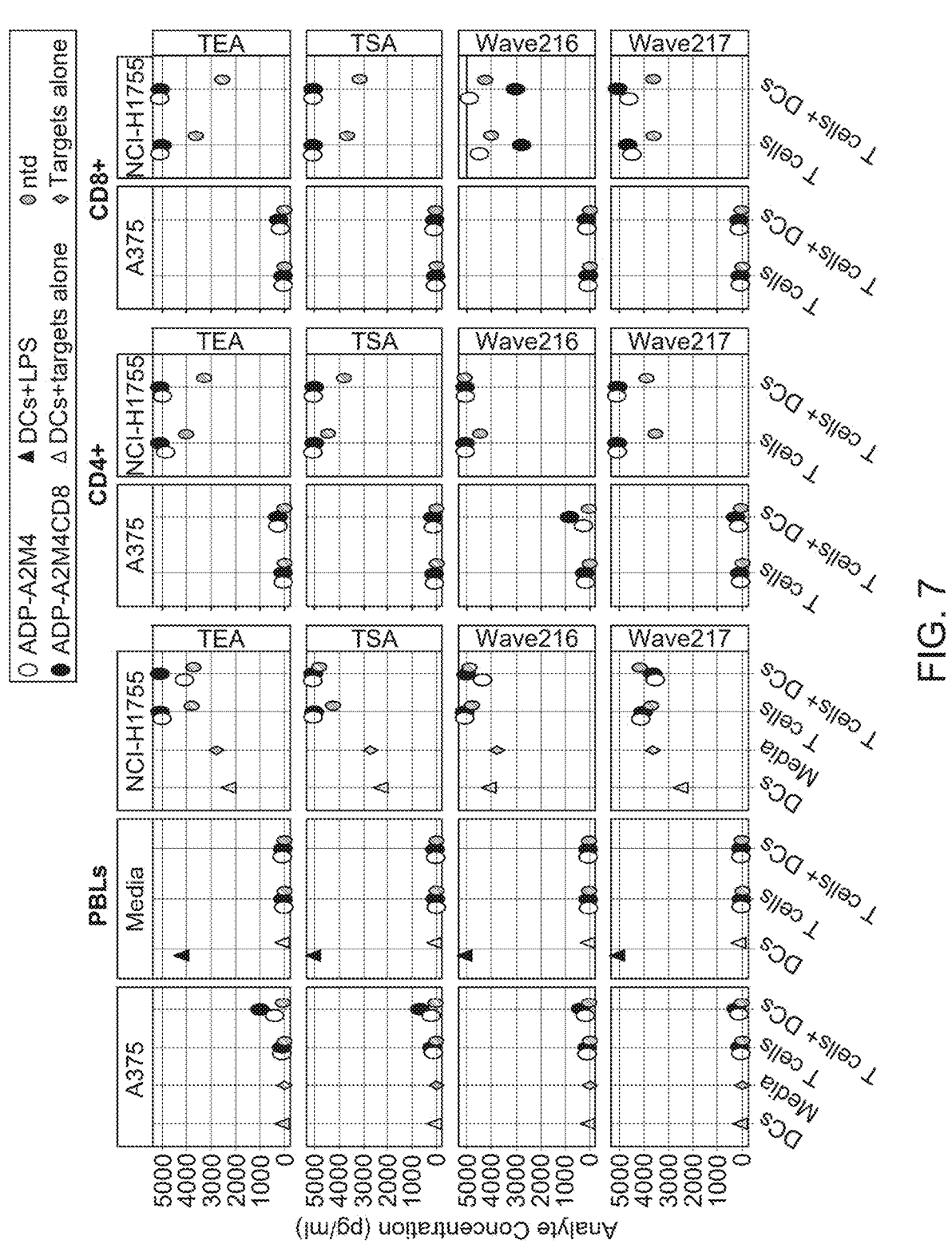
FIG. 7. Production of IL-6 in DC co-culture assays. Left, centre and right hand panels show data from mixed PBLs, isolated CD4+ and isolated CD8+ T cells as indicated. The x axis indicates T cells and tumour alone ("T cells"), T cells, tumour and DCS ("T cells +DCs"), tumour cells alone ("media") or DCs and tumour cells without T cells ("DCs"). T cell transduction is indicated by colour ntd=grey, MAGE-A4 TCR=hollow black, and CD8α_MAGE-A4 TCR=filled black. Additional positive control for DC activation were LPS (filled triangle). Individual plots are shown for multiple donors (TEA and TSA=small scale T cells with autologous DCs; Wave216 and Wave217=large scale T cells co-cultured with DCs from donor TSA).

IL-6 is made by several cell types, including DCs. Clinically it is associated with poor-prognosis and is one of the major cytokines implicated in cytokine release syndrome (CRS). The Magpix data for IL-6 is shown in FIG. 7. The NCI-H1755 cell line secretes approximately 3-4000 pg/ml of IL-6, although the response when co-cultured by transduced T cells is generally above that of targets alone ("media" on x axis, or ntd (grey point)) so there is some production by DCs. In response to co-culture with T cells and A375 cells there is some also IL-6 production by DCs (up to ~1000pg/ml).

$1 \times 10^5$ Antigen-positive (A375 and NCI-H1755) or antigen-negative (Nalm6) tumour cell lines were co-cultured in a 48 well plate with $1 \times 10^5$ immature dendritic cells and $4 \times 10^5$ T cells. Culture supernatants were harvested after 48 hours and cytokines analysed by Magpix®. Any data points that exceeded the top of the standard curve have been plotted as the maximum value. All experimental conditions were tested in biological duplicates and both data points are plotted. Three-way repeated-measure ANOVAs were run separately for each cytokine and positive-control target, with transduction, T cell fraction, and presence or absence of DCs as within-subject factors, followed by pair-wise post-hoc tests for each combination of transduction within a transduction/T cell fraction/DC combination and p values were adjusted using the Holm method. Only significant comparisons between MAGE-A4 TCR and CD8α_MAGE-A4 TCR are signified on graph *p<0.05, p<0.01, *p<0.005.

Whilst more IL-6 is produced by DCs in co-culture with CD8α_MAGE-A4 TCR T cells than with MAGE-A4 TCR (1.8-2.9 fold, p=0.027115 with A375) the amounts are much less than seen when DCs are stimulated with the positive control (LPS, filled triangle) or the IL-6 made by tumour cells themselves (NCI-H1755). In contrast the levels of IL-12 (a pro-T cell cytokine) produced in the same assays, was higher than either positive control (FIG. 5).

(c. iv.) IFNγ

IFNγ is a key cytokine secreted by activated T cells in response to antigen and has multiple roles in the anti-tumour response.

Figure 8:
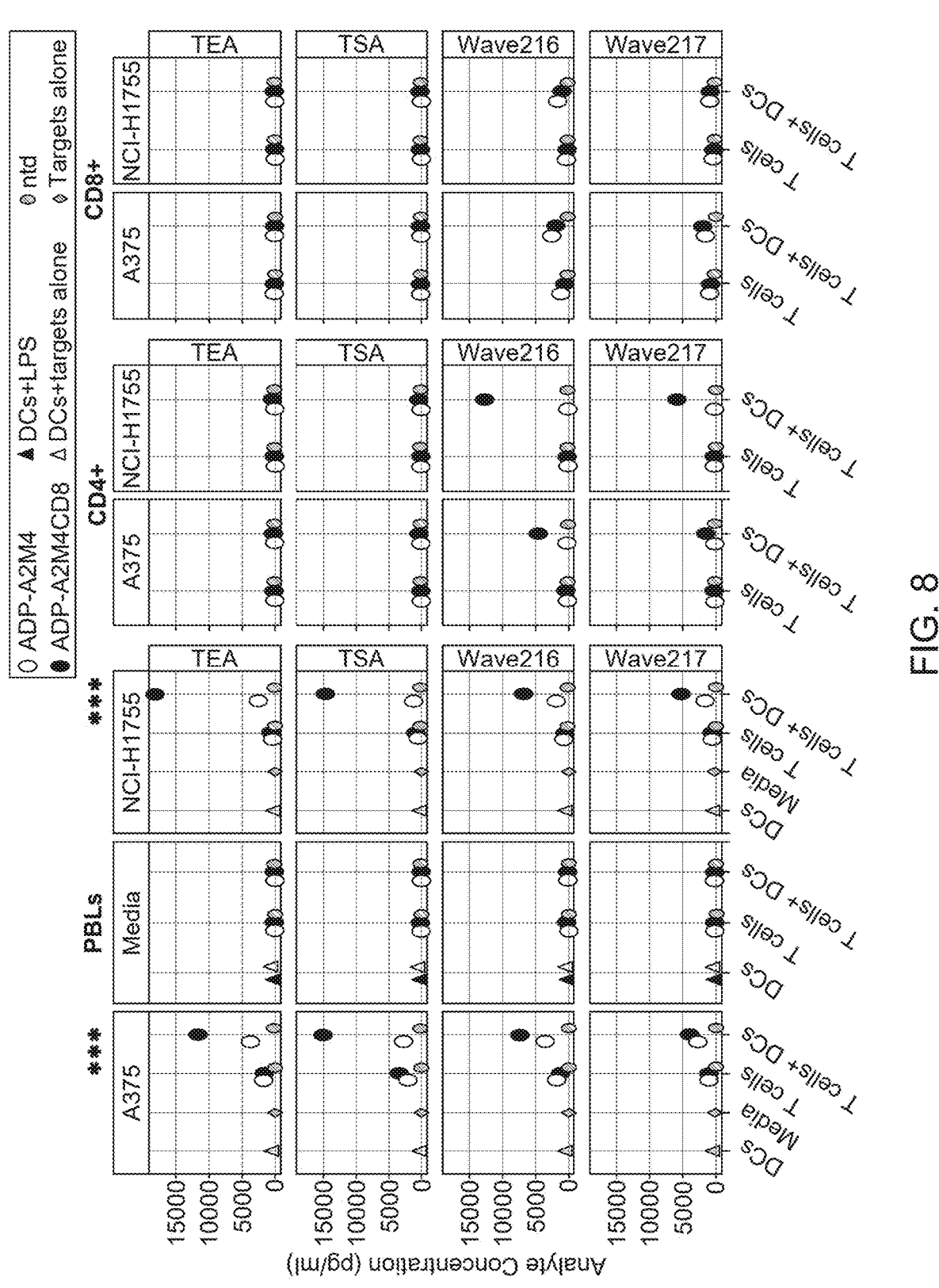
FIG. 8. Production of IFNγ in DC co-culture assays. Left, centre and right hand panels show data from mixed PBLs, isolated CD4+ and isolated CD8+ T cells as indicated. The x axis indicates T cells and tumour alone ("T cells"), T cells, tumour and DCS ("T cells+DCs"), tumour cells alone ("media") or DCs and tumour cells without T cells ("DCs"). T cell transduction is indicated by colour ntd=grey, MAGE-A4 TCR=hollow black, and CD8α_MAGE-A4 TCR=filled black. Additional positive control for DC activation were LPS (filled triangle). Individual plots are shown for multiple donors (TEA and TSA=small scale T cells with autologous DCs; Wave216 and Wave217=large scale T cells co-cultured with DCs from donor TSA).

$1 \times 10^5$ Antigen-positive (A375 and NCI-H1755) or antigen-negative (Nalm6) tumour cell lines were co-cultured in a 48 well plate with $1 \times 10^5$ immature dendritic cells and $4 \times 10^5$ T cells. Culture supernatants were harvested after 48 hours and cytokines analysed by Magpix®. Data is shown in FIG. 8. IFNγ secreted by T cells at 48h in the absence of DCs ("T cells" on x axis, FIG. 8) broadly reflects what was seen in previous 24h co-culture assays (low thousands; Error! Reference source not found. FIG. 3) and there are limited (not statistically significant) differences seen between the MAGE-A4 TCR and the CD8α_MAGE-A4 TCR T cell products. Any data points that exceeded the top of the standard curve have been plotted as the maximum value. The standard range for IFNγ in the 25-plex assay kit is up to –4,450 µg/ml. As the standard curves were consistently still in the linear range at the highest point of the standard curve, the standard range was extended to 20,000 µg/ml for the purpose of data analysis and graph generation and the y-axis of each graph has been set to this value. All experimental conditions were tested in biological duplicates and both data points are plotted. Three-way repeated-measure ANOVAs were run separately for each cytokine and positive-control target, with transduction, T cell fraction, and presence or absence of DCs as within-subject factors, followed by pair-wise post-hoc tests for each combination of transduction within a transduction/T cell fraction/DC combination and p values were adjusted using the Holm method. Only significant comparisons between MAGE-A4 TCR and CD8α_MAGE-A4 TCR are signified on graph *p<0.05, p<0.01, *p<0.005.

When DCs are added to a co-culture of CD8α_MAGE-A4 TCR T cells and antigen positive target cells (A375 or NCI-H1755), IFNγ release increases dramatically (up to 29 fold, donor TEA, NCI-H1755) whereas the effect of adding DCs on the MAGE-A4 TCR T cells is smaller (up to 7 fold, donor TEA, NCI-H1755). There is a significant difference between of IFNγ produced in the presence of DCs by CD8α_MAGE-A4 TCR T cells as compared to MAGE-A4 TCR T cells (p=0.000111 A375, p=0.000197 NCI-H1755). Small scale CD8α_MAGE-A4TCR T cells donors (TEA and TSA) showed an even more pronounced increase in IFNγ levels when co-cultured with antigen positive target cells and DCs. This data illustrates the other arm of the DC:T cell interaction, that the improved activation of DCs by the CD8α_MAGE-A4 TCR T cells is in turn allowing the DCs to improve T cell activation. No IFNγ production was observed when MAGE-A4 TCR or CD8α_MAGE-A4 TCR transduced T cells were co-cultured with MAGE-A4 negative Nalm6 cells, with or without addition of DCs, thus demonstrating that the observed responses are antigen specific.

Example 6. Killing of Antigen Positive Microtissues by CD8α_MAGE-A4 TCR T Cells The killing of antigen positive microtissues by CD8α_MAGE-A4 TCR T cells was investigated. Cytotoxic activity against tumour cells is generally characterised as a function of CD8+ cells, but can also be a minor function of CD4+ T cells. The cytotoxic activity of MAGE-A4 TCR and CD8α_MAGE-A4 TCR T cells towards GFP labelled 3D cancer cell line microtissues was determined by IncuCyte assay of 3D cancer cell microtissues.

MAGE-A4 and HLA-A2 positive A375.GFP melanoma cells transduced with cytoplasmic GFP lentivirus were seeded in ultra-low attachment (ULA) 384-well microplates at 150 cells/well and 1200 cells/well starting cell densities and briefly spun down before being incubated at 37° C./5% $CO_2$ to allow 3D microtissues of the differing sizes to form naturally. Imaging started from the point of cell seeding and continued after addition of T cells until assay completion using the IncuCyte ZOOM 40768 (Essen Bioscience) with images acquired at 3 hour intervals at 10× magnification. Uniform microtissue formation was confirmed in each well prior to the addition of T cells. After 6 days microtissues formed from 150 cells/well seeded were ~550-600 µm in diameter (hereafter termed 'small microtissues'), while those formed from 1200 cells/well seeded were –800 µm in diameter (hereafter termed 'large microtissues'). A375.GFP cells seeded into ULA plates formed stable microtissues of two uniform sizes (small and large) over 6 days prior to addition of T cells, FIGS. 13 A and B top panels shows this for small and large MAGE-A4 expressing A375.GFP microtissues respectively in the context of the Wave 217 cells.

T cell populations were added as unseparated PBLs (20,000 cells/well), as well as pure separated CD4+(80,000 cells/well) and CD8+(20,000 cells/well) fractions. 10 µM GVYDGREHTV MAGE-A4 peptide was also added to designated wells as an additional control for all conditions (data not shown). Following assay completion, raw images of the green fluorescence from each well for all timepoints were analysed whereby the core microtissue fluorescence area was masked, allowing the area of the microtissue to be calculated for each replicate and treatment condition for all timepoints studied. An increase or decrease in fluorescence metrics over time was indicative of 3D microtissue growth or death respectively. 3D microtissue killing metric plots were produced.

All data were normalised to the timepoint of T cell addition to compensate for any small variances in microtissue size between replicates before T cell killing. Microtissue area over time and area under the curve (AUC) data were determined up to the endpoint of the assays, data is shown in FIGS. 9 to 13.

Figure 9A:
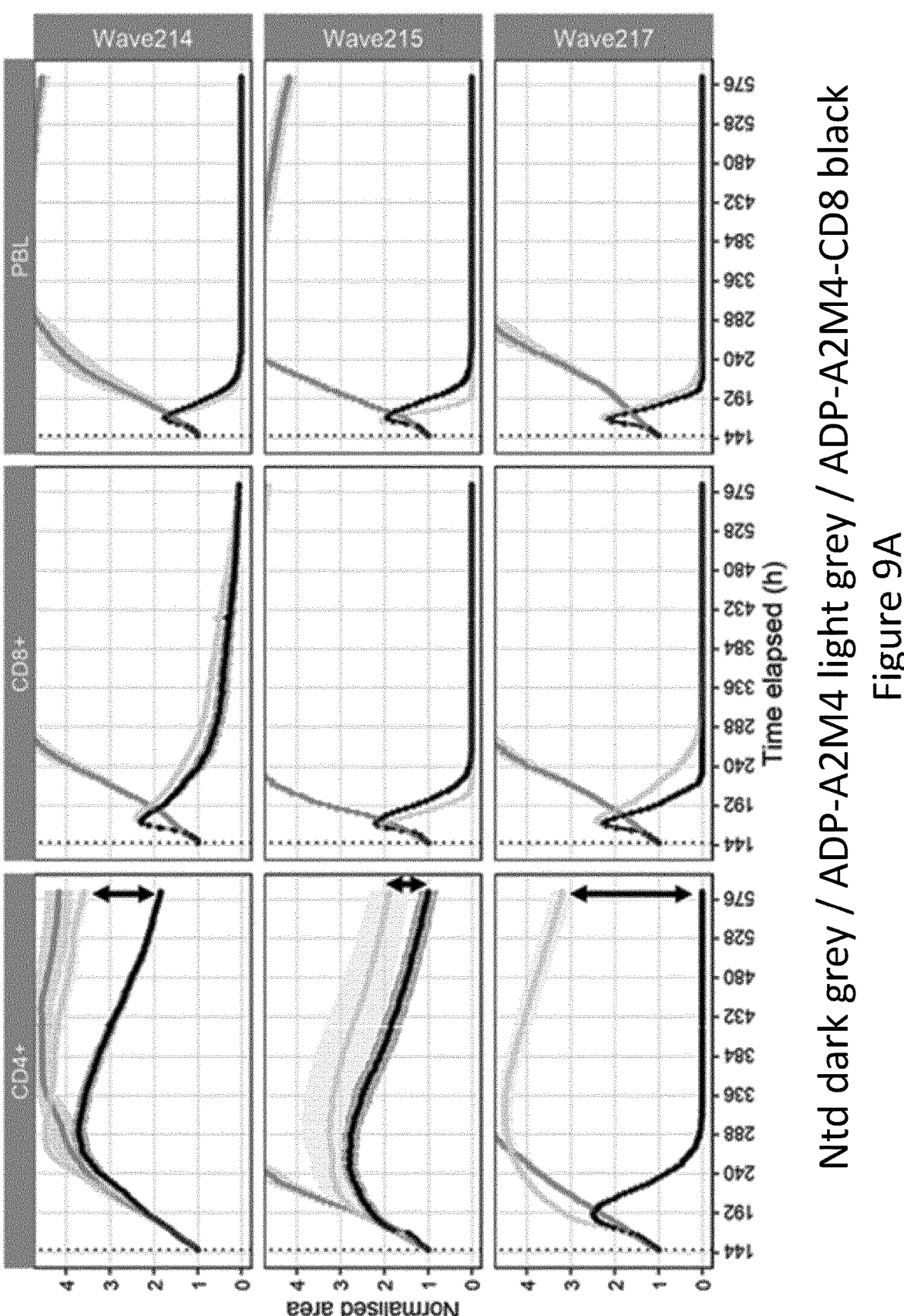
FIG. 9. Cytotoxic activity of ADP-A2M4CD8 T cells towards large, MAGE-A4 expressing A375.GFP microtissues (~800 μm diameter—1200 cells/well seeded). The GFP fluorescence area of the central core of the microtissue in each well was measured over time for each treatment (mean of 6 replicates+/−SEM shown for all conditions)). Dotted lines indicate T cell addition. Black arrows indicate difference in microtissue area with CD4+ADP-A2M4 and ADP- A2M4CD8 T cells at the assay end point. Data is expressed as microtissue core fluorescence area for each condition over time.
Figure 9B:
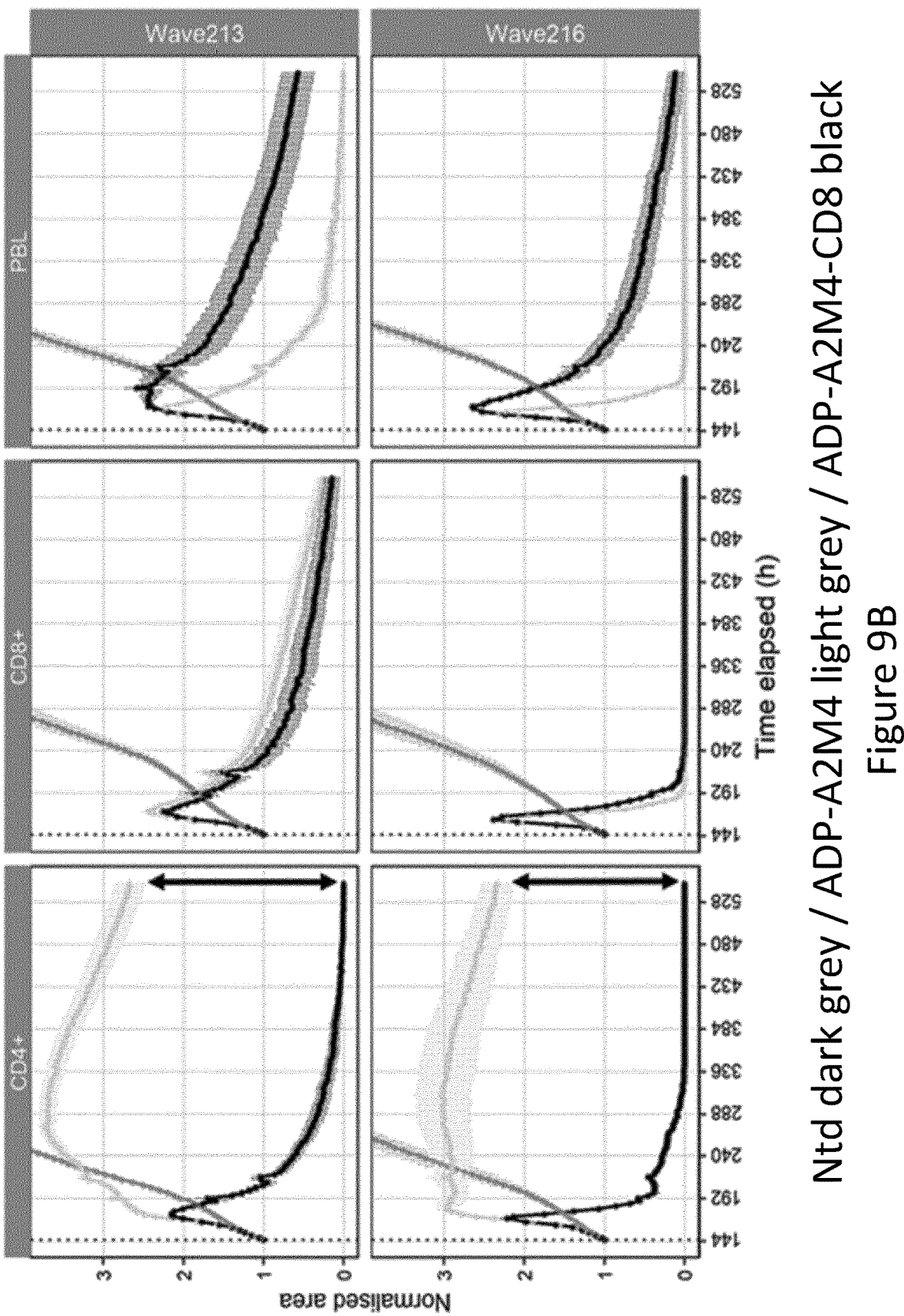
Figure 11A:
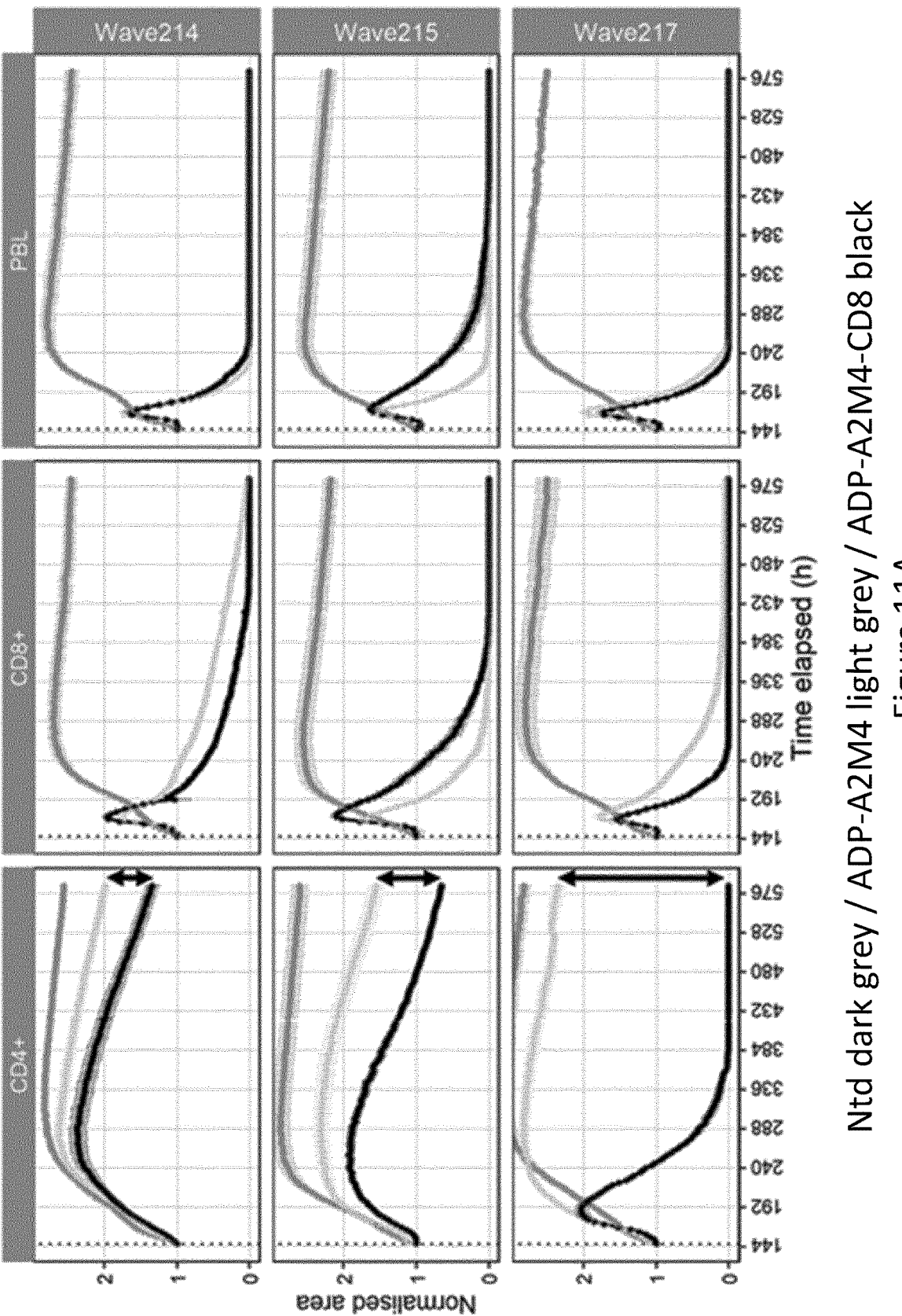
FIG. 11 Cytotoxic activity of ADP-A2M4CD8 T cells towards large, MAGE-A4 expressing A375.GFP microtissues (~800 μm diameter—1200 cells/well seeded). The GFP fluorescence area of the central core of the microtissue in each well was measured over time for each treatment (mean of 6 replicates+/−SEM shown for all conditions)). Dotted lines indicate T cell addition. Black arrows indicate difference in microtissue area with CD4+ADP-A2M4 and ADP-A2M4CD8 T cells at the assay end point. Data is expressed as microtissue core fluorescence area for each condition over time.
Figure 11B:
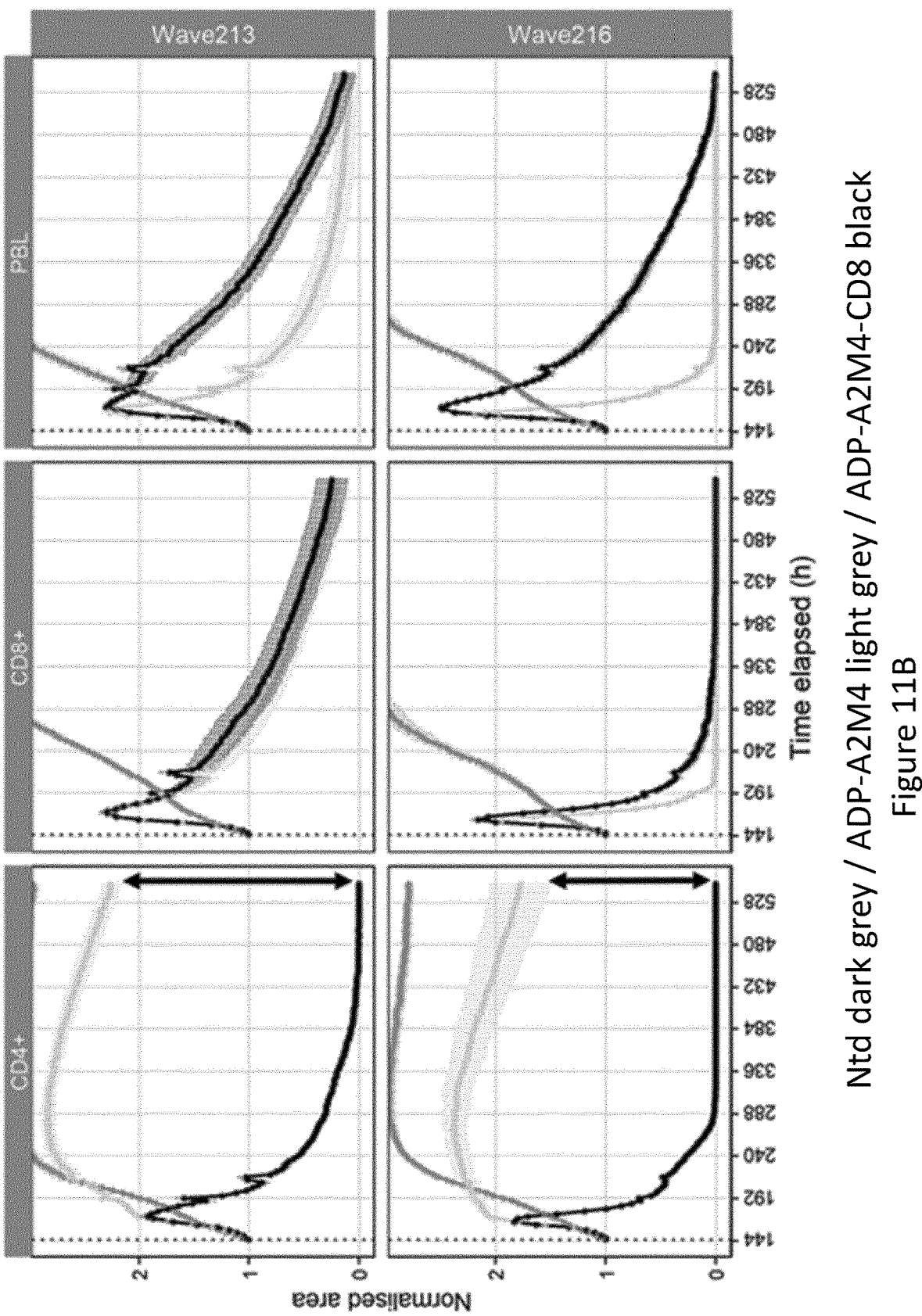

The data of FIGS. 9 and 11 show that following stable microtissue formation at 147 h (A) or 145 h (B), ADP-A2M4 and ADP-A2M4CD8 TCR transduced or ntd PBL (20,000 cells/well), CD4+ isolated (80,000 cells/well), or CD8+ isolated (20,000 cells/well) T cells were added from donors Wave214, Wave215 and Wave217 (A) or Wave213 and Wave216 (B). A & B). FIGS. 9 and 11—panels A & B demonstrate that following addition of ntd T cells, the A375.GFP microtissues continued to grow steadily during the course of the assay before slowing and reaching a limiting size for the assay plate well ~6-8 days after T cell addition. Addition of MAGE-A4 TCR or CD8α_MAGE-A4 TCR T cells from unseparated PBL or pure CD8+ populations to A375.GFP microtissues of both sizes resulted in a short period of microtissue expansion as T cells infiltrated the tissue before rapid and complete destruction of the microtissues. This was measured by a rapid loss of normalised microtissue area (FIGS. 9 and 11—panels A & B).

Figure 10:
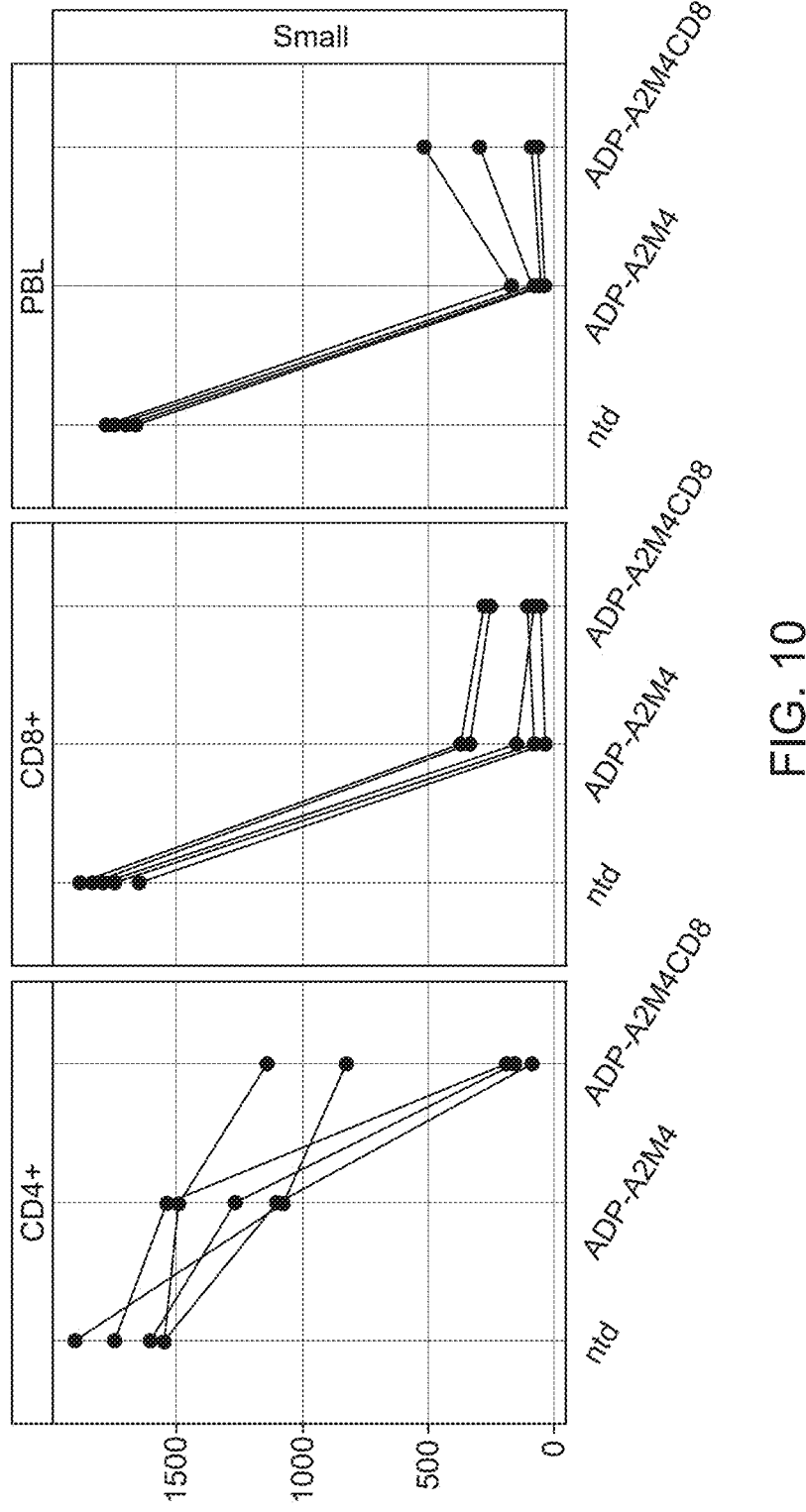
FIG. 10. Cytotoxic activity of ADP-A2M4CD8 T cells towards large, MAGE-A4 expressing A375.GFP microtissues. Scatter plots showing microtissue area under the curve (AUC) with ntd, ADP-A2M4 or ADP-A2M4CD8 for PBL, CD4+ isolated, and CD8+ isolated T cell fractions. Each data point shows the mean of n=6 for all conditions for each Wave product. All data is shown normalised to the timepoint of T cell addition. Repeated measure ANOVA were used to compare overall normalised AUC data within each donor fraction, for small microtissues (ns=not significant; ****=p<0.0001).
Figure 12:
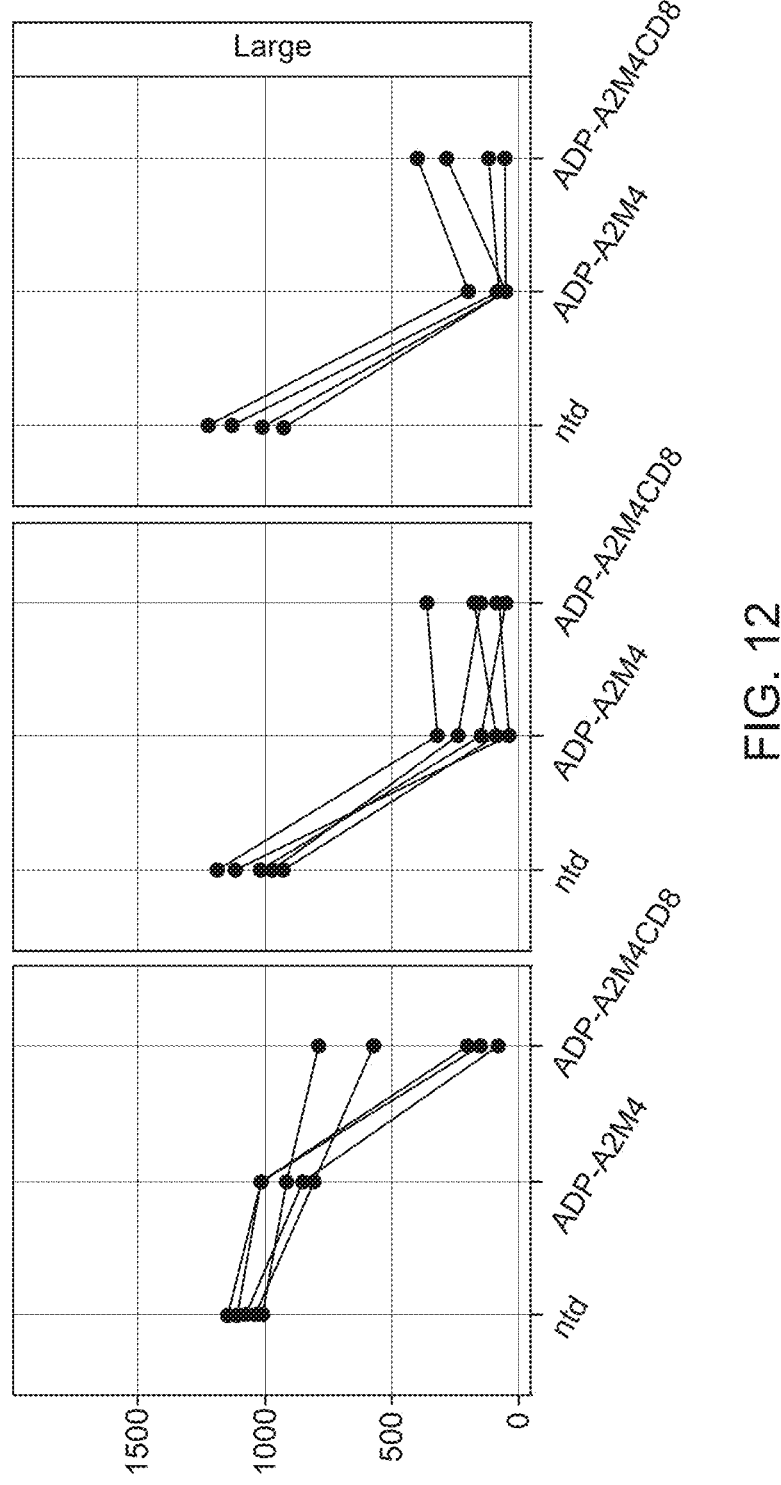
FIG. 12 Cytotoxic activity of ADP-A2M4CD8 T cells towards large, MAGE-A4 expressing A375.GFP microtissues. Scatter plots showing microtissue area under the curve (AUC) with ntd, ADP-A2M4 or ADP-A2M4CD8 for PBL, CD4+ isolated, and CD8+ isolated T cell fractions. Each data point shows the mean of n=6 for all conditions for each Wave product. All data is shown normalised to the timepoint of T cell addition. Repeated measure ANOVA were used to compare overall normalised AUC data within each donor fraction, for small microtissues (ns=not significant; ****=p<0.0001).
Figure 13A:
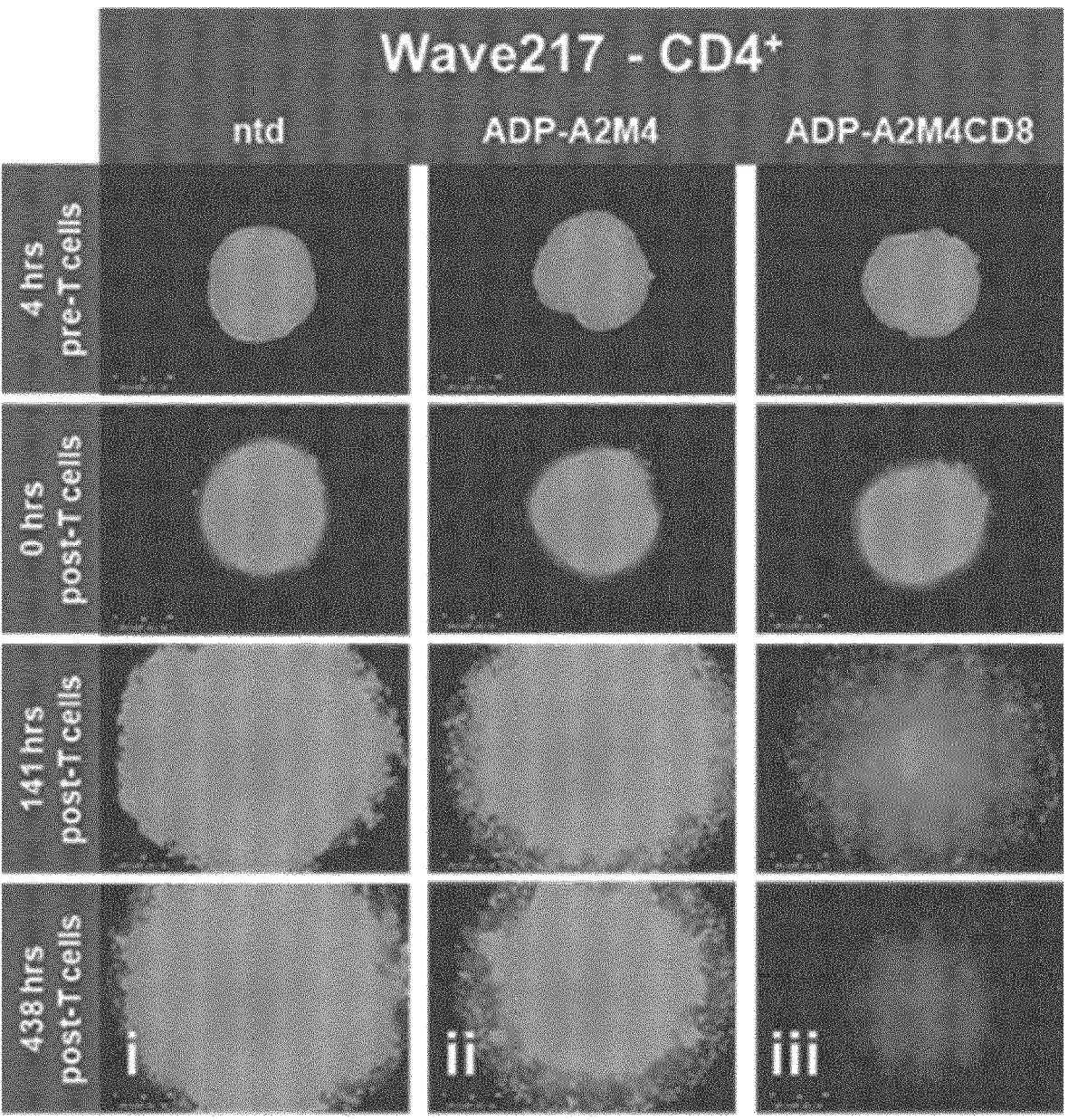
FIG. 13. Cytotoxic activity of CD8α_MAGE-A4 T cells towards small (A) and large (B), MAGE-A4 expressing A375.GFP microtissues. (~800 μm diameter-1200 cells/well seeded). Representative images for Wave donor 217 T cells show the GFP fluorescent microtissue with CD4+ntd, MAGE-A4 TCR and CD8α_MAGE-A4 TCR transduced T cells (80,000 cells/well) at the following time points during the assay: 4 hours pre-T cell addition (=143 hours post target seeding); 0 hours post-T cell addition (=147 hours post target seeding); 141 hours post-T cell addition (=288 hours post target seeding); 438 hours post-T cell addition (=585 hours post target seeding).
Figure 13B:
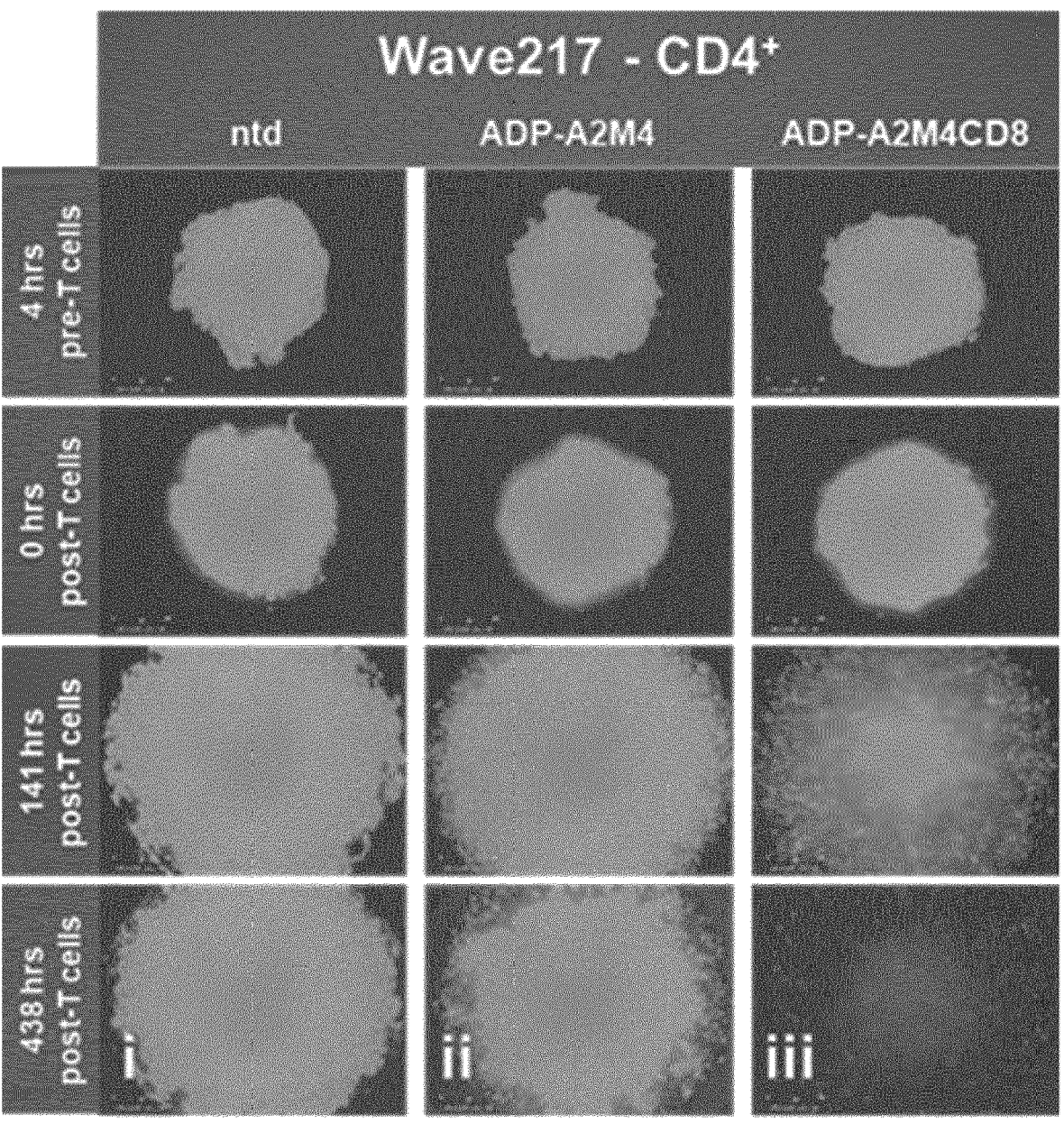

FIGS. 10 and 12 demonstrate that there was no significant difference in the rate of overall killing between MAGE-A4 TCR and CD8α_MAGE-A4 TCR T cells from either unseparated PBLs or pure CD8+ T cell populations (FIGS. 10 and 12—middle and right panels). However transduction of isolated CD4+ T cells with CD8α_MAGE-A4 TCR elicited significantly enhanced cytotoxicity against A375.GFP microtissues of both sizes compared to CD4+ T cells transduced with the MAGE-A4 TCR alone (FIGS. 10 and 12—left panels). All five Wave CD8α_MAGE-A4 TCR T cells products tested consistently showed improved killing of 3D microtissues. Furthermore, complete destruction of both microtissue sizes by CD4+CD8α_MAGE-A4 TCR T cells was achieved by the end of the assay with three of five donors (FIGS. 9 and 11, A-B—left hand side panels; FIG. 13 see 'iii'). These data demonstrate that expression of the CD8α co-receptor significantly enhances the effector function of CD4+ T cells transduced with the MAGE-A4 TCR.

Example 7. CD8α_MAGE-A4 TCR T Cell Production of IFNγ and Granzyme B in Response to A375.GFP 3D Microtissues The ability of MAGE-A4 TCR and CD8α_MAGE-A4 TCR unseparated PBL, purified CD4+ and CD8+ T cells to produce IFNγ and Granzyme B in response to A375.GFP 3D microtissues was assessed. Supernatants were collected from duplicate plates set up in parallel with IncuCyte assays plates after ~50h post T cell addition. Supernatants were analysed for IFNγ and Granzyme B by ELISA in 384 well plates. Sample supernatants were diluted 4-fold in R10 assay medium prior to addition to ELISA plates.

The plates were developed using Glo substrate luminescence HRP substrate and each plate was incubated for five minutes prior to being read on the BMG LABTECH FLUOstar Omega plate reader. Data analysis was conducted in the Omega-data analysis software (version 3.10R6) and 4-fold dilution factor applied to cytokine values obtained to account for sample dilution. Analysed data was exported to Excel and graphed using a custom R script in R version 3.2.2. Within the R script, sample wells that had a value exceeding the highest standard concentration were assigned the value of the top standard. Wells that had a value less than the standard curve range were assigned a value of 0.100 µg/ml above the highest value for the corresponding ntd T cells in the presence of targets without exogenous MAGE-A4 peptide was used to distinguish between a background signal and a positive IFNγ response. 200 µg/ml above the highest value for the corresponding ntd T cells in the presence of targets without exogenous MAGE-A4 peptide was used to distinguish between a background signal and a positive Granzyme B response. Repeated measures ANOVAs were used to compare levels of IFNγ and Granzyme B release within each fraction for the combined data across all waves, for each target microtissue size.

Figure 14A:
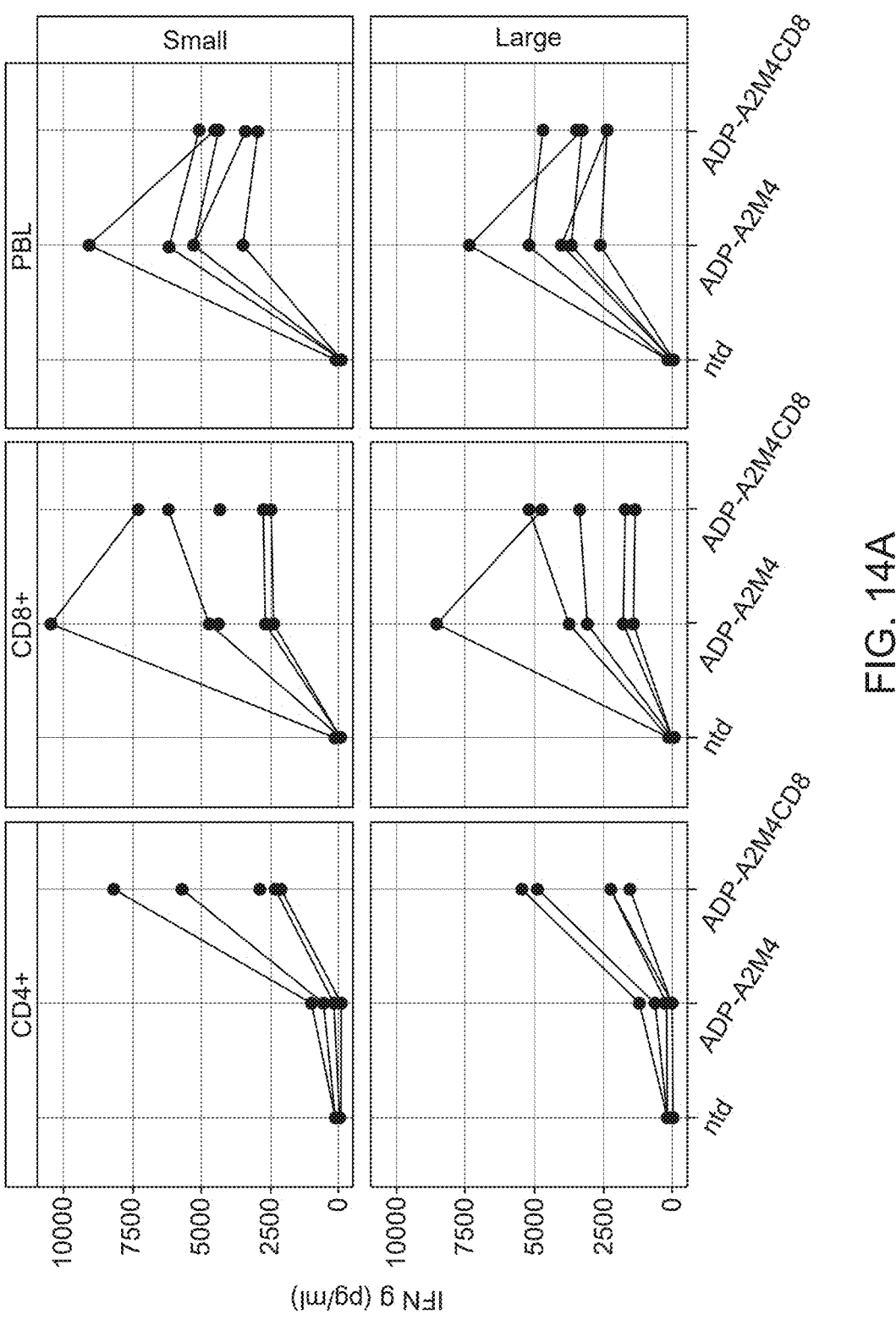
FIG. 14. IFN gamma and Granzyme B release by ntd, ADP-A2M4 and ADP-A2M4CD8 T cells in co-culture with A375.GFP 3D microtissues. Supernatants were collected from duplicate assay plates ~50h post T cell addition. The levels of IFN gamma (A) and Granzyme B (B) in the supernatants were measured by ELISA following 4-fold sample dilution. Graphs display levels of cytokine produced by PBL, CD4+ or CD8+MAGE-A4 TCR T cells, MAGE-A4-CD8 TCR T cells or ntd T cells incubated with small (~505-600 μm diameter) or large (~800 μm diameter) A375.GFP 3D microtissues. Each data point shows the mean of n=6 for all conditions for each Wave product. Repeated measures ANOVAs were used to compare overall IFNγ and Granzyme B release within each donor fraction against small or large microtissues (ns=not significant; ****=p<0.0001). N.B. Granzyme B cytokine values measured that exceeded the maximum detectable range were assigned a value equal to the highest measurable value (=40,000 pg/ml).
Figure 14B:
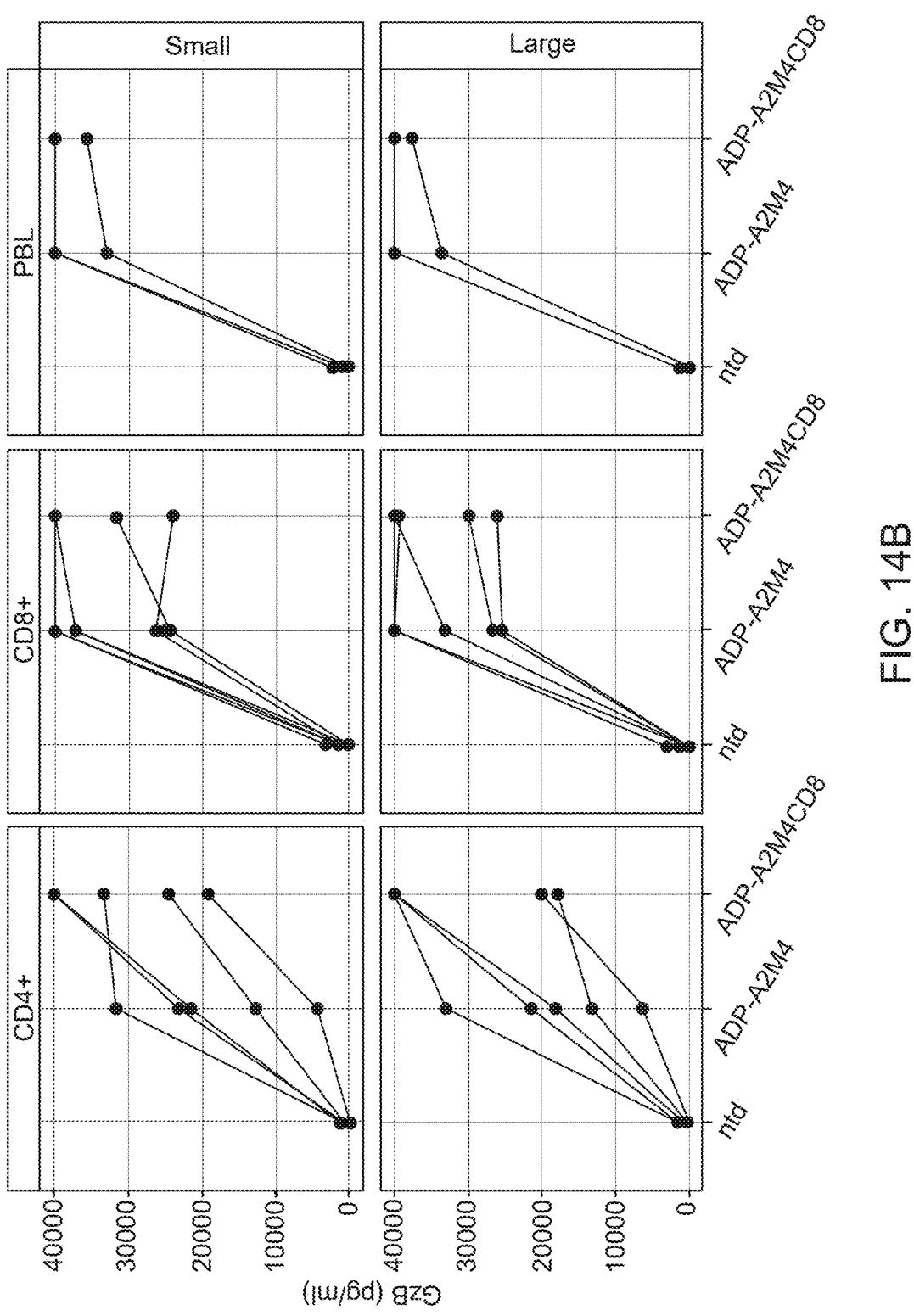

Supernatants were collected from parallel assay plates at −50 hours after T cell addition and assayed by ELISA. Robust cytokine responses were observed with MAGE-A4 TCR and CD8α_MAGE-A4 TCR T cells from unseparated PBL and CD8+ subsets from all five Wave T cell products tested (FIG. 14). No significant difference was observed in the levels of IFNγ or Granzyme B released by MAGE-A4 TCR and CD8α_MAGE-A4 TCR T cells from unseparated PBL or purified CD8+ subsets, respectively. This indicated that additional CD8α co-receptor expression in CD8+ T cells does not result in enhanced cytotoxicity towards antigen positive targets.

The levels of IFNγ and Granzyme B production were significantly increased by CD8α_MAGE-A4 TCR in comparison to MAGE-A4 TCR CD4+ T cells in purified CD4+ T cells across all Wave products tested in response to A375.GFP 3D microtissues of both sizes (FIG. 14—left panels). These data match the enhanced killing capability of CD8α_MAGE-A4 TCR CD4+ T cells compared to MAGE-A4 TCR CD4+ T cells (FIGS. 9-13).

Overall, these data suggest that engineered co-expression of the CD8α homodimer with the MAGE-A4 TCR in CD4+ T cells elicits a substantial improvement in the cytotoxic response towards antigen-positive 3D microtissues compare to CD4+ T cells transduced with the MAGE-A4 TCR alone. This provides rationale for the use of CD8α to enhance the CD4+ T cells transduced with recombinant TCR to enhance potency in the cytotoxic response against antigen positive targets.

---

Sequences

*MALPVTALLLPLALLLHAARP*SQFRVSPLDRTWNLGETVELKCQVLLSNPTSGCSWLFQPRGAAASPTFLLYLSQNK PKAAEGLDTQRFSGKRLGDTFVLTLSDFRRENEGYYFCSALSNSIMYFSHFVPVFLPAKPTTTPAPRPPTPAPTIAS QPLSLRPEACRPAAGGAVHTRGLDFACDIYIWAPLAGTCGVLLLSLVITLYCNHRNRRRVCKCPRPVVKSGDKPSLS ARYV
SEQ ID NO: 1 (CD8α) CDRs bold underlined, signal sequence italic underlined ATGGCCTTACCAGTGACCGCCTTGCTCCTGCCGCTGGCCTTGCTGCTCCACGCCGCCAGGCCGAGCCAGTTCCGGGT
GTCGCCGCTGGATCGGACCTGGAACCTGGGCGAGACAGTGGAGCTGAAGTGCCAGGTGCTGCTGTCCAACCCGACGT

---

Sequences

---

```
CGGGCTGCTCGTGGCTCTTCCAGCCGCGCGGCGCCGCCGCCAGTCCCACCTTCCTCCTATACCTCTCCCAAAACAAG
CCCAAGGCGGCCGAGGGGCTGGACACCCAGCGGTTCTCGGGCAAGAGGTTGGGGGACACCTTCGTCCTCACCCTGAG
CGACTTCGCCGAGAGAACGAGGGCTACTATTTCTGCTCGGCCCTGAGCAACTCCATCATGTACTTCAGCCACTTCG
TGCCGGTCTTCCTGCCAGCGAAGCCCACCACGACGCCAGCGCCGCGACCACCAACACCGGCGCCCACCATCGCGTCG
CAGCCCCTGTCCCTGCGCCCAGAGGCGTGCCGGCCAGCGGCGGGGGGCGCAGTGCACACGAGGGGGCTGGACTTCGC
CTGTGATATCTACATCTGGGCGCCCTTGGCCGGGACTTGTGGGGTCCTTCTCCTGTCACTGGTTATCACCCTTTACT
GCAACCACAGGAACCGAAGACGTGTTTGCAAATGTCCCCGGCCTGTGGTCAAATCGGGAGACAAGCCCAGCCTTTCG
GCGAGATACGTCGGTTCAAGAGCTAAAAGAAGTGGTAGTGGTGCCCCTGTGA
SEQ ID NO: 2 (CD8α)

MKKHLTTFLVILWLYFYRGNGKNQVEQSPQSLIILEGKNCTLQCNYTVSPFSNLRWYKQDTGRGPVSLTILTFSENT
KSNGRYTATLDADTKQSSLHITASQLSDSASYICVVSGGTDSWGKLQFGAGTQVVVTPDIQNPDPAVYQLRDSKSSD
KSVCLFTDFDSQTNVSQSKDSDVYITDKTVLDMRSMDFKSNSAVAWSNKSDFACANAFNNSIIPEDTFFPSPESSCD
VKLVEKSFETDTNLNFQNLSVIGFRILLLKVAGENLLMTLRLWSSGSRAKR
SEQ ID NO: 3 (MAGE A4 TCR α chain) CDRs bold underlined ATGAAGAAGCACCTGACCACCTTTCTCGTGATCCTGTGGCTGTACTTCTACCGGGGCAACGGCAAGAACCAGGTGGA
ACAGAGCCCCCAGAGCCTGATCATCCTGGAAGGCAAGAACTGCACCCTGCAGTGCAACTACACCGTGTCCCCCTTCA
GCAACCTGCGGTGGTACAAGCAGGACACCGGCAGAGGCCCTGTGTCCCTGACCATCCTGACCTTCAGCGAGAACACC
AAGAGCAACGGCCGGTACACCGCCACCCTGGACGCCGATACGAAGCAGAGCTGCACATCACCGCCAGCCAGCT
GAGCGATAGCGCCAGCTACATCTGCGTGGTGTCCGGCGGCACAGACAGCTGGGGCAAGCTGCAGTTTGGCGCCGGAA
CACAGGTGGTCGTGACCCCCGACATCCAGAACCCTGACCCTGCCGTGTACCAGCTGCGGGACAGCAAGAGCAGCGAC
AAGAGCGTGTGCCTGTTCACCGACTTCGACAGCCAGACCAACGTGTCCCAGAGCAAGGACAGCGACGTGTACATCAC
CGACAAGACCGTGCTGGACATGCGGAGCATGGACTTCAAGAGCAATAGCGCGTGGCCTGGTCCAACAAGAGCGACT
TCGCCTGCGCCAACGCCTTCAACAACAGCATTATCCCCGAGGACACATTCTTCCCAAGCCCCGAGAGCAGCTGCGAC
GTCAAGCTGGTGGAAAAGAGCTTCGAGACAGACACCAACCTGAACTTCCAGAACCTGAGCGTGATCGGCTTCAGAAT
CCTGCTGCTGAAGGTGGCCGGCTTCAACCTGCTGATGACCCTGAGACTGTGGTCCAGCGGCAGCCGGGCAAGAGA
SEQ ID NO: 4 (MAGE A4 TCR α chain coding sequence)

MASLLFFCGAFYLLGTGSMDADVTQTPRNRITKTGKRIMLECSQTKGHDRMYWYRQDPGLGLRLIYYSFDVKDINKG
EISDGYSVSRQAQAKFSLSLESAIPNQTALYFCATSGQGAYEEQFFGPGTRLTVLEDLKNVEPPEVA VFEPSEAEIS
HTQKATLVCLATGFYPDHVELSWWVNGKEVHSGVSTDPQPLKEQPALNDSRYCLSSRLRVSATFWQNPRNHFRCQVQ
FYGLSENDEWTQDRAKPVTQIVSAEAWGRADCGFTSESYQQGVLSATILYEILLGKATLYAVLVSALVLMAMVKRKD
SRG
SEQ ID NO: 5 (MAGE A4 TCR ß chain) CDRs bold underlined ATGGCCAGCCTGCTGTTCTTCTGCGGCGCCTTCTACCTGCTGGGCACCGGCTCTATGGATGCCGACGTGACCCAGAC
CCCCCGGAACAGAATCACCAAGACCGGCAAGCGGATCATGCTGGAATGCTCCCAGACCAAGGGCCACGACCGGATGT
ACTGGTACAGACAGGACCCTGGCCTGGGCCTGCGGCTGATCTACTACAGCTTCGACGTGAAGGACATCAACAAGGGC
GAGATCAGCGACGGCTACAGCGTGTCCAGACAGGCTCAGGCCAAGTTCAGCCTGTCCCTGGAAAGCGCCATCCCCAA
CCAGACCGCCCTGTACTTTTGTGCCAAGCGGCCAGGGCGCCTACGAGGAGCAGTTCTTTGGCCCTGGCACCCGGC
TGACAGTGCTGGAAGATCTGAAGAACGTGTTCCCCCCAGAGGTGGCCGTGTTCGAGCCTTCTGAGGCCGAAATCAGC
CACACCCAGAAAGCCACACTCGTGTGTCTGGCCACCGGCTTCTACCCCGACCACGTGGAACTGTCTTGGTGGGTCAA
CGGCAAAGAGGTGCACAGCGGCGTGTCCACCGATCCCCAGCCTCTGAAGGAACAGCCCGCCCTGAACGACAGCCGGT
ACTGCCTGAGCAGCAGACTGAGAGTGTCCGCCACCTTCTGGCAGAACCCCAGAAACCACTTCAGATGCCAGGTGCAG
TTTTACGGCCTGAGCGAGAACGACGAGTGGACCCAGGACAGAGCCAAGCCCGTGACACAGATCGTGTCTGCCGAAGC
TTGGGGGGCGCGCCGATTGTGGCTTTACCAGCGAGAGCTACCAGCAGGGCGTGCTGAGCGCCACCATCCTGTACGAGA
TCCTGCTGGGAAAGGCCACACTGTACGCCGTGCTGGTGTCTGCCCTGGTGCTGATGGCCATGGTCAAGCGGAAGGAC
AGCCGGGGC
SEQ ID NO: 6 (MAGE A4 TCR β chain coding sequence)

MKKHLTTFLVILWLYFYRGNGKNQVEQSPQSLIILEGKNCTLQCNYTVSPFSNLRWYKQDTGRGPVSLTILTFSENT
KSNGRYTATLDADTKQSSLHITASQLSDSASYICVVSGGTDSWGKLQFGAGTQVVVTPD
SEQ ID NO: 7 (MAGE A4 TCR α chain variable region) 136AA-CDRs bold
underlined MASLLFFCGAFYLLGTGSMDADVTQTPRNRITKTGKRIMLECSQTKGHDRMYWYRQDPGLGLRLIYYSFDVKDINKG
EISDGYSVSRQAQAKFSLSLESAIPNQTALYFCATSGQGAYEEQFFGPGTRLTVLE
SEQ ID NO: 8 (MAGE A4 TCR ß chain variable region) 133AA-CDRs bold
underlined
```

VSPFSN SEQ ID NO: 9; CDR1 MAGE A4 TCR α chain, (residues 48-53)

LTFSEN SEQ ID NO: 10; CDR2 MAGE A4 TCR α chain, (residues 71-76)

CVVSGGTDSWGKLQF SEQ ID NO: 11; CDR3 MAGE A4 TCR α chain, (residues 111-125)

KGHDR SEQ ID NO: 12; CDR1 MAGE A4 TCR ß chain, (residues 46-50)

SFDVKD SEQ ID NO: 13; CDR2 MAGE A4 TCR ß chain, (residues 68-73)

CATSGQGAYEEQFF SEQ ID NO: 14; CDR3 MAGE A4 TCR ß chain, (residues 110-123)

VLLSNPTSG SEQ ID NO: 15; CDR1 CD8α (residues 45-53)

YLSQNKPK SEQ ID NO: 16; CDR2 CD8α (residues 72-79)

-continued

| Sequences |
| --- |

LSNSIM SEQ ID NO: 17; CDR3 CD8α (residues 118-123)

GVYDGREHTV-SEQ ID NO: 18

The invention claimed is:

1. An isolated modified T cell or a population of isolated modified T cells comprising a heterologous homodimeric CD8αco-receptor and a heterologous T cell receptor (TCR) that binds MAGE-A4.

2. The modified T cell or the population of modified T cells according to claim 1, wherein the CD8α co-receptor comprises an amino acid sequence having at least 80% sequence identity to the amino acid sequence of SEQ ID NO: 1.

3. The modified T cell or the population of modified T cells according to claim 1, wherein the TCR binds a cancer or a tumour antigen or a peptide thereof and/or is an affinity enhanced TCR.

4. The modified T cell or the population of modified T cells according to claim 1, wherein the TCR comprises an a chain amino acid sequence having at least 80% sequence identity to the amino acid sequence of SEQ ID NO: 3.

5. The modified T cell or the population of modified T cells according to claim 4, wherein the TCR further comprises a β chain amino acid sequence having at least 80% sequence identity to the amino acid sequence of SEQ ID NO: 5.

6. The modified T cell or the population of modified T cells according to claim 1, wherein the modified T cell or cells are CD4+.

7. The modified T cell or the population of modified T cells according to claim 1, wherein the TCR comprises an a chain variable region comprising the amino acid sequence of SEQ ID NO:7 and a β chain variable region comprising the amino acid sequence of SEQ ID NO:8.

8. The modified T cell or the population of modified T cells according to claim 1, wherein the TCR comprises an α chain variable region (Vα) comprising complementarity determining regions (CDRs) Vα CDR1, Vα CDR2, and Vα CDR3 and a β chain variable region (Vβ) comprising CDRs Vβ CDR1, Vβ CDR2, and Vβ CDR3, wherein the Vα CDR1 comprises the amino acid sequence of SEQ ID NO: 9, the Vα CDR2 comprises the amino acid sequence of SEQ ID NO: 10, the Vα CDR3 comprises the amino acid sequence of SEQ ID NO: 11, the Vβ CDR1 comprises the amino acid sequence of SEQ ID NO: 12, the Vβ CDR2 comprises the amino acid sequence of SEQ ID NO: 13, and the Vβ CDR3 comprises the amino acid sequence of SEQ ID NO: 14.

* * * * *

SEQUENCE LISTING

<160> NUMBER OF SEQ ID NOS: 18

<210> SEQ ID NO 1
<211> LENGTH: 235
<212> TYPE: PRT
<213> ORGANISM: Artificial Sequence
<220> FEATURE:
<223> OTHER INFORMATION: Synthetic

<400> SEQUENCE: 1

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
            130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235
```

<210> SEQ ID NO 2
<211> LENGTH: 745
<212> TYPE: DNA
<213> ORGANISM: Artificial Sequence
<220> FEATURE:
<223> OTHER INFORMATION: Synthetic

<400> SEQUENCE: 2

```
atggccttac cagtgaccgc cttgctcctg ccgctggcct tgctgctcca cgccgccagg    60
```

```
ccgagccagt tccgggtgtc gccgctggat cggacctgga acctgggcga gacagtggag        120
ctgaagtgcc aggtgctgct gtccaacccg acgtcgggct gctcgtggct cttccagccg        180
cgcggcgccg ccgccagtcc caccttcctc ctatacctct cccaaaacaa gcccaaggcg        240 gccgagggggc tggacaccca gcggttctcg ggcaagaggt tggggggacac cttcgtcctc      300 accctgagcg acttccgccg agagaacgag ggctactatt tctgctcggc cctgagcaac        360
tccatcatgt acttcagcca cttcgtgccg gtcttcctgc cagcgaagcc caccacgacg        420
ccagcgccgc gaccaccaac accggcgccc accatcgcgt cgcagcccct gtccctgcgc        480
ccagaggcgt gccggccagc ggcggggggc gcagtgcaca cgaggggggct ggacttcgcc       540 tgtgatatct acatctgggc gcccttggcc gggacttgtg gggtccttct cctgtcactg        600
gttatcaccc tttactgcaa ccacaggaac cgaagacgtg tttgcaaatg tccccggcct        660
gtggtcaaat cgggagacaa gcccagcctt tcggcgagat acgtcggttc aagagctaaa        720
agaagtggta gtggtgccccc tgtga        745
```

<210> SEQ ID NO 3
<211> LENGTH: 282
<212> TYPE: PRT
<213> ORGANISM: Artificial Sequence
<220> FEATURE:
<223> OTHER INFORMATION: Synthetic

<400> SEQUENCE: 3

```
Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
            35                  40                  45

Ser Pro Phe Ser Asn Leu Arg Trp Tyr Lys Gln Asp Thr Gly Arg Gly
        50                  55                  60

Pro Val Ser Leu Thr Ile Leu Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Gly Gly Thr Asp Ser Trp Gly Lys Leu Gln Phe Gly Ala Gly
            115                 120                 125

Thr Gln Val Val Val Thr Pro Asp Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
        210                 215                 220

Ser Pro Glu Ser Ser Cys Asp Val Lys Leu Val Glu Lys Ser Phe Glu
225                 230                 235                 240
```

-continued

```
Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser Gly Ser Arg Ala Lys Arg
        275                 280

<210> SEQ ID NO 4
<211> LENGTH: 846
<212> TYPE: DNA
<213> ORGANISM: Artificial Sequence
<220> FEATURE:
<223> OTHER INFORMATION: Synthetic

<400> SEQUENCE: 4
atgaagaagc acctgaccac ctttctcgtg atcctgtggc tgtacttcta ccggggcaac      60
ggcaagaacc aggtggaaca gagcccccag agcctgatca tcctggaagg caagaactgc     120
accctgcagt gcaactacac cgtgtccccc ttcagcaacc tgcggtggta caagcaggac     180
accggcagag ccctgtgtc cctgaccatc ctgaccttca gcgagaacac caagagcaac     240
ggccggtaca ccgccaccct ggacgccgat acaaagcaga gcagcctgca catcaccgcc     300
agccagctga gcgatagcgc cagctacatc tgcgtggtgt ccggcggcac agacagctgg     360
ggcaagctgc agtttggcgc cggaacacag gtggtcgtga cccccgacat ccagaaccct     420
gaccctgccg tgtaccagct gcgggacagc aagagcagcg acaagagcgt gtgcctgttc     480
accgacttcg acagccagac caacgtgtcc cagagcaagg acagcgacgt gtacatcacc     540
gacaagaccg tgctggacat gcggagcatg gacttcaaga gcaatagcgc cgtggcctgg     600
tccaacaaga gcgacttcgc ctgcgccaac gccttcaaca acagcattat ccccgaggac     660
acattcttcc aagccccga gagcagctgc gacgtcaagc tggtggaaaa gagcttcgag     720
acagacacca acctgaactt ccagaacctg agcgtgatcg gcttcagaat cctgctgctg     780
aaggtggccg gcttcaacct gctgatgacc ctgagactgt ggtccagcgg cagccgggcc     840
aagaga                                                              846

<210> SEQ ID NO 5
<211> LENGTH: 311
<212> TYPE: PRT
<213> ORGANISM: Artificial Sequence
<220> FEATURE:
<223> OTHER INFORMATION: Synthetic

<400> SEQUENCE: 5

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
```

```
                  100              105              110
Ser Gly Gln Gly Ala Tyr Glu Glu Gln Phe Phe Gly Pro Gly Thr Arg
            115              120              125

Leu Thr Val Leu Glu Asp Leu Lys Asn Val Phe Pro Pro Glu Val Ala
    130              135              140

Val Phe Glu Pro Ser Glu Ala Glu Ile Ser His Thr Gln Lys Ala Thr
145              150              155              160

Leu Val Cys Leu Ala Thr Gly Phe Tyr Pro Asp His Val Glu Leu Ser
                165              170              175

Trp Trp Val Asn Gly Lys Glu Val His Ser Gly Val Ser Thr Asp Pro
                180              185              190

Gln Pro Leu Lys Glu Gln Pro Ala Leu Asn Asp Ser Arg Tyr Cys Leu
            195              200              205

Ser Ser Arg Leu Arg Val Ser Ala Thr Phe Trp Gln Asn Pro Arg Asn
    210              215              220

His Phe Arg Cys Gln Val Gln Phe Tyr Gly Leu Ser Glu Asn Asp Glu
225              230              235              240

Trp Thr Gln Asp Arg Ala Lys Pro Val Thr Gln Ile Val Ser Ala Glu
                245              250              255

Ala Trp Gly Arg Ala Asp Cys Gly Phe Thr Ser Glu Ser Tyr Gln Gln
                260              265              270

Gly Val Leu Ser Ala Thr Ile Leu Tyr Glu Ile Leu Leu Gly Lys Ala
            275              280              285

Thr Leu Tyr Ala Val Leu Val Ser Ala Leu Val Leu Met Ala Met Val
    290              295              300

Lys Arg Lys Asp Ser Arg Gly
305              310
```

```
<210> SEQ ID NO 6
<211> LENGTH: 933
<212> TYPE: DNA
<213> ORGANISM: Artificial Sequence
<220> FEATURE:
<223> OTHER INFORMATION: Synthetic

<400> SEQUENCE: 6
atggccagcc tgctgttctt ctgcggcgcc ttctacctgc tgggcaccgg ctctatggat     60
gccgacgtga cccagacccc ccggaacaga atcaccaaga ccggcaagcg gatcatgctg    120
gaatgctccc agaccaaggg ccacgaccgg atgtactggt acagacagga ccctggcctg    180
ggcctgcggc tgatctacta cagcttcgac gtgaaggaca tcaacaaggg cgagatcagc    240
gacggctaca gcgtgtccag acaggctcag gccaagttca gcctgtccct ggaaagcgcc    300
atccccaacc agaccgccct gtactttgt gccacaagcg gccagggcgc ctacgaggag    360
cagttctttg gccctggcac ccggctgaca gtgctggaag atctgaagaa cgtgttcccc    420
ccagaggtgg ccgtgttcga gccttctgag gccgaaatca gccacaccca gaaagccaca    480
ctcgtgtgtc tggccaccgg cttctacccc gaccacgtgg aactgtcttg gtgggtcaac    540
ggcaaagagg tgcacagcgg cgtgtccacc gatccccagc ctctgaaaga acagcccgcc    600
ctgaacgaca gccggtactg cctgagcagc agactgagag tgtccgccac cttctggcag    660
aaccccagaa accacttcag atgccaggtg cagttttacg gcctgagcga aaacgacgag    720
tggacccagg acagagccaa gcccgtgaca cagatcgtgt ctgccgaagc ttggggccgc    780
gccgattgtg gctttaccag cgagagctac cagcagggcg tgctgagcgc caccatcctg    840
```

-continued

```
tacgagatcc tgctgggaaa ggccacactg tacgccgtgc tggtgtctgc cctggtgctg      900
atggccatgg tcaagcggaa ggacagccgg ggc                                    933
```

```
<210> SEQ ID NO 7
<211> LENGTH: 136
<212> TYPE: PRT
<213> ORGANISM: Artificial Sequence
<220> FEATURE:
<223> OTHER INFORMATION: Synthetic

<400> SEQUENCE: 7

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
                20                  25                  30

Ile Ile Leu Glu Gly Lys Asn Cys Thr Leu Gln Cys Asn Tyr Thr Val
                35                  40                  45

Ser Pro Phe Ser Asn Leu Arg Trp Tyr Lys Gln Asp Thr Gly Arg Gly
            50                  55                  60

Pro Val Ser Leu Thr Ile Leu Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                    85                  90                  95

His Ile Thr Ala Ser Gln Leu Ser Asp Ser Ala Ser Tyr Ile Cys Val
                100                 105                 110

Val Ser Gly Gly Thr Asp Ser Trp Gly Lys Leu Gln Phe Gly Ala Gly
            115                 120                 125

Thr Gln Val Val Val Thr Pro Asp
        130                 135

<210> SEQ ID NO 8
<211> LENGTH: 133
<212> TYPE: PRT
<213> ORGANISM: Artificial Sequence
<220> FEATURE:
<223> OTHER INFORMATION: Synthetic

<400> SEQUENCE: 8

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
                20                  25                  30

Lys Thr Gly Lys Arg Ile Met Leu Glu Cys Ser Gln Thr Lys Gly His
            35                  40                  45

Asp Arg Met Tyr Trp Tyr Arg Gln Asp Pro Gly Leu Gly Leu Arg Leu
            50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                    85                  90                  95

Leu Glu Ser Ala Ile Pro Asn Gln Thr Ala Leu Tyr Phe Cys Ala Thr
                100                 105                 110

Ser Gly Gln Gly Ala Tyr Glu Glu Gln Phe Phe Gly Pro Gly Thr Arg
            115                 120                 125

Leu Thr Val Leu Glu
        130
```

-continued

```
<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Val Ser Pro Phe Ser Asn
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Leu Thr Phe Ser Glu Asn
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Cys Val Val Ser Gly Gly Thr Asp Ser Trp Gly Lys Leu Gln Phe
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Lys Gly His Asp Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Ser Phe Asp Val Lys Asp
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Cys Ala Thr Ser Gly Gln Gly Ala Tyr Glu Glu Gln Phe Phe
1               5                   10

<210> SEQ ID NO 15
```

-continued

```
<211> LENGTH: 9
<212> TYPE: PRT
<213> ORGANISM: Artificial Sequence
<220> FEATURE:
<223> OTHER INFORMATION: Synthetic

<400> SEQUENCE: 15

Val Leu Leu Ser Asn Pro Thr Ser Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Tyr Leu Ser Gln Asn Lys Pro Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Leu Ser Asn Ser Ile Met
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly Val Tyr Asp Gly Arg Glu His Thr Val
1               5                   10
```